(12) United States Patent
Calvo et al.

(10) Patent No.: US 8,530,162 B2
(45) Date of Patent: Sep. 10, 2013

(54) METHOD FOR SELECTIVELY QUANTIFYING VEGF ISOFORMS IN A BIOLOGICAL SAMPLE AND USES THEREOF

(75) Inventors: Fabien Calvo, Paris (FR); Samia Mourah, Paris (FR); Benyoussef Naimi, Paris (FR)

(73) Assignees: INSERM (Institut National de la Santa et de la Recherche Medicale), Paris (FR); Assistance Publique-Hopitaux de Paris, Paris (FR)

( * ) Notice: Subject to any disclaimer, the term of this patent is extended or adjusted under 35 U.S.C. 154(b) by 1690 days.

(21) Appl. No.: 11/629,197

(22) PCT Filed: Jun. 14, 2005

(86) PCT No.: PCT/EP2005/007066
§ 371 (c)(1),
(2), (4) Date: Jan. 11, 2007

(87) PCT Pub. No.: WO2005/121362
PCT Pub. Date: Dec. 22, 2005

(65) Prior Publication Data
US 2010/0167273 A1    Jul. 1, 2010

(30) Foreign Application Priority Data
Jun. 14, 2004    (EP) .................................... 04291485

(51) Int. Cl.
*C12Q 1/68* (2006.01)
*C07H 21/04* (2006.01)

(52) U.S. Cl.
USPC ........................................ 435/6.12; 536/24.3

(58) Field of Classification Search
None
See application file for complete search history.

(56) References Cited

U.S. PATENT DOCUMENTS

| | | | | |
|---|---|---|---|---|
| 5,922,855 A * | 7/1999 | Liskay et al. | ................. | 536/23.5 |
| 2002/0028487 A1 * | 3/2002 | La Thangue et al. | ........ | 435/69.1 |
| 2002/0061545 A1 * | 5/2002 | Choi et al. | .................... | 435/7.34 |
| 2003/0228620 A1 * | 12/2003 | Du Breuil Lastrucci | ......... | 435/6 |
| 2004/0209241 A1 * | 10/2004 | Hermanson et al. | .............. | 435/5 |

OTHER PUBLICATIONS

GenBank GI:19909064 [online] Apr. 3, 2002 [retrieved on Mar. 31, 2010] retrieved from http://www.ncbi.nlm.nih.gov/nuccore/19909064.*
Proudnikov et al. Optimizing primer-probe design for fluorescent PCR. Journal of Neuroscience Methods 123:31-45 (2003).*
Tischer et al. The human gene for vascular endothelial growth factor. J Biol Chem 266(18):11947-11954 (1991).*
Schuch et al. In vivo administration of vascular endothelial growth factor (VEGF) and its antagonist, soluble neuropilin-1, predicts a role of VEGF in the progression of acute myeloid leukemia in vivo. Blood 100(13):4622-8 (2002).*
Scott et al. Differential expression of vascular endothelial growth factor mRNA vs protein isoform expression in human breast cancer and relationship to eIF-4E. British Journal of Cancer 77(12):2120-2128 (1998).*
David O. Bates, et al., "VEGF 165B, an Inhibitory Splice Variant of Vascular Endothelial Growth Factor, Is Down-Regulated in Renal Cell Carcinoma", Cancer Research, vol. 62, No. 14, XP 001148811, pp. 4123-4131, 2002.
Ang Yuan, et al., "Vascular Endothelial Growth Factor 189 mRNA Isoform Expression Specifically Correlates With Tumor Angiogenesis, Patient Survival, and Postoperative Relapse in Non-Small-Cell Lung Cancer", Journal of Clinical Oncology, vol. 19, No. 2, XP 002348592, pp. 432-441, 2001.
Van Trappen, et al., "A Model for Co-Expression Pattern Analysis of Genes Implicated in Angiogenesis and Tumour Cell Invasion in Cervical Cancer", British Journal of Cancer, vol. 87, No. 5, XP 002308015, pp. 537-544, 2002.
Sven Wellmann, et al., "Specific Reverse Transcription-PCR Quantification of Vascular Endothelial Growth Factor (VEGF) Splice Variants by Lightcycler Technology", Clinical Chemistry, vol. 47, No. 4, XP 002308014, pp. 654-660, 2001.
Jochen G. Hofstaetter, et al., "Differential Expression of VEGF Isoforms and Receptors in Knee Joint Menisci Under Systemic Hypoxia", Biochemical and Biophysical Research Communications, vol. 324, No. 2, XP 004599658, pp. 667-672, 2004.

* cited by examiner

*Primary Examiner* — Samuel Woolwine
(74) *Attorney, Agent, or Firm* — Oblon, Spivak, McClelland, Maier & Neustadt, L.L.P.

(57) ABSTRACT

The present invention pertains to a novel method for quantifying VEGF various isoforms in a biological sample, with a very high selectivity and sensitivity. It also concerns a method for establishing a diagnostic and/or a prognosis concerning a patient potentially suffering from cancer, diabetes, or cardiovascular disease, comprising a step of determining the level of at least one of the VEGF isoforms, in a biological sample from said patient.

8 Claims, 25 Drawing Sheets

Figure 1A:
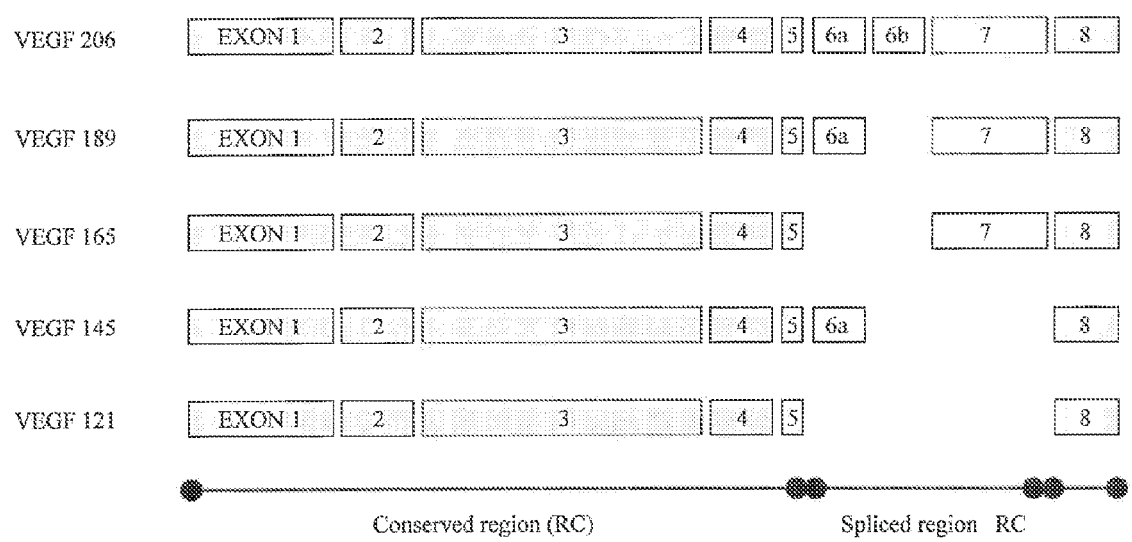

TCGCGGAGGCTTGGGGCAGCCGGGTAGCTCGGAGGTCGTGGCGCTGGGGG
CTAGCACCAGCGCTCTGTCGGGAGGCGCAGCGGTTAGGTGGACCGGTCAG
CGGACTCACCGGCCAGGGCGCTCGGTGCTGGAATTTGATATTCATTGATC
CGGGTTTTATCCCTCTTCTTTTTTCTTAAACATTTTTTTTTAAAACTGTA
TTGTTTCTCGTTTTAATTTATTTTTGCTTGCCATTCCCCACTTGAATCGG
GCCGACGGCTTGGGGAGATTGCTCTACTTCCCCAAATCACTGTGGATTTT
GGAAACCAGCAGAAAGAGGAAAGAGGTAGCAAGAGCTCCAGAGAGAAGTC
GAGGAAGAGAGAGACGGGGTCAGAGAGAGCGCGCGGGCGTGCGAGCAGCG
AAAGCGACAGGGGCAAAGTGAGTGACCTGCTTTTGGGGGTGACCGCCGGA
GCGCGGCGTGAGCCCTCCCCCTTGGGATCCCGCAGCTGACCAGTCGCGCT
GACGGACAGACAGACAGACACCGCCCCAGCCCCAGCTACCACCTCCTCC
CCGGCCGGCGGCGGACAGTGGACGCGGCGGCGAGCCGCGGGCAGGGGCCG
GAGCCCGCGCCCGGAGGCGGGGTGGAGGGGGTCGGGGCTCGCGGCGTCGC
ACTGAAACTTTTCGTCCAACTTCTGGGCTGTTCTCGCTTCGGAGGAGCCG
TGGTCCGCGCGGGGAAGCCGAGCCGAGCGGAGCCGCGAGAAGTGCTAGC
TCGGGCCGGGAGGAGCCGCAGCCGGAGGAGGGGGAGGAGGAAGAAGAGAA
GGAAGAGGAGAGGGGGCCGCAGTGGCGACTCGGCGCTCGGAAGCCGGGCT
CATGGACGGGTGAGGCGGCGGTGTGCGCAGACAGTGCTCCAGCCGCGCGC
GCTCCCCAGGCCCTGGCCCGGGCCTCGGGCCGGGGAGGAAGAGTAGCTCG
CCGAGGCGCCGAGGAGAGCGGGCCGCCCACAGCCCGAGCCGGAGAGGGA                Exon 1
GCGCGAGCCGCGCCGGCCCCGGTCGGGCCTCCGAAACCATGAACTTTCTG
CTGTCTTGGGTGCATTGGAGCCTTGCCTTGCTGCTCTACCTCCACCATGC
CAAG*TGGTCCCAGGCTGCACCCATGGCAGAAGGAGGAGGGCAGAATCATC*       Exon 2
*ACGAAGTGGTGAAGTTCATGGATGTCTATCAGCGCAGCTACTGCCATCCA*
*ATCGAGACCCTGGTGGACATCTTCCAGGAGTACCCTGATGAGATCGAGTA*
*CATCTTCAAGCCATCCTGTGTGCCCCTGATGCGATGCGGGGCTGCTGCA*                Exon 3
*ATGACGAGGGCCTGGAGTGTGTGCCCACTGAGGAGTCCAACATCACCATG*
*CAGATTATGCGGATCAAAĈTCACCAAGGCCAGCACATAGGAGAGATGAG*         Exon 4
CTTCCTACAGCACAACAAATGTGAATGCAGACCAAAGAAAGATAGAGCAA         Exon 5
GACAAGAAAATCCCTGTGGGCCTTGCTCAGAGCGGAGAAAGCATTTGTTT
*GTACAAGATCCGCAGACGTGTAAATGTTCTGCAAAACACAGACTCGCG*           Exon 7
*TTGCAAGGCGAGGCAGCTTGAGTTAAACGAACGTACTTGCAGATGTGACA*
AGCCGAGGCGGTGAGCCGGGCAGGAGGAAGGAGCCTCCCTCAGGGTTTCG         Exon 8
G

Fig. 1B

```
TCGCGGAGGCTTGGGGCAGCCGGGTAGCTCGGAGGTCGTGGCGCTGGGGG
CTAGCACCAGCGCTCTGTCGGGAGGCGCAGCGGTTAGGTGGACCGGTCAG
CGGACTCACCGGCCAGGGCGCTCGGTGCTGGAATTTGATATTCATTGATC
CGGGTTTTATCCCTCTTCTTTTTTCTTAAACATTTTTTTTTAAAACTGTA
TTGTTTCTCGTTTTAATTTATTTTTGCTTGCCATTCCCCACTTGAATCGG
GCCGACGGCTTGGGGAGATTGCTCTACTTCCCCAAATCACTGTGGATTTT
GGAAACCAGCAGAAAGAGGAAAGAGGTAGCAAGAGCTCCAGAGAGAAGTC
GAGGAAGAGAGAGACGGGGTCAGAGAGAGCGCGCGGGCGTGCGAGCAGCG
AAAGCGACAGGGGCAAAGTGAGTGACCTGCTTTTGGGGGTGACCGCCGGA
GCGCGGCGTGAGCCCTCCCCCTTGGGATCCCGCAGCTGACCAGTCGCGCT     Exon 1
GACGGACAGACAGACAGACACCGCCCCAGCCCCAGCTACCACCTCCTCC
CCGGCCGGCGGCGGACAGTGGACGCGGCGGCGAGCCGCGGGCAGGGCCG
GAGCCCGCGCCCGGAGGCGGGGTGGAGGGGGTCGGGGCTCGCGGCGTCGC
ACTGAAACTTTTCGTCCAACTTCTGGGCTGTTCTCGCTTCGGAGGAGCCG
TGGTCCGCGCGGGGAAGCCGAGCCGAGCGGAGCCGCGAGAAGTGCTAGC
TCGGGCCGGGAGGAGCCGCAGCCGGAGGAGGGGGAGGAGGAAGAAGAGAA
GGAAGAGGAGAGGGGGCCGCAGTGGCGACTCGGCGCTCGGAAGCCGGGCT
CATGGACGGGTGAGGCGGCGGTGTGCGCAGACAGTGCTCCAGCCGCGCGC
GCTCCCCAGGCCCTGGCCCGGGCCTCGGGCCGGGGAGGAAGAGTAGCTCG
CCGAGGCGCCGAGGAGAGCGGGCCGCCCCACAGCCCGAGCCGGAGAGGGA
GCGCGAGCCGCGCCGGCCCCGGTCGGGCCTCCGAAACCATGAACTTTCTG
CTGTCTTGGGTGCATTGGAGCCTTGCCTTGCTGCTCTACCTCCACCATGC
CAAG*TGGTCCCAGGCTGCACCCATGGCAGAAGGAGGAGGGCAGAATCATC*     Exon 2
*ACGAAGTGGTGAAGTTCATGGATGTCTATCAGCGCAGCTACTGCCATCCA*
*ATCGAGACCCTGGTGGACATCTTCCAGGAGTACCCTGATGAGATCGAGTA*
*CATCTTCAAGCCATCCTGTGTGCCCCTGATGCGATGCGGGGGCTGCTGCA*     Exon 3
*ATGACGAGGGCCTGGAGTGTGTGCCCACTGAGGAGTCCAACATCACCATG*
*CAGATTATGCGGATCAAACCTCACCAAGGCCAGCACATAGGAGAGATGAG*     Exon 4
*CTTCCTACAGCACAACAAATGTGAATGCAGACCAAAGAAAGATAGAGCAA*     Exon 5
*GACAAGAAAAATGTGACAAGCCGAGGCGG***TGA***GCCGGGCAGGAGGAAGGA*     Exon 8
*GCCTCCCTCAGGGTTTCGG*
```

Fig. 1C

TCGCGGAGGCTTGGGGCAGCCGGGTAGCTCGGAGGTCGTGGCGCTGGGGG
CTAGCACCAGCGCTCTGTCGGAGGCGCAGCGGTTAGGTGGACCGGTCAG
CGGACTCACCGGCCAGGGCGCTCGGTGCTGGAATTTGATATTCATTGATC
CGGGTTTTATCCCTCTTCTTTTTTCTTAAACATTTTTTTTTAAAACTGTA
TTGTTTCTCGTTTTAATTTATTTTTGCTTGCCATTCCCCACTTGAATCGG
GCCGACGGCTTGGGGAGATTGCTCTACTTCCCCAAATCACTGTGGATTTT
GGAAACCAGCAGAAAGAGGAAAGAGGTAGCAAGAGCTCCAGAGAGAAGTC
GAGGAAGAGAGAGACGGGGTCAGAGAGAGCGCGCGGGCGTGCGAGCAGCG
AAAGCGACAGGGGCAAAGTGAGTGACCTGCTTTTGGGGGTGACCGCCGGA
GCGCGGCGTGAGCCCTCCCCCTTGGGATCCCGCAGCTGACCAGTCGCGCT
GACGGACAGACAGACAGACACCGCCCCAGCCCCAGCTACCACCTCCTCC
CCGGCCGGCGGCGGACAGTGGACGCGGCGGCGAGCCGCGGGCAGGGGCCG
GAGCCCGCGCCCGGAGGCGGGGTGGAGGGGGTCGGGCTCGCGGCGTCGC
ACTGAAACTTTTCGTCCAACTTCTGGGCTGTTCTCGCTTCGGAGGAGCCG
TGGTCCGCGCGGGGAAGCCGAGCCGAGCGGAGCCGCGAGAAGTGCTAGC
TCGGGCCGGGAGGAGCCGCAGCCGGAGGAGGGGGAGGAGGAAGAAGAGAA
GGAAGAGGAGAGGGGGCCGCAGTGGCGACTCGGCGCTCGGAAGCCGGGCT
CATGGACGGGTGAGGCGGCGGTGTGCGCAGACAGTGCTCCAGCCGCGCGC
GCTCCCCAGGCCCTGGCCCGGGCCTCGGCCGGGGAGGAAGAGTAGCTCG
CCGAGGCGCCGAGGAGAGCGGGCCGCCCCACAGCCCGAGCCGGAGAGGGA                    Exon1
GCGCGAGCCGCGCCGGCCCCGGTCGGGCCTCCGAAACCATGAACTTTCTG
CTGTCTTGGGTGCATTGGAGCCTTGCCTTGCTGCTCTACCTCCACCATGC
CAAG*TGGTCCAGGCTGCACCCATGGCAGAAGGAGGAGGGCAGAATCATC*              *Exon 2*
*ACGAAGTGGTGAAGTTCATGGATGTCTATCAGCGCAGCTACTGCCATCCA*
*ATCGAGACCCTGGTGGACATCTTCCAGGAGTACCCTGATGAGATCGAGTA*
*CATCTTCAAGCCATCCTGTGTGCCCCTGATGCGATGCGGGGGCTGCTGCA*                Exon3
*ATGACGAGGGCCTGGAGTGTGTGCCCACTGAGGAGTCCAACATCACCATG*
*CAGATTATGCGGATCAAACCTCACCAAGGCCAGCACATAGGAGAGATGAG*          *Exon 4*
CTTCCTACAGCACAACAAATGTGAATGCAGACCAAAGAAAGATAGAGCAA              Exon5
GACAAGAAAAAAATCAGTTCGAGGAAAGGGAAAGGGGCAAAAACGAAAG              *Exon6a*
*CGCAAGAAATCCCGGTATAAGTCCTGGAGCGTTCCCTGTGGGCCTTGCTC*
AGAGCGGAGAAAGCATTTGTTTGTACAAGATCCGCAGACGTGTAAATGTT                Exon7
CCTGCAAAAACACAGACTCGCGTTGCAAGGCGAGGCAGCTTGAGTTAAAC
GAACGTACTTGCAGATGTGACAAGCCGAGGCGGTGAGCCGGGCAGGAGGA              *Exon8*
*AGGAGCCTCCCTCAGGGTTTCGG*

Fig. 1D

```
TCGCGGAGGCTTGGGGCAGCCGGGTAGCTCGGAGGTCGTGGCGCTGGGGG
CTAGCACCAGCGCTCTGTCGGGAGGCGCAGCGGTTAGGTGGACCGGTCAG
CGGACTCACCGGCCAGGGCGCTCGGTGCTGGAATTTGATATTCATTGATC
CGGGTTTTATCCCTCTTCTTTTTTCTTAAACATTTTTTTTTAAAACTGTA
TTGTTTCTCGTTTTAATTTATTTTTGCTTGCCATTCCCCACTTGAATCGG
GCCGACGGCTTGGGGAGATTGCTCTACTTCCCCAAATCACTGTGGATTTT
GGAAACCAGCAGAAAGAGGAAAGAGGTAGCAAGAGCTCCAGAGAGAAGTC
GAGGAAGAGAGAGACGGGGTCAGAGAGAGCGCGCGGGCGTGCGAGCAGCG
AAAGCGACAGGGGCAAAGTGAGTGACCTGCTTTGGGGGTGACCGCCGGA
GCGCGGCGTGAGCCCTCCCCCTTGGGATCCCGCAGCTGACCAGTCGCGCT
GACGGACAGACAGACAGACACCGCCCCAGCCCCAGCTACCACCTCCTCC
CCGGCCGGCGGCGGACAGTGGACGCGGCGGCGAGCCGCGGGCAGGGCCG
GAGCCCGCGCCCGGAGGCGGGGTGGAGGGGTCGGGCTCGCGGCGTCGC
ACTGAAACTTTTCGTCCAACTTCTGGGCTGTTCTCGCTTCGGAGGAGCCG
TGGTCCGCGCGGGGAAGCCGAGCCGAGCGGAGCCGCGAGAAGTGCTAGC
TCGGGCCGGGAGGAGCCGCAGCCGGAGGAGGGGGAGGAGGAAGAAGAGAA
GGAAGAGGAGAGGGGGCCGCAGTGGCGACTCGGCGCTCGGAAGCCGGGCT
CATGGACGGGTGAGGCGGCGGTGTGCGCAGACAGTGCTCCAGCCGCGCG
GCTCCCCAGGCCCTGGCCCGGGCCTCGGGCCGGGGAGGAAGAGTAGCTCG
CCGAGGCGCCGAGGAGAGCGGGCCGCCCCACAGCCCGAGCCGGAGAGGGA
GCGCGAGCCGCGCCGGCCCCGGTCGGGCCTCCGAAACCATGAACTTTCTG   Exon1
CTGTCTTGGGTGCATTGGAGCCTTGCCTTGCTGCTCTACCTCCACCATGC
CAAGTGGTCCCAGGCTGCACCCATGGCAGAAGGAGGAGGGCAGAATCATC   Exon2
ACGAAGTGGTGAAGTTCATGGATGTCTATCAGCGCAGCTACTGCCATCCA
ATCGAGACCCTGGTGGACATCTTCCAGGAGTACCCTGATGAGATCGAGTA
CATCTTCAAGCCATCCTGTGTGCCCCTGATGCGATGCGGGGGCTGCTGCA   Exon3
ATGACGAGGGCCTGGAGTGTGTGCCCACTGAGGAGTCCAACATCACCATG
CAGATTATGCGGATCAAACCTCACCAAGGCCAGCACATAGGAGAGATGAG   Exon4
CTTCCTACAGCACAACAAATGTGAATGCAGACCAAAGAAAGATAGAGCAA   Exon5
GACAAGAAAAAAATCAGTTCGAGGAAAGGGAAGGGGCAAAAACGAAAG    Exon6a
CGCAAGAAATCCCGGTATAAGTCCTGGAGCGTATGTGACAAGCCGAGGCG
GTGAGCCGGGCAGGAGGAAGGAGCCTCCCTCAGGGTTTCGG            Exon8
```

Fig. 1E

| | |
|---|---|
| TCGCGGAGGCTTGGGGCAGCCGGGTAGCTCGGAGGTCGTGGCGCTGGGGG | |
| CTAGCACCAGCGCTCTGTCGGGAGGCGCAGCGGTTAGGTGGACCGGTCAG | |
| CGGACTCACCGGCCAGGGCGCTCGGTGCTGGAATTTGATATTCATTGATC | |
| CGGGTTTTATCCCTCTTCTTTTTTCTTAAACATTTTTTTTAAAACTGTA | |
| TTGTTTCTCGTTTTAATTTATTTTTGCTTGCCATTCCCCACTTGAATCGG | |
| GCCGACGGCTTGGGGAGATTGCTCTACTTCCCCAAATCACTGTGGATTTT | |
| GGAAACCAGCAGAAAGAGGAAAGAGGTAGCAAGAGCTCCAGAGAGAAGTC | |
| GAGGAAGAGAGAGACGGGGTCAGAGAGAGCGCGCGGGCGTGCGAGCAGCG | |
| AAAGCGACAGGGGCAAAGTGAGTGACCTGCTTTTGGGGGTGACCGCCGGA | |
| GCGCGGCGTGAGCCCTCCCCCTTGGGATCCCGCAGCTGACCAGTCGCGCT | |
| GACGGACAGACAGACAGACACCGCCCCAGCCCCAGCTACCACCTCCTCC | |
| CCGGCCGGCGGCGGACAGTGGACGCGGCGGCGAGCCGCGGGCAGGGGCCG | |
| GAGCCCGCGCCCGGAGGCGGGGTGGAGGGGGTCGGGCTCGCGGCGTCGC | |
| ACTGAAACTTTTCGTCCAACTTCTGGGCTGTTCTCGCTTCGGAGGAGCCG | |
| TGGTCCGCGCGGGGAAGCCGAGCCGAGCGGAGCCGCGAGAAGTGCTAGC | |
| TCGGGCCGGGAGGAGCCGCAGCCGGAGGAGGGGGAGGAGGAAGAAGAGAA | |
| GGAAGAGGAGAGGGGGCCGCAGTGGCGACTCGGCGCTCGGAAGCCGGGCT | |
| CATGGACGGGTGAGGCGGCGGTGTGCGCAGACAGTGCTCCAGCCGCGCGC | |
| GCTCCCCAGGCCCTGGCCCGGGCCTCGGCCGGGGAGGAAGAGTAGCTCG | |
| CCGAGGCGCCGAGGAGAGCGGGCCGCCCACAGCCCGAGCCGGAGAGGGA | |
| GCGCGAGCCGCGCCGGCCCCGGTCGGGCCTCCGAAACCATGAACTTTCTG | Exon 1 |
| CTGTCTTGGGTGCATTGGAGCCTTGCCTTGCTGCTCTACCTCCACCATGC | |
| CAAG*TGGTCCCAGGCTGCACCCATGGCAGAAGGAGGAGGGCAGAATCATC* | Exon 2 |
| *ACGAAGTGGTGAAGTTCATGGATGTCTATCAGCGCAGCTACTGCCATCCA* | |
| *ATCGAGACCCTGGTGGACATCTTCCAGGAGTACCCTGATGAGATCGAGTA* | Exon 3 |
| *CATCTTCAAGCCATCCTGTGTGCCCCTGATGCGATGCGGGGGCTGCTGCA* | |
| *ATGACGAGGGCCTGGAGTGTGTGCCCACTGAGGAGTCCAACATCACCATG* | |
| *CAG<u>ATTATGCGGATCAAACCTCACCAAGGCCAGCACATAGGAGAGATGAG</u>* | Exon 4 |
| *<u>CTTCCTACAGCACAACAAATGTGAATGCAG</u>ACCAAAGAAAGATAGAGCAA* | Exon 5 |
| *GACAAGAAAAAAAATCAGTTCGAGGAAAGGGAAAGGGGCAAAAACGAAAG* | Exon 6a |
| *CGCAAGAAATCCCGGTATAAGTCCTGGAGCGTGTACGTTGGTGCCCGCTG* | Exon 6b |
| *CTGTCTAATGCCCTGGAGCCTCCCTGGCCCCATCCCTGTGGGCCTTGCT* | |
| *CAGAGCGGAGAAAGCATTTGTTTGTACAAGATCCGCAGACGTGTAAATGT* | Exon 7 |
| *TCCTGCAAAAACACAGACTCGCGTTGCAAGGCGAGGCAGCTTGAGTTAAA* | |
| *CGAACGTACTTGCAGATGTGACAAGCCGAGGCGG*TGAGCCGGGCAGGAGG | |
| AAGGAGCCTCCCTCAGGGTTTCGG | Exon 8 |

Fig. 1F

VEGF 121 / TBP

VEGF165/B2

VEGF165/TBP

METHOD FOR SELECTIVELY QUANTIFYING VEGF ISOFORMS IN A BIOLOGICAL SAMPLE AND USES THEREOF

CROSS-REFERENCE TO RELATED APPLICATIONS

The present application is a 35 U.S.C. §371 National Stage patent application of International patent application PCT/EP2005/007066, filed on Jun. 14, 2005, which claims priority to European patent application EP 04291485.3, filed on Jun. 14, 2004.

The present invention pertains to the field of diagnostic and prognostic of certain diseases, in particular cancers. More specifically, the present invention provides a novel method for quantifying, with a very high selectivity and sensitivity, the various isoforms of the vascular endothelial growth factor (VEGF), including the most soluble and potent ones.

Tumor angiogenesis has a key promoting role in growth and dissemination of solid tumors (Folkman 1997). Angiogenesis was more recently associated to the development of hematologic malignancies (Fiedler, Graeven et al. 1997; Perez-Atayde, Sallan et al. 1997; Aguayo, Kantarjian et al. 2000; Moehler, Ho et al. 2003), as several works described a bone marrow increased vascularisation in adults and children acute or chronic leukemias (Padro, Ruiz et al. 2000; de Bont, Fidler et al. 2002; Litwin, Leong et al. 2002; Padro, Bieker et al. 2002).

VEGF is one of the most potent proangiogenic factors. It exerts a variety of effects on vascular endothelial cells by interacting with its receptors VEGFR-1 (Flt-1) and VEGFR-2 (Flk-1/KDR). VEGF increases microvascular permeability, induces endothelial cell proliferation, survival and migration, promotes the balanced degradation of the extracellular matrix around the sprouting endothelium by inducing the expression of proteases (urokinase and tissue type plasminogen activators (uPA), plasminogen activator inhibitor-1 (PAI-1)) and interstitial collagenases (Dias, Shmelkov et al. 2002; Ferrara, Gerber et al. 2003). Leukemic cells, which express KDR, were shown to secrete VEGF and activate an autocrine growth stimulation loop, and a paracrine production of cytokines by the bone marrow microenvironment (Fiedler, Graeven et al. 1997).

The human VEGF gene, located on 6p21.3 chromosomic region, is organised as eight exons separated by seven introns (Wei, Popescu et al. 1996). Alternative exon splicing was initially shown to result in the generation of five main different isoforms: VEGF121, VEGF165, VEGF145, VEGF189 and VEGF206 (Vincenti, Cassano et al. 1996; Ferrara and Davis-Smyth 1997), having respectively 121, 165, 145, 189 and 206 amino acids after signal sequence cleavage. This alternative splicing is shown in FIG. 1A. Exons 6 and 7 encode two distinct heparin-binding domains. The presence or absence of these domains influences solubility and receptor binding. The heparin-binding domain encoded by exon 6 determines binding to the extracellular matrix. Isoforms containing the domain encoded by exon 6 (VEGF145, VEGF189 and VEGF206) are thus tightly bound to cell surface heparin-containing proteoglycans in the extracellular matrix (Poltorak, Cohen et al. 1997), whereas isoforms lacking the domain encoded by exon 6 are diffusible. VEGF 165, which contains only one heparin-binding region encoded by exon 7, is moderately diffusible, whereas VEGF 121, which lacks the domain encoded by exons 6 and 7, is highly diffusible.

Elevated cellular and circulating levels of total VEGF protein have been associated with poor prognosis in a variety of hematologic malignancies such as multiple myeloma (Di Raimondo, Azzaro et al. 2000), non-Hodgkin's lymphomas (Salven, Orpana et al. 2000) acute and chronic leukemias (Aguayo, Kantarjian et al. 2000). Aguayo et al. (Aguayo, Estey et al. 1999) showed that the plasma levels of VEGF protein were a bad prognostic indicator in newly diagnosed adult AML patients with elevated peripheral white blood cell counts (WBC).

In all these reports, cellular and/or circulating protein levels of VEGF were measured using enzyme-linked immunosorbent assay (ELISA) or radio immunoassay (RIA). These results remain therefore difficult to analyse since VEGF levels in cells and plasma reflect the various origins of this growth factor including platelets, and are restricted by the low sensitivity of the test.

The amounts of circulating VEGF protein and tumor VEGF protein have been found to correlate with poor prognosis in many types of solid tumors, including carcinomas of the breast, kidney, colon, brain, ovary, cervix, thyroid, bladder, esophagus, and prostate, as well as in osteoid and soft tissue sarcomas and pediatric tumors (Adams, Carder et al. 2000; Foekens, Peters et al. 2001; Tabone, Landman-Parker et al. 2001). In all these reports, the amount of VEGF (measured in different studies by immunohistochemistry, in situ hybridization, quantitative immunoassays, or Western blotting) correlated with one or more of the following prognostic measures: tumor size, metastasis, and shorter tumor-free and overall survival. However, none of the techniques described in these studies to quantitate tumor VEGF expression levels in solid tumors can be routinely performed, in particular due to the weak sensitivity of these methods (Dvorak 2002). Indeed, Konecny et al. using ELISA assays to measure $VEGF_{121-206}$ and $VEGF_{165-206}$ in primary breast tumor tissue lysates from 611 unselected patients (with a median clinical follow-up of 50 months), found that $VEGF_{121-206}$ and $VEGF_{165-206}$ were not detectable in 41.2% and 26% of the 611 primary tumors, respectively (Konecny, Meng et al. 2004). This is due to the weak sensitivity of both assays, which is not sufficient to detect very low levels of VEGF expression, and to the fact that these assays do not enable the specific detection of VEGF different isoforms. The other techniques described in the above-cited publications suffer from the same lack of sensitivity.

VEGF mRNA levels have also been found to correlate with vascular density and some histopathological features, such as tumor grade and vascular permeation in some (e.g., carcinomas of the cervix, breast, hepatocarcinomas) but not all cancers (Toi, Hoshina et al. 1994; Shen, Ghazizadeh et al. 2000; Van Trappen, Ryan et al. 2002; Jeng, Sheen et al. 2004). All these reports used semi-quantitative RT-PCR or quantitative RT-PCR to detect and measure total VEGF mRNA or VEGF isoform transcripts. However, no one described a highly sensitive assay detecting a few copies of VEGF transcripts (total and isoforms), nor accurate biological cut-off which is essential for robust and reproducible routine clinical test. And more important, no report showed any correlation between VEGF mRNA levels and disease-free survival and overall survival.

Hence, it appears that a selective and sensitive method for quantifying VEGF isoforms mRNAs is needed, in order to evaluate their value as prognostic and, if possible, therapeutic orientation tools. Moreover, for the isoforms eventually identified as valuable markers, this quantification method must be easy-to-perform, so that it can be used routinely by physicians.

Wellmann et al (Wellmann, Taube et al. 2001) have recently described a real-time RT-PCR assay for specific quantification of VEGF most abundant splice variants (VEGF121, VEGF165 and VEGF189). However, the detection threshold with the primer sets and the experimental protocols described by Wellmann et al is about 100 copies for VEGF121 or VEGF165 transcripts, and 1000 copies for VEGF189 transcript (see Example 1 below). The sensitivity of this assay hence remains insufficient for routinely performing reliable tests. Wellmann et al do not suggest that the level of any of the VEGF transcripts could be used as a prognosis and/or diagnosis marker.

The inventors have now developed highly sensitive and selective tests based on the Q-RT-PCR technology (Quantitative Reverse Transcription-Polymerase Chain Reaction), which enable the detection of 10 (VEGF 189, VEGF 145, VEGF206) or even one single (VEGF121 and VEGF165) transcript copies in a biological sample, whereas no amplification occurs in the absence of said transcripts.

These tests were applied to assess the value of the VEGF isoforms transcripts level as prognostic markers in various cancers, including acute myeloid leukaemia, breast, prostate, and colon cancers, and angioimmunoblastic T-cell lymphoma (AITL).

The inventors have hence demonstrated that a high level of certain VEGF isoforms is indicative of a poor prognosis in acute myeloid leukaemia (VEGF121 and VEGF165 isoforms) with an accurate cut-off for both isoforms, as well as in solid tumors including breast cancer (VEGF165 isoform, whereas high level of VEGF121 is surprisingly indicative of a good prognosis) (see examples 4 and 5). Most importantly, the inventors have demonstrated that an elevated VEGF165/VEGF121 ratio is a strong indicator of a bad prognosis (with a biological cut-off of R=3). The inventors have also demonstrated that a high level of VEGF121, VEGF165 and VEGF189 isoforms is indicative of progression in lymphoma (Zhao, Mourah et al. 2004).

Advantageously, the methods for selectively quantifying VEGF21, VEGF165, VEGF145, VEGF189 and VEGF206 transcripts enable reliable and easy VEGF determination to be performed routinely in research and medicine laboratories.

The high sensitivity and selectivity performances of these methods are due to the choice of the primers and the probes used for the amplification/detection phase. The inventors have indeed determined precise conditions that enable such very high sensitivity and specificity: (i) the first primer preferably hybridizes to part of exon 4; (ii) the size of the amplified product must be inferior to 150 bp, preferably in the range 70-150 bp; (iii) the second primer must have a sequence that spans a junction between two exons, wherein said junction is specific for the transcript to be quantified; when it is not feasible to design such a primer having regard to the above constraint in item (ii), then the probe spans such a specific junction. The inventors have designed primers and probes which fulfil the above conditions, for each isoform: for VEGF121, the second primer spans exons 5 and 8 (this primer preferably have a C or a G at its 3' extremity); for VEGF165, the probe spans exons 5 and 7; for VEGF189, the second primer spans exons 6a and 7; for VEGF145, the second primer spans exons 6a and 8; and for VEGF206, the second primer spans exons 6a and 6b.

To further increase the detection performances, the probe used for real-time quantification of the amplified target sequence preferably hybridizes to another junction between two exons. For example, the probe for selectively quantifying VEGF121 spans exons 4 and 5, and the probe for selectively quantifying VEGF189 or VEGF206 spans exons 5 and 6a.

A first aspect of the present invention is hence a method for selectively quantifying VEGF transcripts selected amongst VEGF165, VEGF121, VEGF189, VEGF145 and VEGF206 in a biological sample, comprising a step of performing a real-time quantitative reverse transcription-polymerase chain reaction (QRT-PCR), wherein the first primer used for amplification comprises at least 15 consecutive nucleotides from exon 4 or its complementary sequence, and wherein the second primer and/or the probe are as follows:

for quantifying VEGF165 transcripts, the second primer comprises at least 15 consecutive nucleotides from exon 7 or its complementary sequence, and the probe spans the junction between exons 5 and 7 and comprises at least the sequence 5'-gAAAATCCCTg-3' (SEQ ID No: 19) or its complementary sequence;

for quantifying VEGF121 transcripts, the second primer spans the junction between exons 5 and 8 and comprises at least the sequence 5'-GAAAAATGTGAC-3' (SEQ ID No:8) or its complementary sequence;

for quantifying VEGF189 transcripts, the second primer spans the junction between exons 6a and 7 and comprises at least the sequence 5'-CAgggAACgC-3' (SEQ ID No:20) or its complementary sequence;

for quantifying VEGF145 transcripts, the second primer spans the junction between exons 6a and 8 and comprises at least the sequence 5'-CACATACgC-3' (SEQ ID No:21) or its complementary sequence;

for quantifying VEGF206 transcripts, the second primer spans the junction between exons 6a and 6b and comprises at least the sequence 5'-CgTACACgC-3' (SEQ ID No:22) or its complementary sequence.

Of course, the exons cited here are those of VEGF mRNA, see FIG. 1. Also self-evident for the skilled artisan is the fact that the pair of primers is chosen in order to enable amplification of a fragment (i.e., one forward primer and one reverse primer), and that a probe can hybridize to either of the DNA strands. Hence, in what follows, the phrase "or its complementary sequence" will not be repeated, but is implicitly meant.

Preferably, the primer hybridizing to exon 4 is a forward primer, and the other primer (for example, the primer hybridizing to the junction between exons 5 and 8 for amplifying VEGF121) is a reverse primer.

According to the present invention, the primers comprise at least 15 nucleotides, and preferably from 18 to 23 nucleotides. For example, a preferred reverse primer for specifically amplifying VEGF121 according to the above method is 5'-CTCGGCTTGTCACATTTTTC-3' (SEQ ID No: 2).

Preferred pairs of primers for performing the above method according to the invention are as follows:

for quantifying VEGF165 transcripts:

```
forward primer 146F (exon 4):
5'-GAGCTTCCTACAGCACAACAAA-3',      (SEQ ID No: 3)
and reverse primer (exon 7)
5'-GCTTTCTCCGCTCTGAGCA-3';          (SEQ ID No: 9)
``` for quantifying VEGF121 transcripts:

```
(pair 125F-223R):
forward primer 125F (exon 4):
5'-AGGCCAGCACATAGGAGAGAT-3',        (SEQ ID No: 1)
and reverse primer 223R (exon 5/8):
5'-CTGGGCTTGTCACATTTTTC-3';         (SEQ ID No: 2)
```

-continued

```
(pair 146F-223R):
forward primer 146F (exon 4):
5'-GAGCTTCCTACAGCACAACAAA-3',      (SEQ ID No: 3)
and reverse primer 223R (exon 5/8):
5'-CTCGGCTTGTCACATTTTTC-3';        (SEQ ID No: 2)
``` for quantifying VEGF189 transcripts:

```
forward primer 146F (exon 4):
5'-GAGCTTCCTACAGCACAAGAAA-3',      (SEQ ID No: 3)
and reverse primer (exon 6a/7):
5'-CCACAGGGAACGCTCCAGGAC-3';       (SEQ ID No: 13)
``` for quantifying VEGF145 transcripts:

```
forward primer 146F (exon 4):
5'-GAGCTTCCTACAGCACAACAAA-3',      (SEQ ID No: 3)
and reverse primer (exon 6a/8):
5'-CTTGTCACATACGGTCCAGGAC-3';      (SEQ ID No: 11)
``` for quantifying VEGF206 transcripts:

```
    forward primer 146F (exon 4):
    5'-GAGCTTCCTACAGCACAACAAA-3',  (SEQ ID No: 3)
    and reverse primer (exon 6a/6b):
    5'-CACCAACGTACACGCTCCAGG-3'.   (SEQ ID No: 15)
```

When performing the method according to the invention, it is preferred that for at least one of the isoforms, the pair of primers used for the specific amplification of the mRNA encoding said isoform is selected amongst the pairs of primers listed above.

In order to perform the method of the invention, the skilled artisan is able to modify the sequences of the above-described primers by addition and/or deletion of one or a few nucleotide(s) at the 3' and/or 5' extremity, especially addition of nucleotides at the 5' extremity of a primer. Of course, a method as described herein, in which one or several of the oligonucleotides used are derived from the sequences of SEQ ID Nos 1, 2, 3, 9, 11, 13, and/or 15 in such a way, is also part of the present invention.

In a preferred embodiment of the method for quantifying one or several VEGF isoforms transcripts according to the invention, the probe used for real-time quantification of at least one of said transcripts is as follows:

for quantifying VEGF121 transcripts: the probe preferably spans the junction between exons 4 and 5. For example, it can comprise at least the sequence 5'-CAGACC-3';

for quantifying VEGF189 and/or VEGF206 transcripts: the probe preferably spans the junction between exons 5 and 6a and comprises at least the sequence 5'-AAAAAA-3'.

for quantifying VEGF145 transcripts: the probe preferably comprises at least 15 consecutive nucleotides from exon 6a the amplified product.

The size of the probe(s) is preferably in the range 20-50 nucleotides, and preferably 25-35 nucleotides.

The following probes can advantageously be used:
for quantifying VEGF 165 transcripts:

```
5'-AGCAAGACAAGAAAATCCCTGTGGGCC-3';  (SEQ ID No: 10)
``` for quantifying VEGF121 transcripts:

```
5'-TGCAGACCAAAGAAAGATAGAGCAAGACA-3';  (SEQ ID No: 4)
``` for quantifying VEGF189 and/or VEGF206 transcripts:

```
                                       (SEQ ID No: 14)
5'-AGCAAGACAAGAAAAAAAATCAGTTCGAGGAAA-3';
``` for quantifying VEGF 145 transcripts:

```
5'-AAACGAAAGCGCAAGAAATCCCGGTA-3'.  (SEQ ID No: 12)
```

Alternatively, for any of the isoforms to be quantified, a sequence complementary to the above-described appropriate sequence can also be used as a probe, as well as any sequence derived therefrom by addition and/or deletion of one or a few nucleotide(s) at 5' and/or 3' extremity.

The probe is preferably labelled. Several probe systems have been described for specifically measuring amplification of a target sequence. They are usually constituted of an oligonucleotide complementary to said target sequence, which is bonded to pairs of fluorophore groups or fluorophore/quenchers, such that hybridisation of the probe to its target and the successive amplification cycles cause an increase or reduction in the total fluorescence of the mixture, depending on the case, proportional to the amplification of the target sequence.

Non limitative examples of labelling systems that can be used to carry out kinetic PCR are the TaqMan™ (ABI®), the AmpliSensor™ (InGen), and the Sunrise™ (Oncor®, Appligene®) systems. The skilled artisan can chose amongst these systems or other systems.

Apart from the primers and probe sequence, specified as above, the skilled artisan can use his general knowledge concerning quantitative RT-PCR in order to determine the other parameters for performing the method according to the invention (for example, cycling parameters, quantification having regard to a housekeeping gene, etc.). Examples of such parameters are given in the experimental results below.

As shown in example 1, the above primers and probe, combined to the skilled artisan's basic knowledge, have led to a quantification of VEGF121 transcripts in a biological sample with sensitivity and selectivity levels that are considerably higher than what had been described previously.

In particular, the inventors have performed the reverse transcription step with a reverse transcriptase and random hexamers. In their protocol, 0.2 unit of Uracyl DNA glycosylase was added in each PCR vial, in order to avoid any contamination and possible detection of false positives.

Figure 4:
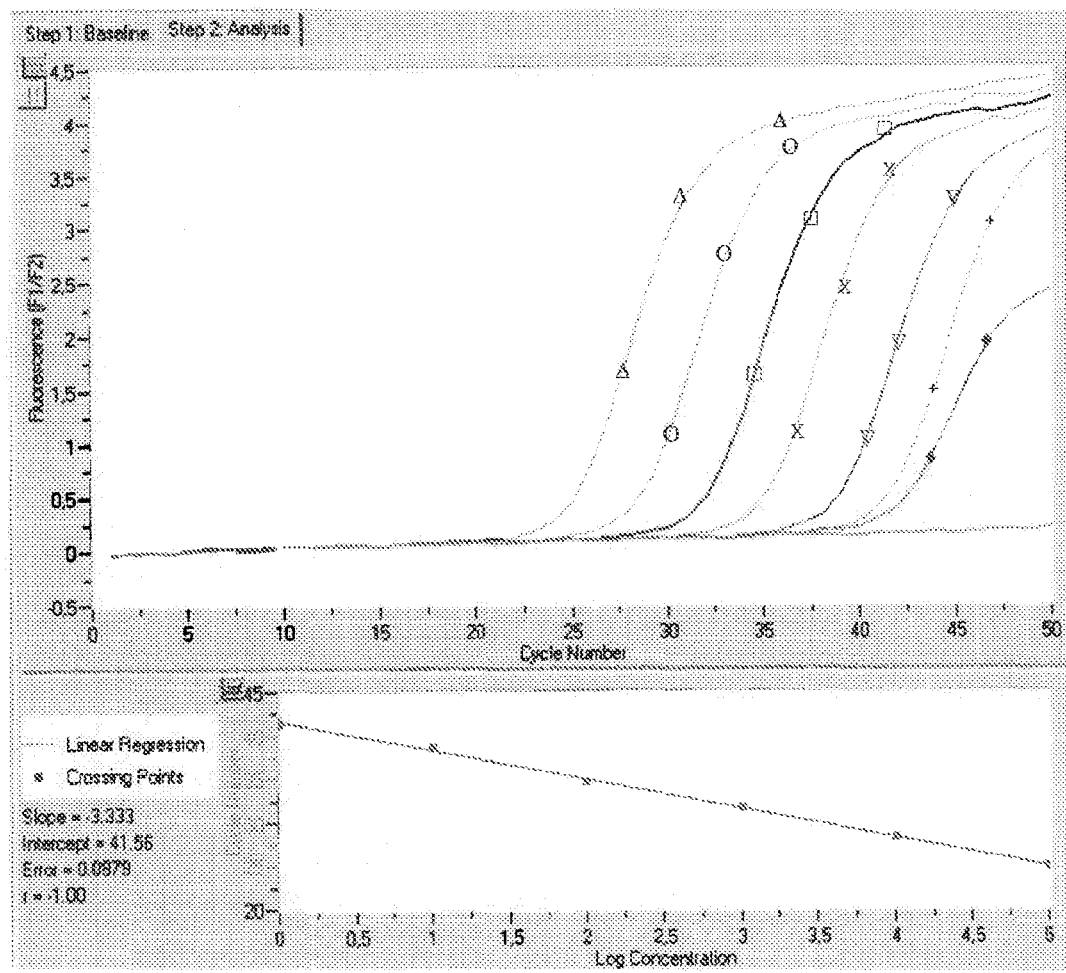
Figure 5:
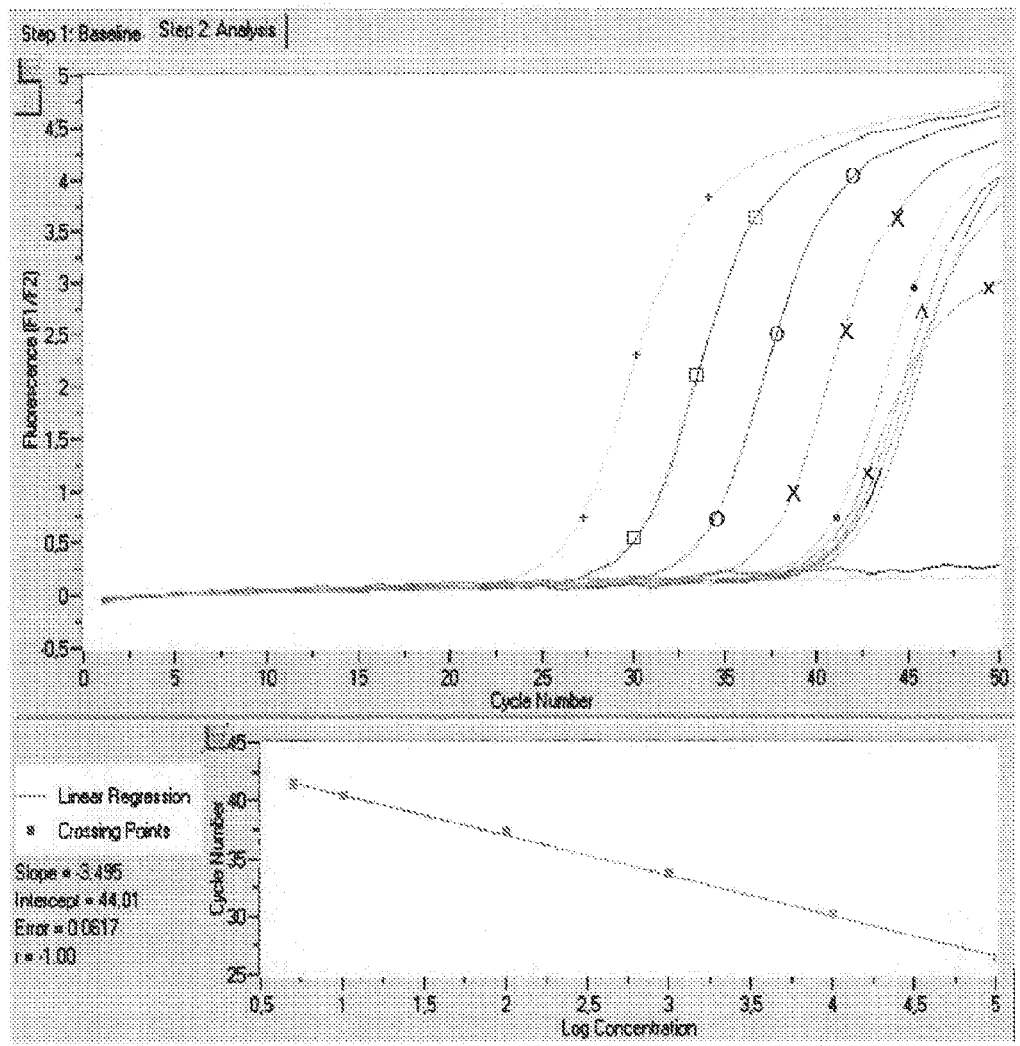

By doing so, they have obtained the following results:
with the pair of primers 125F-223R (SEQ ID Nos: 1 and 2), the calibration curve is in the range $10^9$ copies to one copy. The PCR efficiency is 100%, with a slope of 3.333, as shown in FIG. 4. This excellent result shows the exceptionally high sensitivity of the method.

with the pair of primers 146F-223R (SEQ ID Nos: 3 and 2), the calibration curve is in the range $10^9$ copies to 5 copies. The PCR efficiency is 94%, with a slope of 3.495, as shown in FIG. 5. This also corresponds to an excellent sensitivity.

Calibration experiments described in example 2 further show that the sets of primers and probes according to the invention enable the detection of 10 (VEGF189, VEGF145, VEGF206) or even one single (VEGF121 and VEGF165) copy of said isoforms.

According to another embodiment of the method according to the invention, multiplex quantitative RT-PCRs are performed in order to quantify the transcripts of two or more VEGF isoforms (or at least one VEGF isoform and at least one housekeeping gene) in the same tube. As shown in example 3 below, such methods retain the specificity and sensibility properties observed when simplex Q-RT-PCRs are performed.

Another aspect of the invention pertains to diagnostic and/or prognosis and/or therapeutic orientation methods based on the measurement of specific VEGF isoform(s) expression level, for example VEGF121 expression level, in biological samples.

Indeed, the inventors have demonstrated that a high level of VEGF121 transcripts in peripheral blood mononuclear cells (PBMC) from acute myeloid leukaemia (AML) patients correlated with a poor prognosis (see Example 4 below). When adjusted to other known prognostic parameters of AML, VEGF165 and VEGF189 are also good prognostic indicators of event free survival and overall survival (see example 5). Most importantly, the inventors have also demonstrated that the VEGF165/VEGF121 expression ratio is a very strong prognosis indicator in solid tumors cancers, especially breast cancers (example 5): an elevated VEGF165/VEGF121 ratio (especially, higher than the biological cut-off of R=3) is indicative of a poor prognosis, and can also inform the physician about the urgent need of said patient for an antiangiogenesis treatment. The present invention hence also concerns a method for accurately selecting patients for antiangiogenic treatments.

Besides, angiogenesis is also implicated in other diseases such as diabetes and cardiovascular diseases.

The invention therefore advantageously pertains to the use of a method for measuring the level of at least one VEGF isoform transcripts in a biological sample according to the invention, for establishing a diagnostic and/or a prognosis concerning a patient potentially suffering from a disease related to angiogenesis. Such disease include, but are nor limited to cancers—including carcinomas of the breast, kidney, colon, brain, ovary, cervix, thyroid, bladder, esophagus and prostate, osteoid and soft tissue sarcomas, pediatric tumors and hematologic malignancies—diabetes, and cardiovascular diseases. VEGF isoforms the transcripts of which will be preferably measured according to this aspect of the invention are VEGF121, VEGF165, and (to a lesser extent) VEGF189.

In this aspect of the invention, the biological sample can be a tumor or normal tissue. It can also be taken from a body fluid, such as urines, saliva, bone marrow, blood, and derivative blood products (sera, plasma, PBMC, circulating cells, circulating RNA).

Another aspect of the present invention is a method for establishing a diagnostic and/or a prognosis concerning a patient potentially suffering from cancer, hemopathy, diabetes, or cardiovascular disease, comprising a step of determining the level of expression of at least one VEGF isoform, especially the VEGF121 and/or VEGF165 and/or VEGF189 isoform(s) in a biological sample from said patient. In particular, the level of expression of the VEGF isoform(s) can be determined by measuring the level of said VEGF isoform(s) transcripts in the biological sample by QRT-PCR, through a method as described above. The physician, or a well-trained technician, will then compare said measured level to the normal level of said VEGF isoform(s) transcripts in healthy subjects and/or in non-tumorigenic tissues from said patient.

The invention especially concerns a method for in vitro establishing a prognosis for a patient suffering from acute myeloid leukaemia, comprising the following steps:
isolating peripheral blood mononucleated cells from a blood sample from said patient;
extracting RNA from said peripheral blood mononucleated cells; and
measuring the level of VEGF121 transcript in said peripheral blood mononucleated cells, by a method according to the invention. VEGF 165 and/or VEGF189 transcripts levels can also be measured in this context.

A further step of comparing said level of VEGF isoform(s) transcripts to the normal level of said transcripts in healthy subjects is then performed by a physician or a trained technician.

Indeed, it has been shown that an elevated cellular and circulating level of total VEGF protein is associated with poor prognosis in a variety of hematologic malignancies such as multiple myeloma (Di Raimondo, Azzaro et al. 2000), non-Hodgkin's lymphomas (Salven, Orpana et al. 2000) acute and chronic leukemias (Aguayo, Kantarjian et al. 2000). Aguayo et al. (Aguayo, Estey et al. 1999) showed that the plasma levels of VEGF protein were a bad prognostic indicator in newly diagnosed adult AML patients with elevated peripheral white blood cell counts (WBC). VEGF121 and VEGF165, which are the most soluble and potent isoforms of VEGF, probably play the most important part in these observations. As a confirmation of this, the inventors have demonstrated that an elevated level of VEGF121 and/or VEGF165 transcripts is indicative of a poor prognosis in acute myeloid leukemias (see examples 4 and 5 below). The inventors have shown that the VEGF121 transcripts mean level in AML patients samples is at least 10 times higher than the average level observed in healthy subjects. In AML patients, ratio of $VEGF121/10^4$ copies of $\beta 2m$ superior to 5 ($25^{th}$ percentiles), and/or ratio of $VEGF165/10^6$ of $\beta 2 m$ superior to 229 ($67^{th}$ percentiles) are significantly associated to a worse prognosis.

The methods according to the invention can hence comprise a further step of comparing the measured VEGF121 transcripts to the average level observed in healthy subjects. In this step, preferably done by a physician, an observed VEGF121 level 2-fold higher than the average level observed in healthy subjects, will be indicative of a poor prognosis, especially in the case of cancers such as solid tumors and malignant hemopathies. Observed levels 5-fold, or even 10-fold higher than the average level observed in healthy subjects are of course even more relevant for establishing a poor prognosis.

Another important aspect of the present invention is a method for in vitro establishing a prognosis concerning a patient having a solid tumor, comprising a step of measuring the level of VEGF121 and VEGF165 transcripts in a biopsy from said tumor, and calculating the VEGF165/VEGF121 ratio. In particular, this method can be used for establishing a prognosis concerning a patient suffering from breast cancer. Indeed, the inventors have clearly demonstrated that high levels of VEGF121 transcripts were related to a good prognosis, while high VEGF165 transcripts levels were associated to a bad prognosis in breast cancers. As a consequence and most importantly, VEGF165/VEGF121 elevated ratio is strongly associated with a bad prognosis (see example 5 below). Especially, a VEGF165/VEGF121 superior or equal to 3 is strongly indicative of a bad prognosis. Of course, in the prognosis methods mentioned above, the measure of VEGF isoforms levels can be performed by a QRT-PCR method using the primers and probed as described herein.

As further detailed below, the levels of VEGF isoforms transcripts can be expressed as a ratio to the level of a housekeeping gene transcript.

The method for selectively quantifying VEGF isoforms transcripts in a biological sample, according to the present invention, is a particularly interesting tool for physicians treating patients suffering from any pathology potentially necessitating an antiangiogenic treatment. For example, clinical studies with VEGF inhibitors or agents blocking its transduction appear to be promising in leukemias. In a phase II study of SU5416 (VEGF tyrosine kinase inhibitor) conducted on AML patients resistant to standard chemotherapy, Fiedler et al. observed clinical response in 19% (⅜₄₃) of cases (Fiedler, Mesters et al. 2003). Besides, in phase III clinical trials on colorectal cancer bevacizumab, a humanized anti-VEGF antibody (Avastin) revealed a good efficacy. Monitoring of antiangiogenic treatment through QRT-PCR of at least one of VEGF isoforms (especially, VEGF121 and/or VEGF165 and/or VEGF189) could therefore help treating these patients.

The present invention hence also pertains to the use of a method for selectively quantifying transcripts encoding VEGF isoforms selected amongst VEGF165, VEGF121, VEGF189, VEGF145 and VEGF206 in a biological sample, as described above, for monitoring the antiangiogenic treatment of a patient, and/or orientating the treatment regimen of a patient suffering from cancer. For this application, VEGF121 and/or VEGF165 transcripts levels are preferably quantified.

The method for selectively quantifying transcripts encoding VEGF isoforms in a biological sample according to the invention can also be used for obtaining information useful for orientating the treatment regimen of a patient suffering from cancer. For example, a VEGF165/VEGF121 ration superior to 3 in a sample from a breast tumor indicates that the patient needs an antiangiogenic treatment. Accordingly, another aspect of the invention is a method for orientating the treatment regimen of a patient having a solid tumor, especially a breast tumor, comprising the following steps:
measuring the level of VEGF121 and VEGF165 transcripts in a biopsy from said tumor;
calculating the VEGF165/VEGF121 ratio; and
prescribing an antiangiogenic treatment if the VEGF165/VEGF121 ratio is superior to 3 (or even superior to 2, although said prescription is even more justified if the ratio is >3).

According to another of its aspects, the present invention also concerns a set of oligonucleotides for performing any of the above methods, comprising at least one of the following pairs of primers:

pair of primers specific for VEGF165:

```
5'-GAGCTTCCTACAGCACAACAAA-3'    (SEQ ID No: 3)
and

5'-GCTTTCTCCGCTCTGAGCA-3';      (SEQ ID No: 9)
``` pairs of primers specific for VEGF121:

```
  5'-CTCGGCTTGTCACATTTTTC-3'    (SEQ ID No: 2)
  coupled to either

5'-AGGCCAGCACATAGGAGAGAT-3'   (SEQ ID No: 1)
  or
```

```
  5'-GAGCTTCCTACAGCACAACAAA-3'; (SEQ ID No: 3)
``` pair of primers specific for VEGF189:

```
5'-GAGCTTCCTACAGCACAACAAA-3'    (SEQ ID No: 3)
and

5'-CCACAGGGAACGCTCCAGGAC-3';    (SEQ ID No: 13)
``` pair of primers specific for VEGF145:

```
5'-GAGCTTCCTACAGCACAACAAA-3'    (SEQ ID No: 3)
and

5'-CTTGTCACATACGCTCCAGGAC-3';   (SEQ ID No: 11)
``` pair of primers specific for VEGF206:

```
5'-GAGCTTCCTACAGCACAACAAA-3'    (SEQ ID No: 3)
and

5'-CACCAACGTACACGCTCCAGG-3'.    (SEQ ID No: 15)
```

A particular set of primers comprises the following pair of primers specific for VEGF121:

```
125F:  5'-AGGCCAGCACATAGGAGAGAT-3'; (SEQ ID No: 1)
and

223R:  5'-CTCGGCTTGTCACATTTTTC-3'.  (SEQ ID No: 2)
```

Alternatively, the set of oligonucleotides according to the invention comprises at least the following pair of primers specific for VEGF 121:

```
146F:
5'-GAGCTTCCTACAGCACAACAAA-3';   (SEQ ID No: 3)
and

223R:
5'-CTCGGCTTGTCACATTTTTC-3'.     (SEQ ID No: 2)
```

In a preferred embodiment of the sets of oligonucleotides comprising a pair of primers specific for VEGF121, as described above, said sets also comprise a probe targeting the junction of exons 4 and 5 of VEGF mRNA. Advantageously, this probe spans the junction between exons 4 and 5 and comprises at least the sequence 5'-CAGACC-3' or its complementary sequence. For example, the nucleotide sequence of said probe is 5'-TGCAGACCAAAGAAAGATAGAGCAA-GACA-3' (SEQ ID No: 4).

In another preferred embodiment of the sets of oligonucleotides according to the invention, said sets comprise the pair of primers of SEQ ID Nos: 3 and 9, specific for VEGF165. Such sets of oligonucleotides preferably further comprise a probe spanning the junction of exons 5 and 7 of VEGF mRNA, wherein said probe comprises at least the sequence 5'-AAATCC-3'. For example, this probe can be 5'-AGCAA-GACAAGAAAATCCCTGTGGGCC-3' (SEQ ID No: 10).

When quantifying VEGF isoforms transcripts by RT-PCR, according to the present invention, the result is preferably expressed as a relative expression of said VEGF isoform, having regard to at least one gene with a constant expression level, for example a housekeeping gene. In order to facilitate the operator's task, the set of primers and probe according to the invention can also further comprise a pair of primers and a probe specific for a human housekeeping gene.

An example of pair of primers and a probe specific for a human housekeeping gene that can be included in a set of oligonucleotides according to the invention is specific for β2 microglobulin and is as follows:

```
                                          (SEQ ID No: 5)
β2m forward:
5'-CGCTCCGTGGCCTTAGC-3';

(SEQ ID No: 6)
β2m reverse:
5'-GAGTACGCTGGATAGCCTCCA-3';
and (SEQ ID No: 7)
β2m probe:
5'-FAM-TGCTCGCGCTACTCTCTCTTTCTGGC-3'-TAMRA.
```

Another example of pair of primers and a probe specific for a human housekeeping gene that can be included in a set of oligonucleotides according to the invention is specific for the TATAbox-binding protein (TBP) and is as follows:

```
                                          (SEQ ID No: 16)
TBP forward:
5'-CACGAACCACGGCACTGATT-3';

(SEQ ID No: 17)
TBP reverse:
5'-TTTTCTTGCTGCCAGTCTGGAC-3';
and (SEQ ID No: 18)
TBP probe:
5'-FAM-TGTCGACAGGAGCCAAGATTTCTGGC-3'-TAMRA.
```

Other housekeeping genes, such as PPIA, GAPDH, PBGD, HPRT, etc., can also be used therefore.

In the above sets of oligonucleotides, the probe(s) are preferably labeled, so that they are ready-to-use for real-time QPCR amplification measurement.

Another embodiment of the invention is a kit comprising at least part of the reagents that are needed for a technician to perform the quantification of VEGF121 transcripts by routine kinetic QRT-PCR, from a biological sample. Such a kit according to the invention comprises at least a set of primers and probe specific for at least one VEGF isoform transcript (for example, VEGF121), as described above, and a determined amount of DNA for the preparation of said VEGF isoform transcript standard, wherein said DNA comprises at least the sequence encoding said VEGF isoform which is amplified by the pair of primers specific for it.

For example, the DNA for the preparation of a VEGF121 standard comprises the whole sequence of VEGF121 cDNA.

In a particular embodiment of this kit, the determined amount of DNA for the preparation of a VEGF121 standard is lyophilized. A notice, comprised in the kit, can indicate to the skilled artisan how to prepare the standard, for example by suspending the lyophilized DNA in a precise volume of water, and then performing serial dilutions. Alternatively, the DNA for the preparation of the standard can be in the form of a solution of given concentration.

The kit according to the invention can also comprise a pair of primers and a probe specific for a calibration gene (typically, a housekeeping gene); in this case, the kit preferably also comprises a determined amount of DNA for the preparation of a standard for said gene.

In another embodiment of the kit according to the invention, reagents for performing the RT-PCR reaction are also comprised. Such reagents can be, for example, reagents for the RT step, like random hexamers and/or reverse transcriptase. Reagents for the PCR step, such as dNTPs, $MgCl_2$, a polymerase, a PCR buffer, Uracyl DNA glycosylase, etc., can also be included in the kit.

In an even more complete embodiment of the kit according to the invention, reagents for RNA extraction, for example Trizol reagent or equivalent, are also included.

The following experimental examples and figures further illustrate the present invention.

LEGEND TO THE FIGURES

FIG. 1: FIG. 1A: map of the various VEGF isoforms. FIG. 1B to 1F: nucleotide sequences encoding VEGF isoforms, deduced from the sequence of total VEGF (NM003376). Respectively: sequences encoding VEGF165 (SEQ ID No: 23), VEGF121 (SEQ ID No: 24), VEGF189 (SEQ ID No: 25), VEGF145 (SEQ ID No: 26), and VEGF206 (SEQ ID No: 27). The start and stop codons are indicated in bold, and the regions to which primers and probes according to the invention hybridize are underlined.

Figure 2:
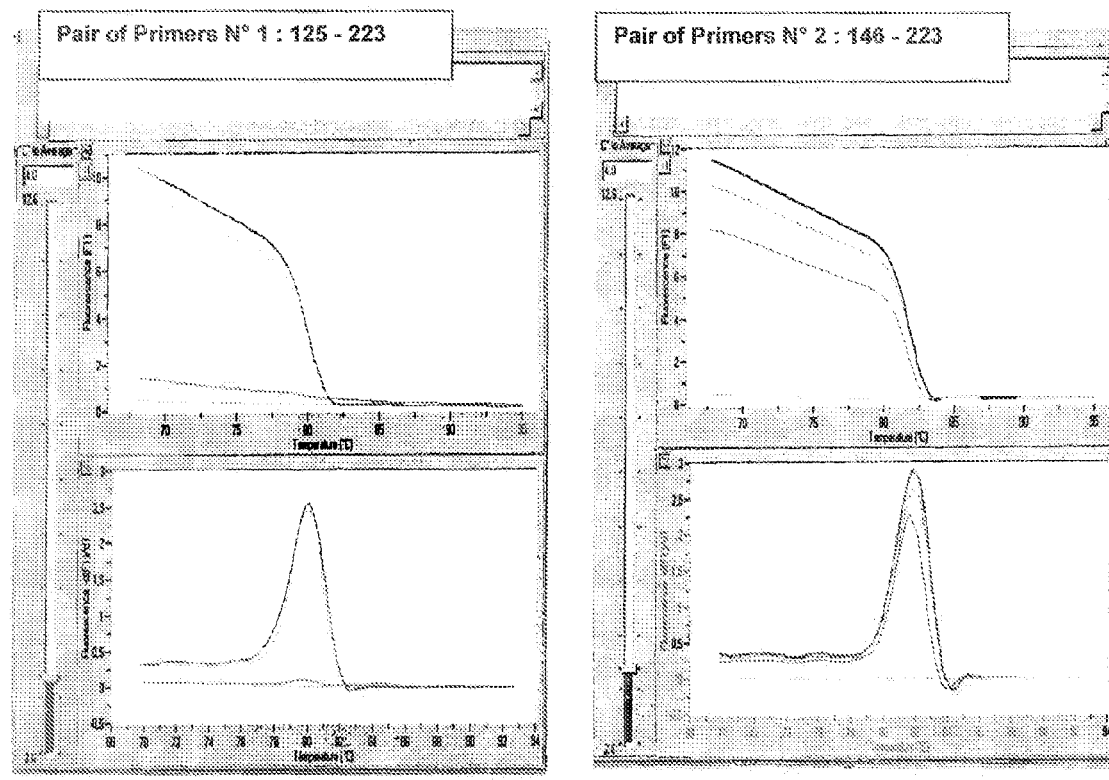

FIG. 2: Test of the amplification with the primer sets. The amplification product is labelled with SybrGreen.

Figure 3:
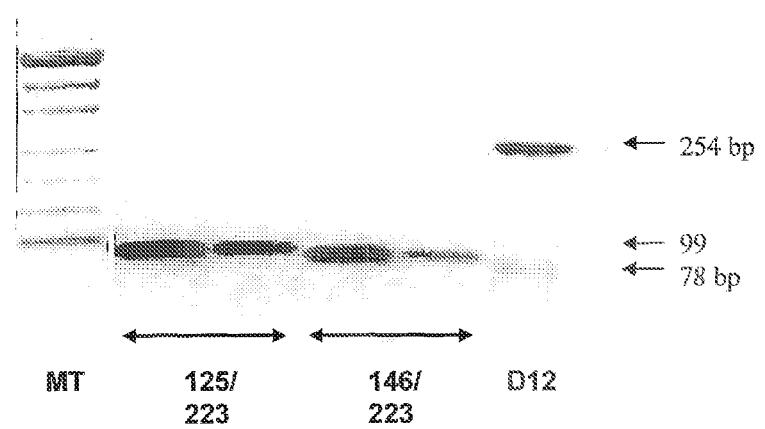

FIG. 3: Size analysis of the products amplified with three different primer sets.

MT: size marker

125/223: amplification with primers of SEQ ID NO:1 and SEQ ID NO: 2.

146/223: amplification with primers of SEQ ID NO: 3 and SEQ ID NO: 2.

D12: amplification with the primers disclosed by Wellmann et al (Wellmann, Taube et al. 2001).

FIG. 4: standard curve using primers of SEQ ID NO:1 and SEQ ID NO: 2. The curve comprises points in the range 1 to $10^9$ copies. Only the most sensitive part is shown here. The PCR efficiency is 100%, with a slope of 3.333.

Points of the curve:
1-5 $10^5$ copies
1-4 $10^4$ copies
1-3 $10^3$ copies
1-2 $10^2$ copies
1-1 10 copies
1 1 copy
Repli. 1 replicate of one copy FIG. 5: standard curve using primers of SEQ ID NO:3 and SEQ ID NO: 2. The curve comprises points in the range 5 to $10^9$ copies. Only the most sensitive part is shown here. The PCR efficiency is 94%, with a slope of 3.495.

Points of the Curve:

| 1-5 | $10^5$ copies |
|---|---|
| 1-4 | $10^4$ copies |
| 1-3 | $10^3$ copies |
| 1-2 | $10^2$ copies |
| 1-1 | 10 copies |
| 5 copies | 5 copies |
| 5 copies | 5 copies |
| Repli. 1-1 | replicate of 10 copies |

Ech 10 sample of very low concentration, run as unknown. It is measured as 4 copies.

FIG. 6: standard curves using primers described by Wellmann et al (Wellmann, Taube et al. 2001). The standard curves correspond to the selected point (shaded).

Figure 6A:
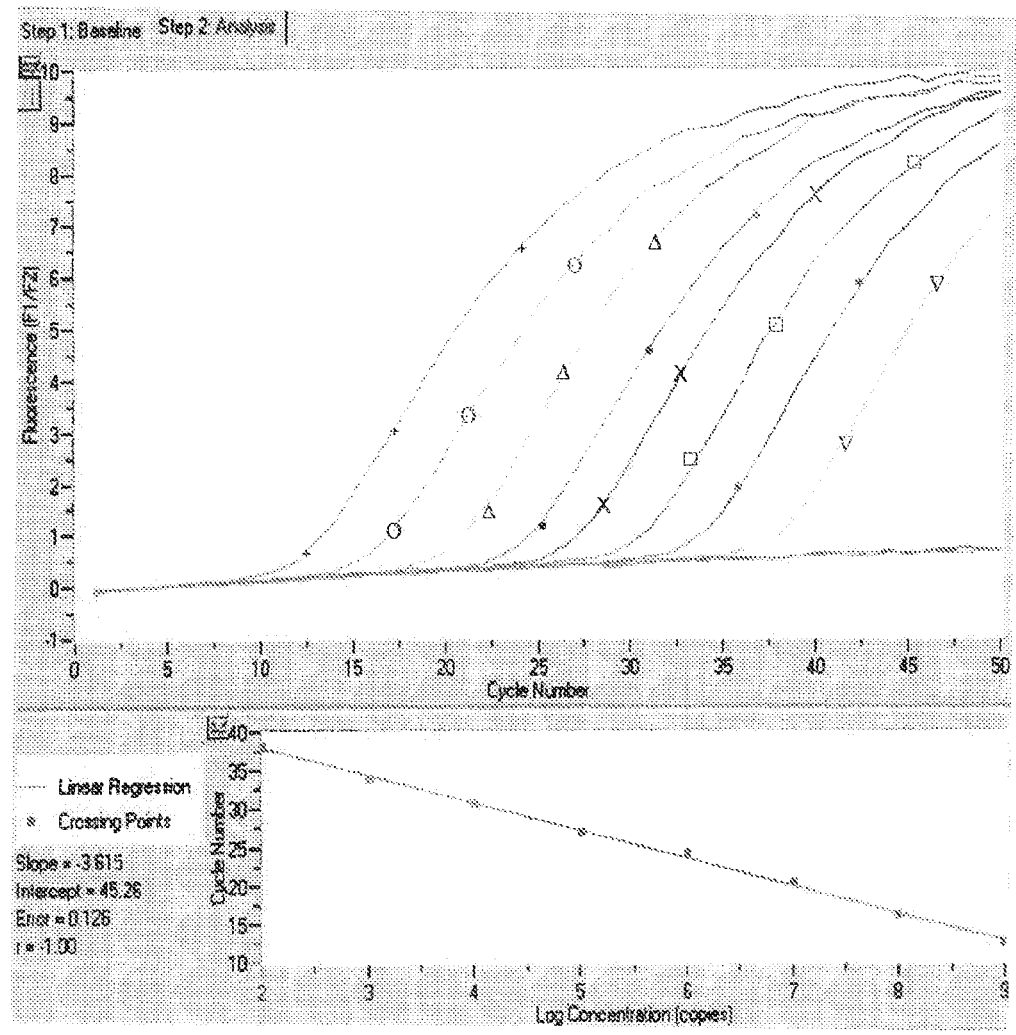

FIG. 6A: The curve is done using the same experimental conditions as Wellmann et al (Wellmann, Taube et al. 2001).

Points of the curve: V9, $10^9$ copies; V8, $10^8$ copies; V7, $10^7$ copies; V6, $10^6$ copies; V5, $10^5$ copies; V4, $10^4$ copies; V3, $10^3$ copies; V2, $10^2$ copies; V1, 10 copies; V1c, one copy.

Figure 6B:
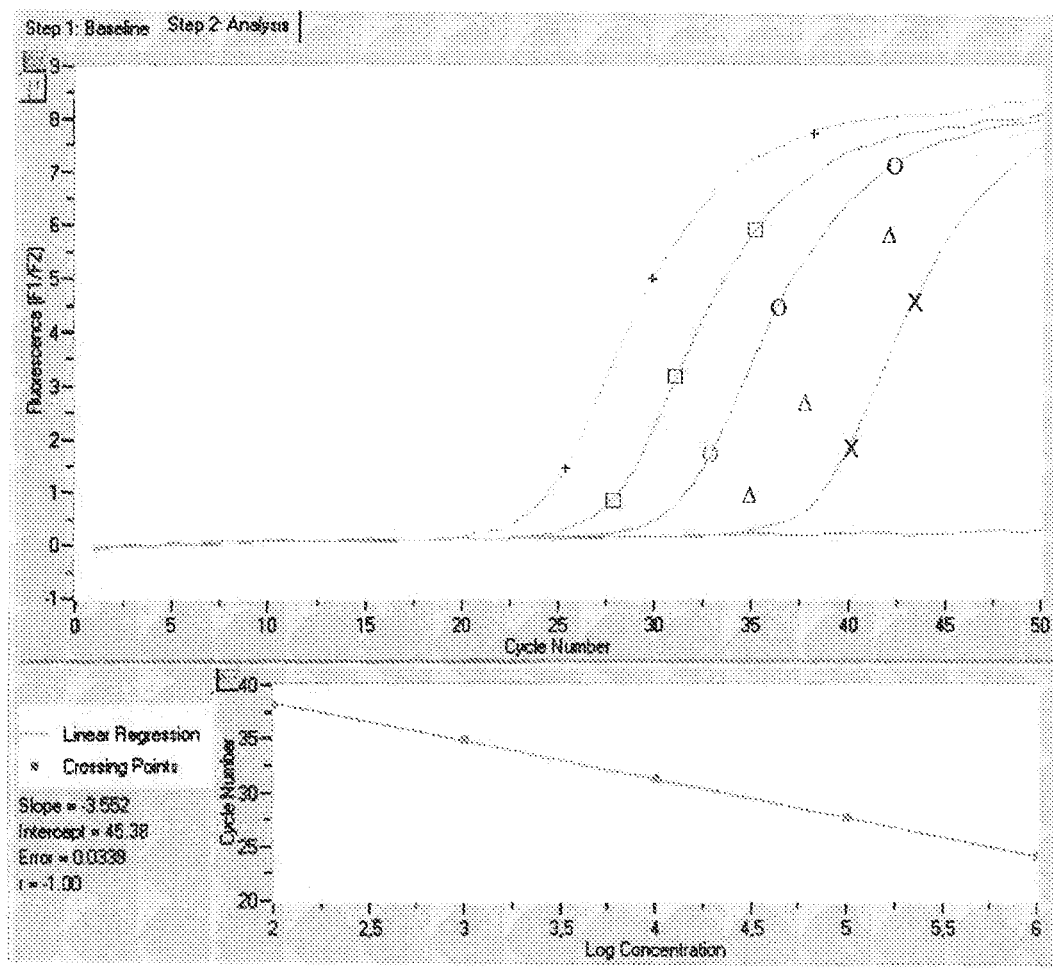

FIG. 6B: The curve is done using optimized experimental conditions disclosed in Example 2. Points of the curve: V6, $10^6$ copies; V5, $10^5$ copies; V4, $10^4$ copies; V3, $10^3$ copies; V2, $10^2$ copies; V1, 10 copies; V1c, one copy.

Figure 6C:
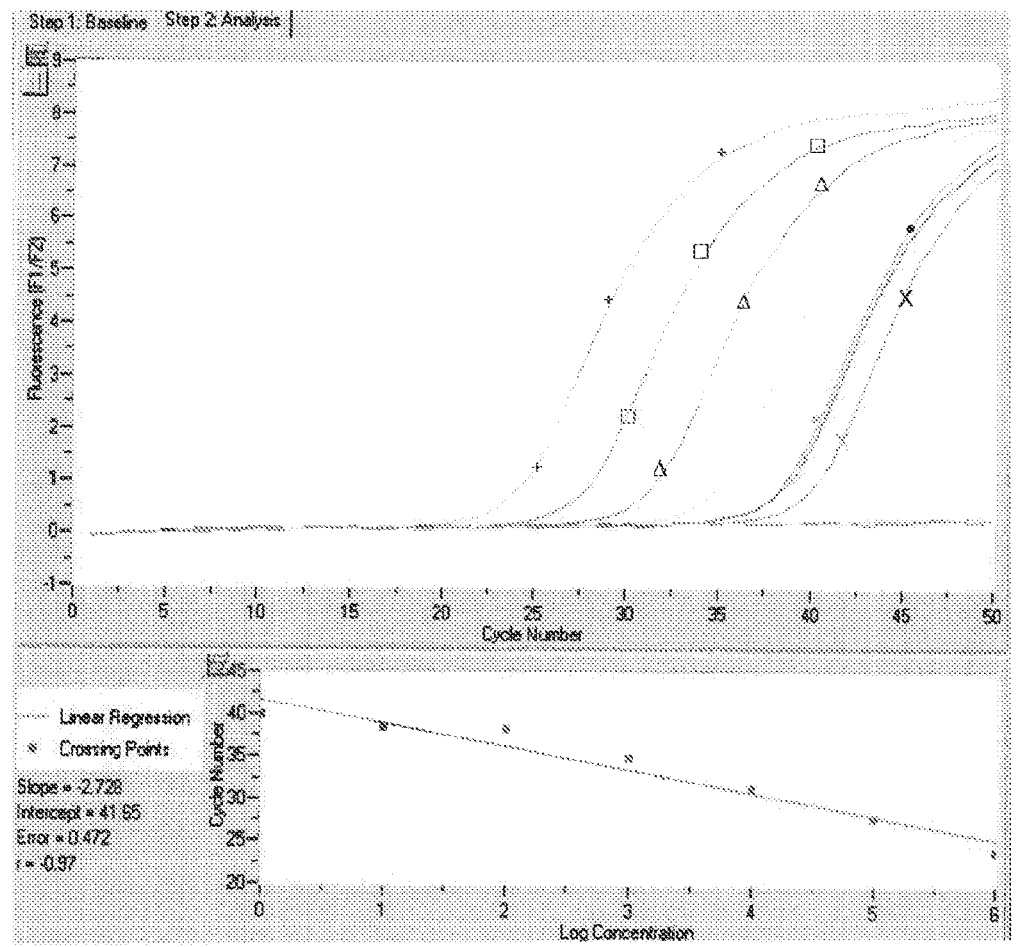
Figure 7A:
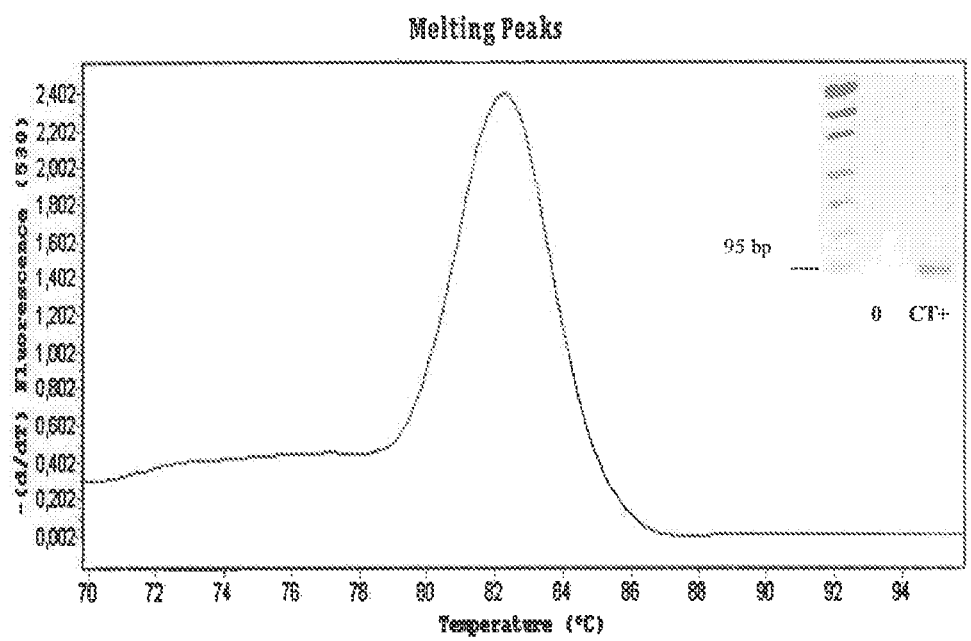
Figure 7B:
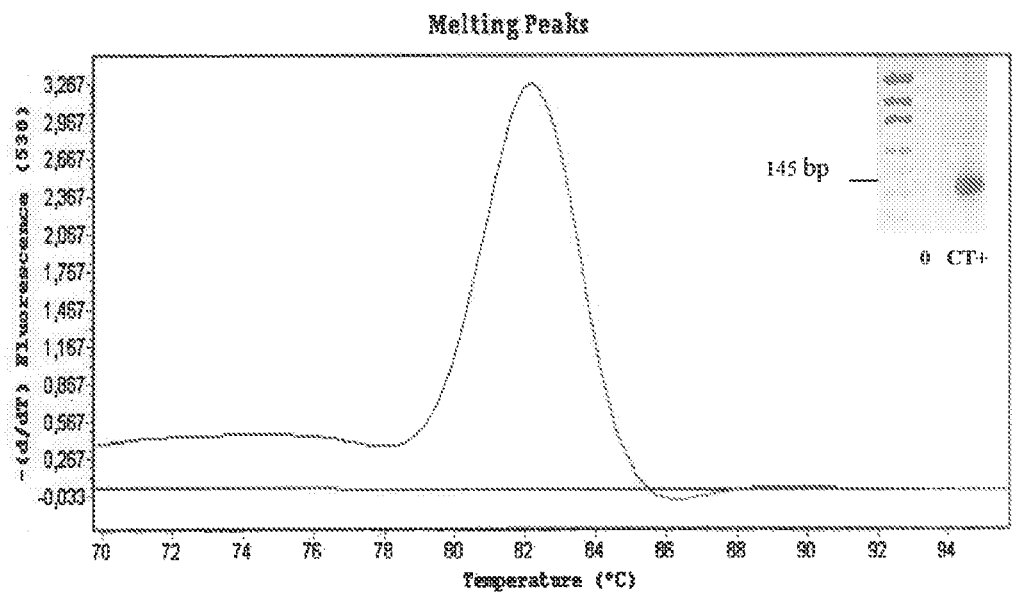
Figure 7C:
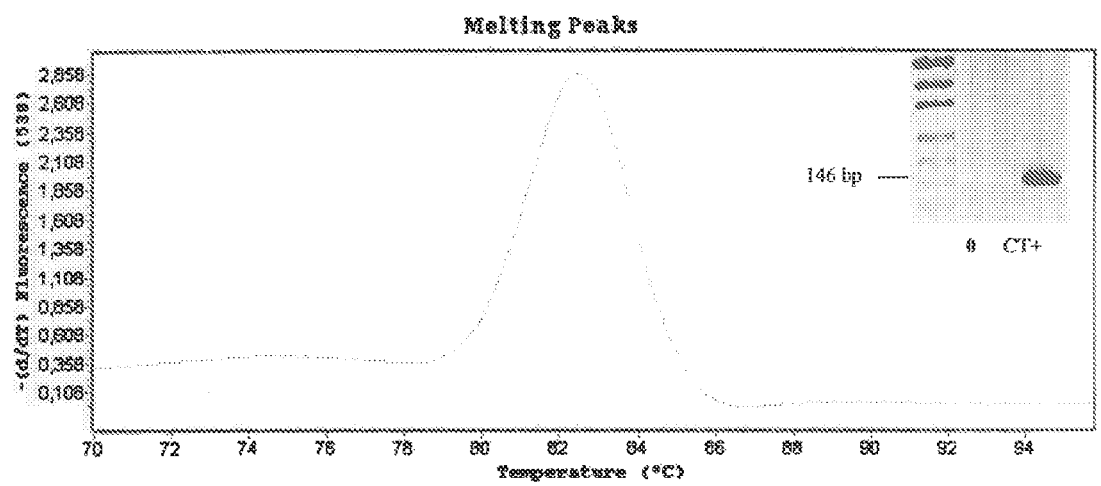
Figure 7D:
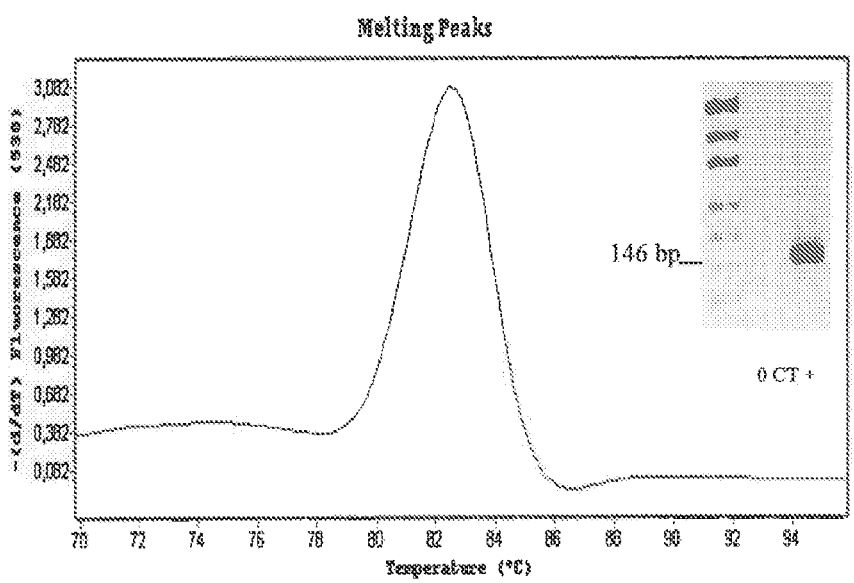

FIG. 6C: Same as FIG. 6B, except that points V1 and V1c are added to calculate the standard curve.

FIG. 7: Tests of primers for VEGF165, 145, 206 and 189 isoforms. For each isoform, tests for setting PCR conditions were performed with SybrGreen technology. FIG. 7A: amplification specific for VEGF165. FIG. 7B: amplification specific for VEGF145. FIG. 7C: amplification specific for VEGF206. FIG. 7D: amplification specific for VEGF189.

SybrGreen PCR conditions for each amplification: Denaturation: 10 min-95° C.; Amplification (45 cycles): 5 s-95° C.; 10 s-60° C.; 12 s-72° C.; Fusion: 0 s-95° C.; 20 s-70° C. at 0,1° C./s; 0 s-96° C.; Cooling: 2 min.-40° C.

FIG. 8: Calibration scales.

Figure 8A:
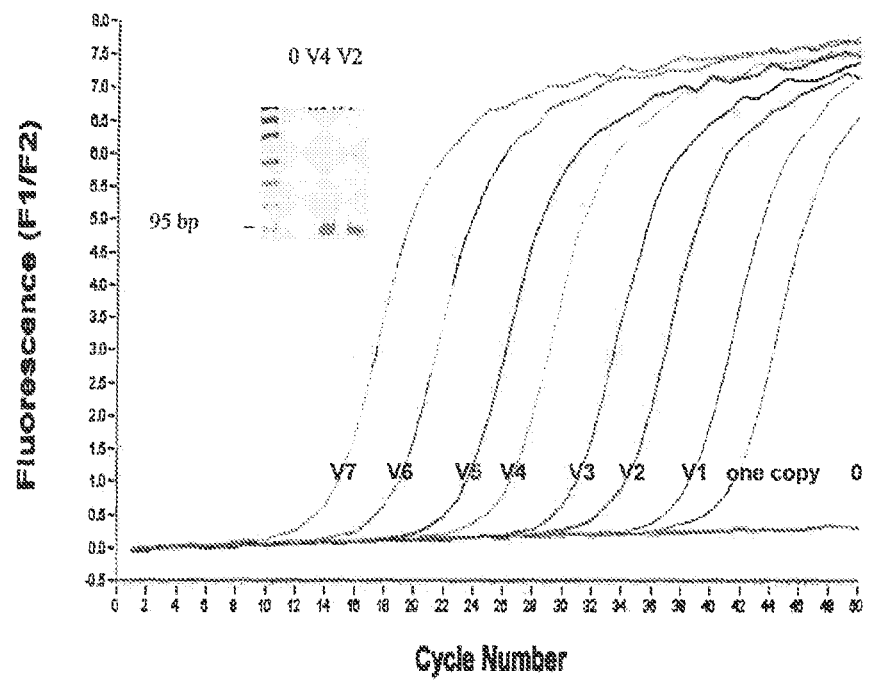

FIG. 8A: Calibration scale for VEGF165. V7: $10^7$ copies; V6: $10^6$ copies; V5: $10^5$ copies; V4: $10^4$ copies; V3: $10^3$ copies; V2: $10^2$ copies; V1: 10 copies; 1: one copy. PCR Conditions: Denaturation: 10 min-95° C.; Amplification (45 cycles): 10 s-95° C.; 15 s-60° C.; Cooling: 30 s-40° C.

Figure 8B:
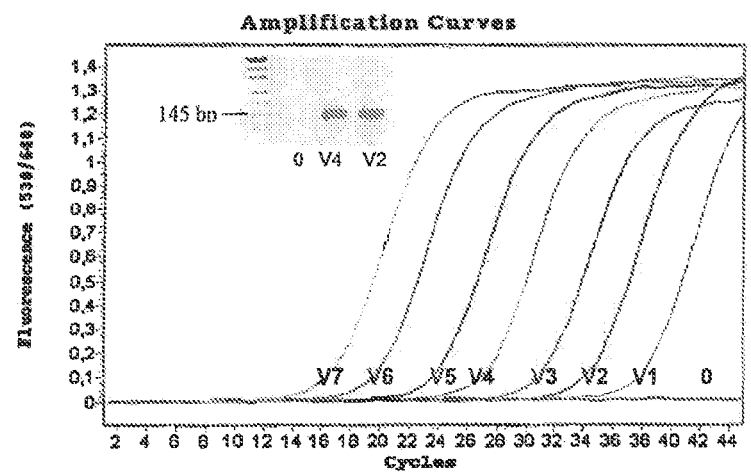

FIG. 8B: Calibration scale for VEGF145. V7: $10^7$ copies; V6: $10^6$ copies; V5: $10^5$ copies; V4: $10^4$ copies; V3: $10^3$ copies; V2: $10^2$ copies; V1: 10 copies. PCR Conditions: Denaturation: 10 min-95° C.; Amplification (45 cycles): 10 s-95° C.; 20 s-60° C.; 10 s-72° C.; Cooling: 30 s-40° C.

Figure 8C:
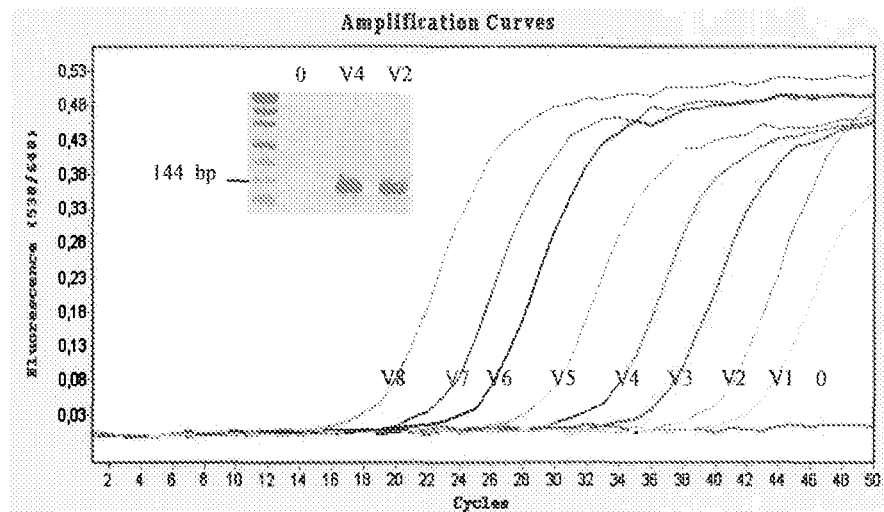

FIG. 8C: Calibration scale for VEGF189. V8: $10^8$ copies; V7: $10^7$ copies; V6: $10^6$ copies; V5: $10^5$ copies; V4: $10^4$ copies; V3: $10^3$ copies; V2: $10^2$ copies; V1: 10 copies. PCR Conditions: Denaturation: 10 min-95° C.; Amplification (45 cycles): 10 s-95° C.; 15 s-60° C.; Cooling: 30 s-40° C.

Figure 8D:
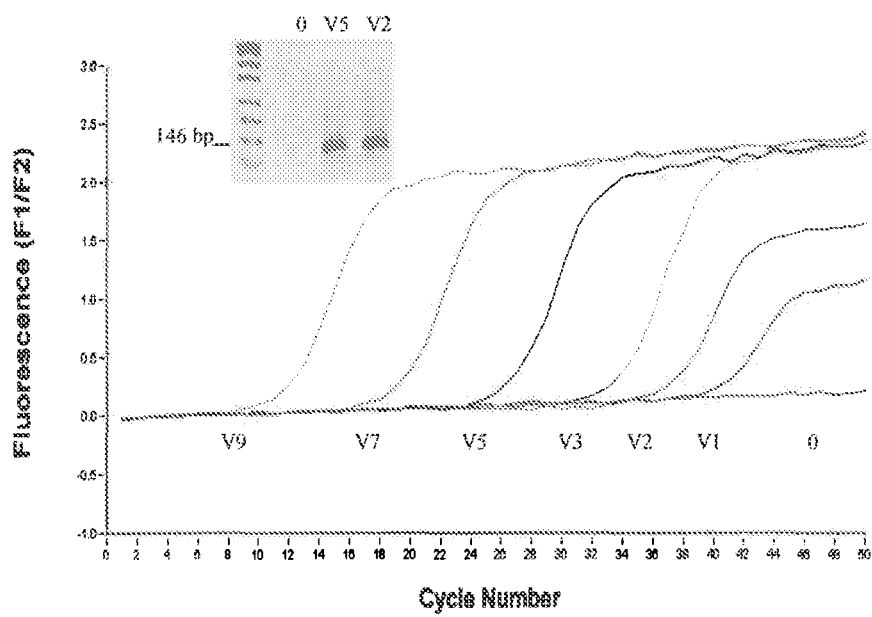

FIG. 8D: Calibration scale for VEGF206

FIG. 9: Mutilplex Q-RT-PCR

Figure 9A:
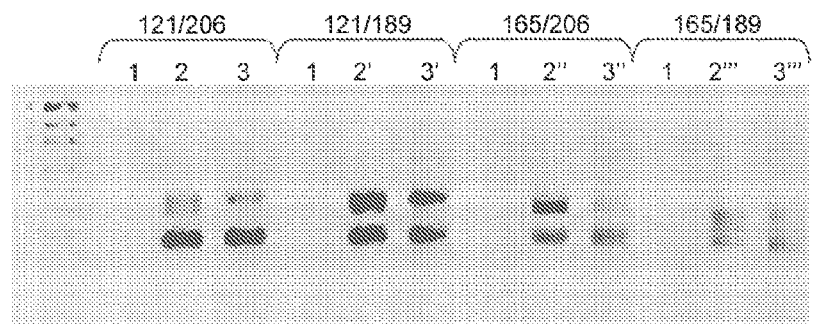

FIG. 9A: Multiplex PCR were performed with primer sets from two transcripts using SybrGreen Technology, and visualized in agarose gel. 121/206: 1-$H_2O$: negative control; 2-$10^6$ copies of VEGF206 isoform and $10^2$ copies of VEGF121 isoform; 3-$10^6$ copies VEGF206 isoform and $10^1$ copies of VEGF121 isoform. 121/189: 2'-$10^6$ copies of each isoform (VEGF121 and VEGF189); 3'-$10^4$ copies of each isoform (VEGF121 and VEGF189). 165/206: 2"-$10^4$ copies of each isoform (VEGF165 and VEGF206); 3"-$10^2$ copies of each isoform (VEGF165 and VEGF206). 165/189: 2'''-$10^4$ copies of each isoform (VEGF165 and VEGF189); 3'''-$10^4$ copies of each isoform (VEGF165 and VEGF189). SybrGreen PCR Conditions: Denaturation: 10 min-95° C.; Amplification 45 cycles: 10 s-95° C.; 20 s-60° C.; 10 s-72° C.; Cooling: 30 s-40° C.

Figure 9B:
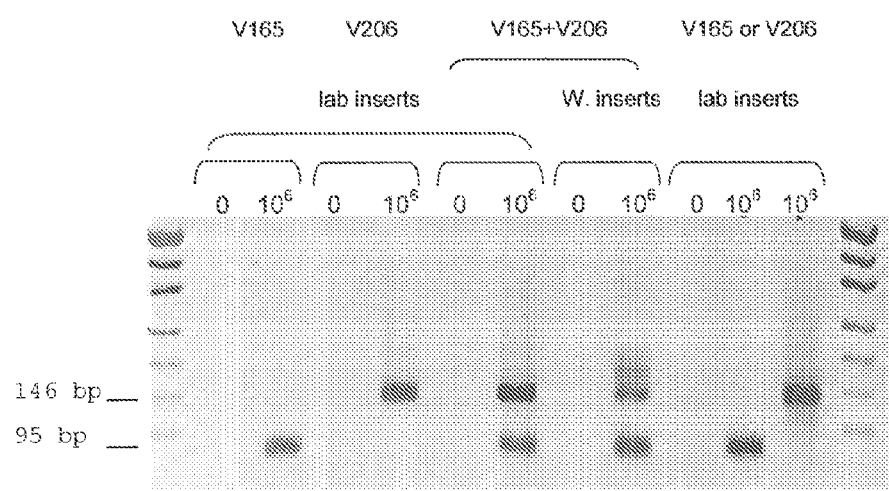

FIG. 9B: VEGF165 & VEGF206 multiplex validation using SybrGreen technology. Different tempates were used: V165 and V206 are the amplification products obtained with the primer pairs specific for VEGF165 and VEGF206 transcripts, respectively, as described in Example 2 ("lab inserts") or by Wellmann et al, supra ("W. inserts").

Figure 9C:
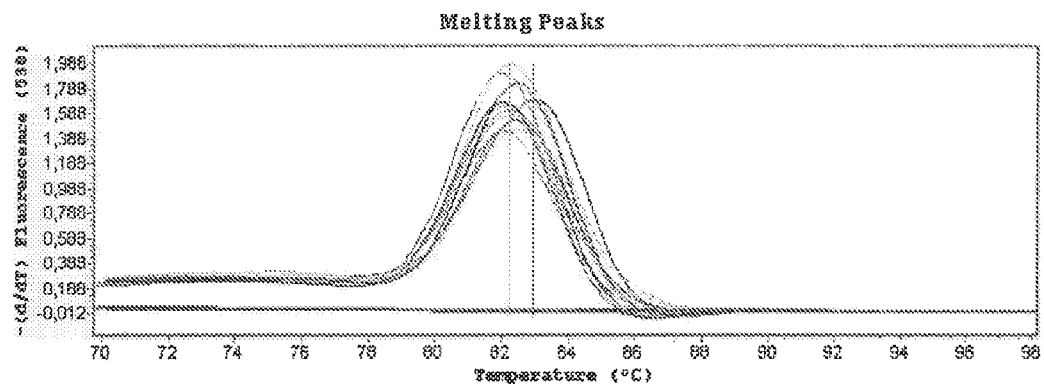

FIG. 9C: Melting Peaks obtained after multiplex Q-RT-PCR using SybrGreen technology.

Figure 9D:
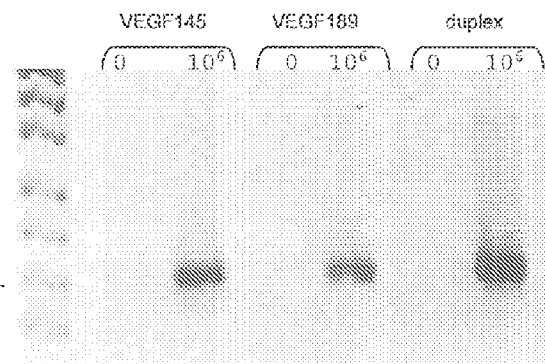

FIG. 9D: VEGF145 & VEGF189 multiplex validation using SybrGreen technology.

Figure 9E:
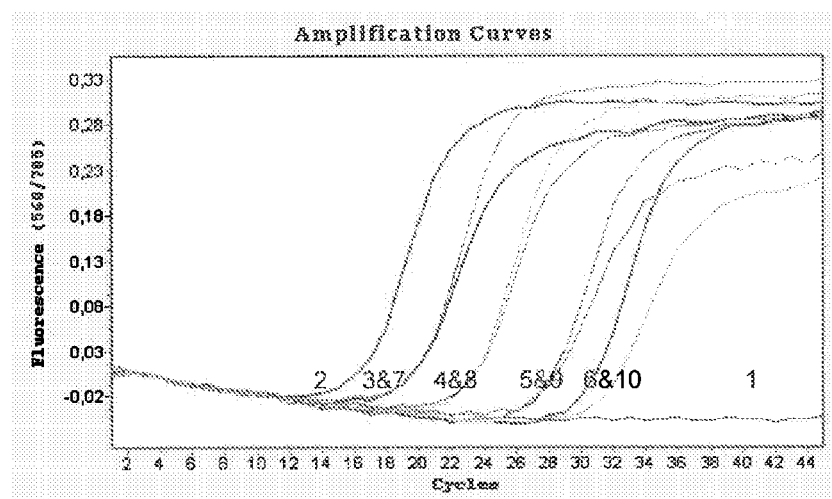

FIG. 9E: VEGF165/VEGF206 multiplex quantification using TaqMAn probe technology. Q-RT-PCR conditions: denaturation step: 10 min-95° C.; amplification (45 cycles): 10 s-95° C.; 20 s-60° C.; 10 s-72° C.; cooling step: 30 s-40° C. Each curve corresponds to one tube; the content of each tube is indicated in Table 1 below (Example 3).

Figure 9F:
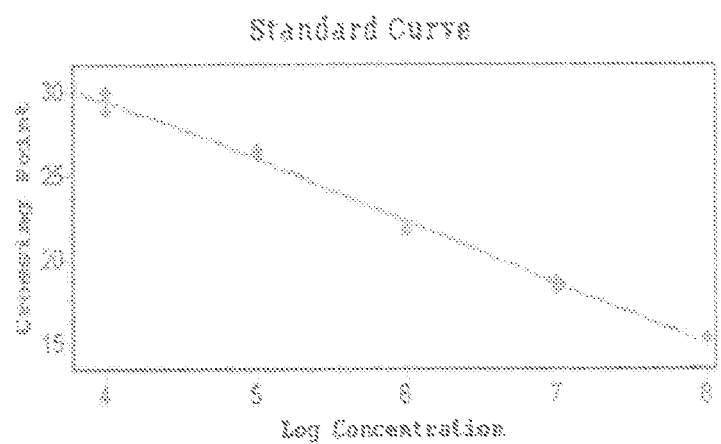

FIG. 9F: VEGF206 Standard curve corresponding to all reactions containing VEGF206 standards: 2-10 (reported in Table 1) (fluorescence reading at 560 nm).

Figure 9G:
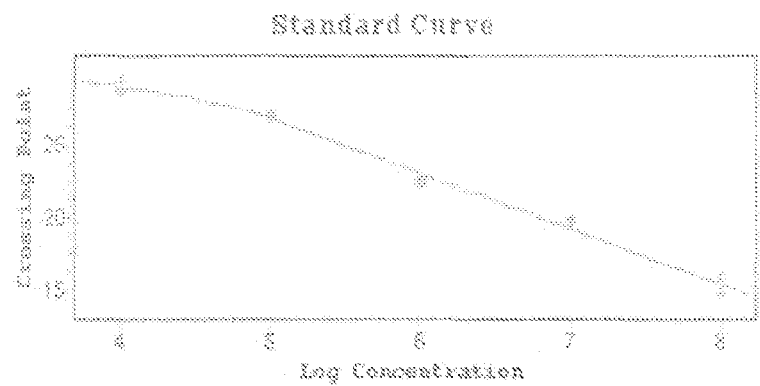

FIG. 9G: VEGF165 Standard curve corresponding to all reactions containing VEGF 165 standards: 2-10 (reported in Table 2).

Figure 9H:
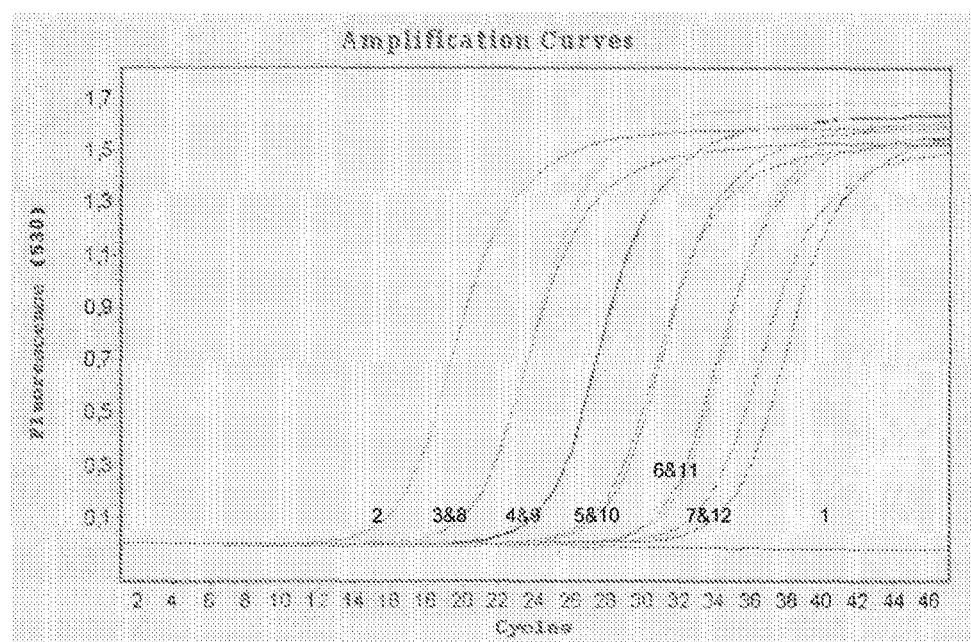

FIG. 9H: VEGF145/VEGF189 multiplex quantification using TaqMAn probe technology. Q-RT-PCR conditions: denaturation step: 10 min-95° C.; Amplification (45 cycles): 10 s-95° C.; 20 s-60° C.; 10 s-72° C.; Cooling: 30 s-40° C. Each curve corresponds to one tube; the content of each tube is indicated in Table 3 below (Example 3).

Figure 9I:
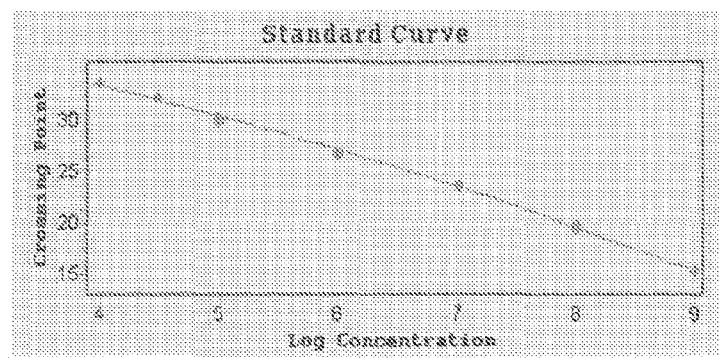

FIG. 9I: VEGF-145 Standard curve corresponding to all reactions containing VEGF-145 standards: 2-11 (reported in Table 3) (fluorescence reading at 530 nm).

Figure 9J:
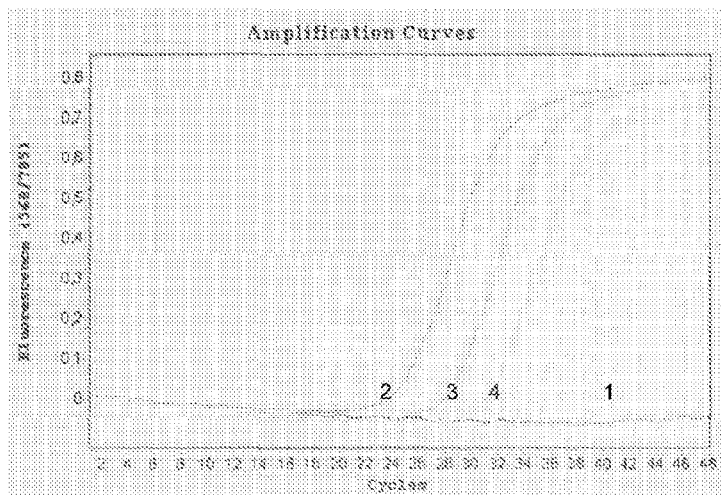

FIG. 9J: VEGF189/VEGF145 multiplex quantification using TaqMAn probe technology. Each curve corresponds to one tube; the content of each tube is indicated in Table 4 below (Example 3).

Figure 9K:
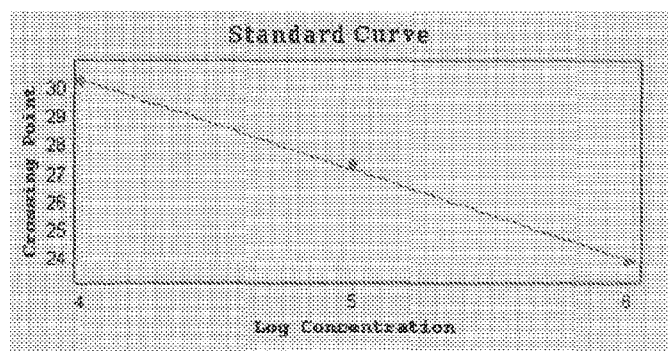

FIG. 9K: VEGF-189 Standard curve corresponding to reactions containing VEGF-189 standards: 2-4 (reported in Table 4) (fluorescence reading at 560 nm).

Figure 10:
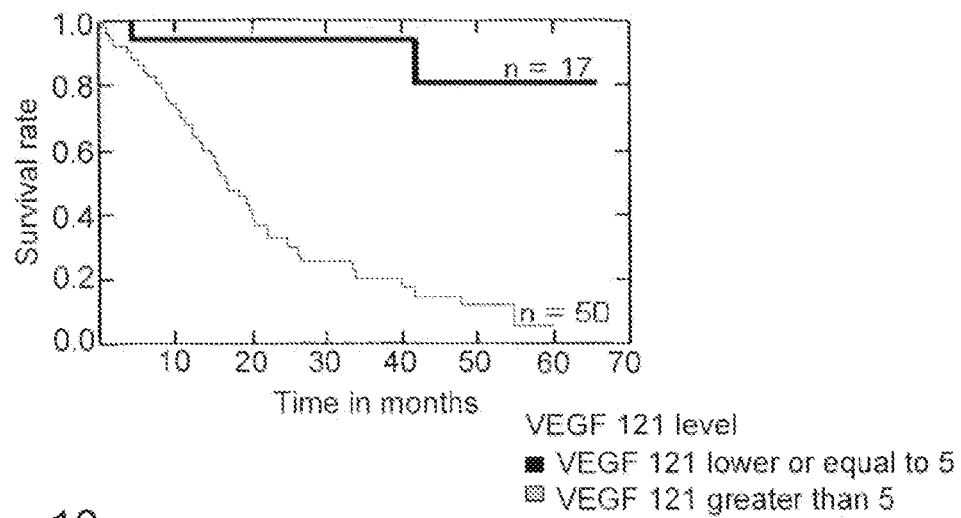

FIG. 10: Kaplan-Meier survival curve. VEGF121=5 means that the ratio of VEGF121 and β2-microglobulin transcripts is =5 copies of VEGF121/$10^4$ copies of β2 m. Similarly, VEGF121>5 means that the ratio of VEGF121 and β2-microglobulin transcripts is >5 copies of VEGF121/$10^4$ copies of β2 m. Overall survival (OS): p<0.0001.

Figure 11:
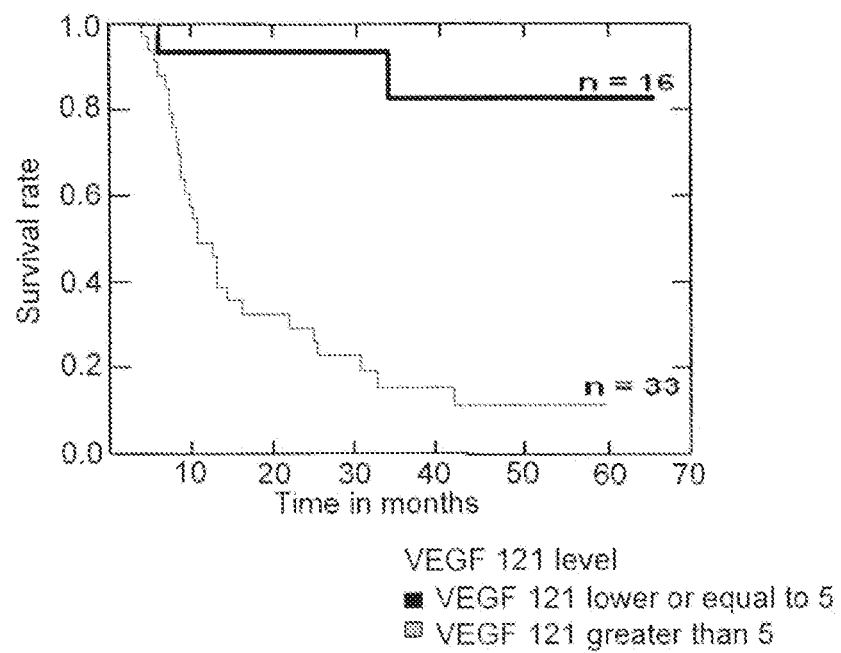

FIG. 11: Kaplan-Meier disease-free survival curve. VEGF121=5 means that the ratio of VEGF121 and β2-microglobulin transcripts is =5 copies of VEGF121/$10^4$ copies of β2 m. Similarly, VEGF121>5 means that the ratio of VEGF121 and β2-microglobulin transcripts is >5 copies of VEGF121/$10^4$ copies of β2 m. Disease free survival (EFS): p<0.0001.

Figure 12:
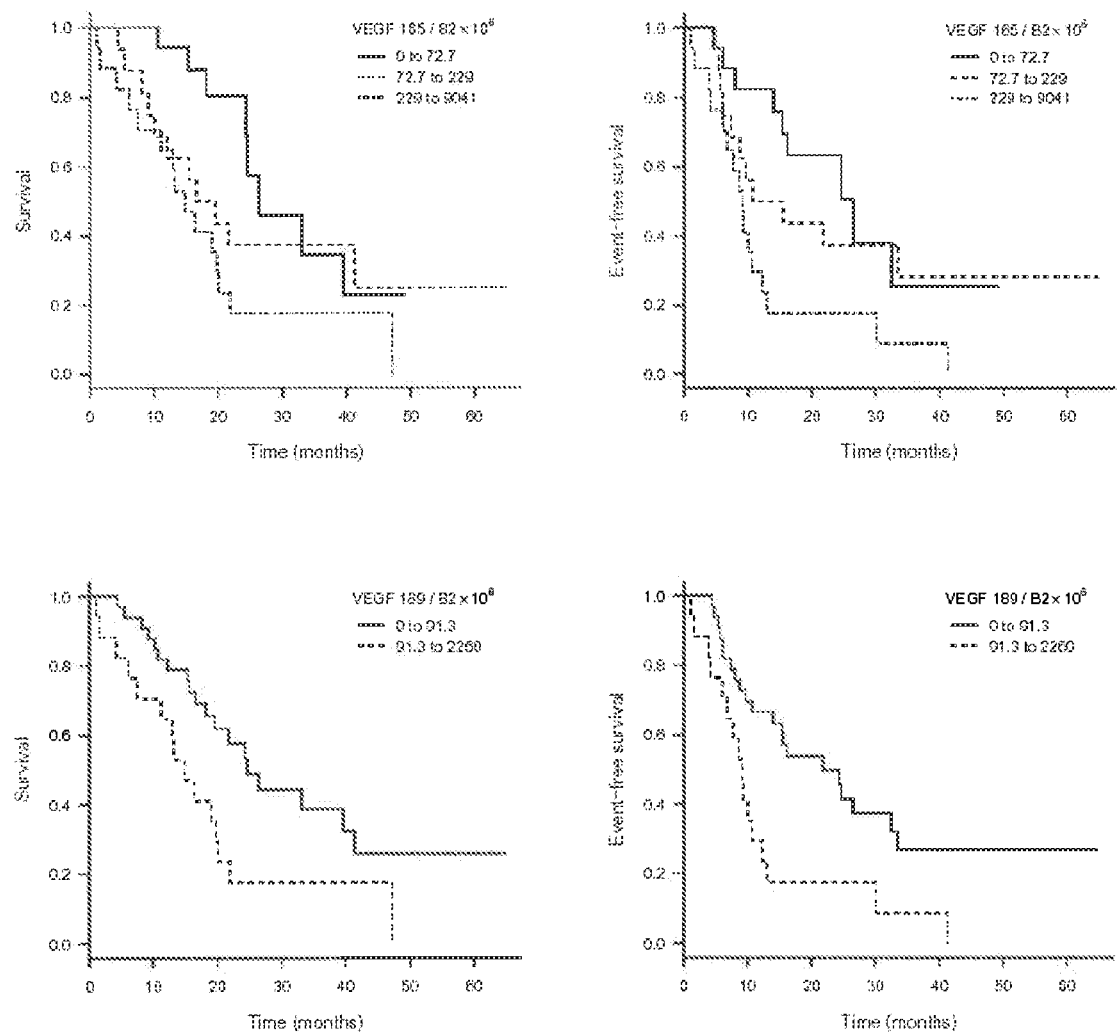

FIG. 12: Survival and event-free survival in AML patients, having regard to VEGF165/B2 and VEGF189/B2. VEGF 165 & AML: EFS: p=0.012 and OS: p=0.017. VEGF189 & AML: EFS: p=0.008 and OS: p=0.12.

FIG. 13: Long-term (15 years) disease free survival analyses in 126 breast cancer patients. Patients were separated in two groups according to the AUC method. FIG. 13A: VEGF121/TBP-group 1: 0 to 5.1, group 2: >5.1; p=0.064. FIG. 13B: VEGF165/b2 m-group 1: 0 to 9060, group 2: > 9060; p=0.059. FIG. 13C: VEGF165/TBP-group 1: 0 to 7.3, group 2: >7.3; p=0.049. FIG. 13D: Ratio VEGF 165/121-group 1: R<3, group 2: R=3; p=0.0028. FIG. 13E: Ratio VEGF 165/121-group 1: <2.03, group 2: 2.03<x<5.3 and group 3: >5.30; p=0.031.

EXAMPLES

Example 1

VEGF121 Quantification Comparative Experiments

Step 1: comparison of selected sets of primers with that of Wellmann et al (Wellmann, Taube et al. 2001), and determination of optimal PCR conditions.

Two sets of primers have been selected for their high sensitivity and selectivity:

```
First set: leads to amplification of a
fragment of 99 bp
forward:
5'-AGGCCAGCACATAGGAGAGAT-3'    (SEQ ID NO: 1)
and reverse:
5'-CTCGGCTTGTCACATTTTTC-3'     (SEQ ID No: 2)

Second set: leads to amplification of a
fragment of 78 bp
forward:
5'-GAGCTTCCTACAGCACAACAAA-3';  (SEQ ID No: 3)
and reverse:
5'-CTCGGCTTGTCACATTTTTC-3'.    (SEQ ID No: 2)
```

The PCR conditions have been determined using the SybrGreen technology (which is very sensitive). As shown in FIG. 2, the above sets of primers amplify only one product (only one peak can be seen with SybrGreen).

These amplification products, when loaded on an agarose gel, show only one band for each of the sets, each one being at the predicted size: 99 bp for the first set and 78 for the second (FIG. 3).

The primers described by Wellmann et al (Wellmann, Taube et al. 2001) have been tested in parallel. The PCR product obtained after amplification has been loaded on the same agarose gel. Contrarily to the sets according to the present invention, this set of primers generated 2 amplification products, as shown in FIG. 3 (lane D12). One of said product is as expected (254 bp), whereas an additional band appears at an apparent size of around 75 bp. Hence, the primer set disclosed by Wellmann et al (Wellmann, Taube et al. 2001) lacks specificity.

Step 2: Calibration curves with the selected sets of primers

The calibration curves show that the detection threshold using the first set of primers (SEQ ID Nos: 1 and 2) is of one copy of VEGF121 transcript (FIG. 4), and of 5 copies of said transcript when using the second set of primers (FIG. 5).

Step 3: Comparison of obtained calibration curves (selected sets of primers vs primer set disclosed by Wellmann et al)

A first standard curve was obtained using the primer set of Wellmann et al in the same conditions as described by the authors (Wellmann, Taube et al. 2001). This led to a detection threshold of 100 copies, as shown in FIG. 3 of the article by Wellmann et al, supra.

The amplification was then optimized, by applying the conditions described in Example 2 for amplification with the primers of Wellmann et al. This led to the same detection level as described in the article by Wellmann et al, i.e., detection of 100 copies (FIG. 6B).

As shown in FIG. 6C, the points corresponding to 10 and 1 copy of VEGF121 transcript are irrelevant.

Example 2

Quantification of VEGF165, VEGF145, VEGF189 and VEGF206 in Tissue Samples

The following primers and probes were designed and selected for quantifying the other VEGF isoforms through highly sensitive and selective Q-RT-PCR

```
                                           (SEQ ID No: 3)
VEGF165 forward:
5'-gAg CTT CCT ACA GCA CAA CAA A-3', (SEQ ID No: 9)
VEGF165 reverse:
5'-gCT TTC TCC gCT CTg AgC A-3', (SEQ ID No: 10)
VEGF165 probe:
5'-AgC AAg ACA AgA AAA TCC CTg Tgg gCC-3';

(SEQ ID No: 3)
VEGF145 forward:
5'-gAg CTT CCT ACA gCA CAA CAA A-3', (SEQ ID No: 11)
VEGF145 reverse:
5'-CTT gTC ACA TAC gCT CCA ggA C-3', (SEQ ID No: 12)
VEGF145 probe:
5'-AAA CgA AAg CgC AAg AAA TCC Cgg TA-3';

(SEQ ID No: 3)
VEGF189 forward:
5'-gAg CTT CCT ACA gCA CAA CAA A-3', (SEQ ID No: 13)
VEGF189 reverse:
5'-CCA CAg ggA ACg CTC CAg gAC-3', (SEQ ID No: 14)
VEGF189 probe:
5'-AgC AAg ACA AgA AAA AAA ATC AgT TCg Agg AAA-3';

(SEQ ID No: 3)
VEGF206 forward:
5'-gAg CTT CCT ACA gCA CAA CAA A-3', (SEQ ID No: 15)
VEGF206 reverse:
5'-CAC CAA CgT ACA CgC TCC Agg-3', (SEQ ID No: 14)
VEGF206 probe:
5'AgC AAg ACA AgA AAA AAA ATC AgT TCg Agg AAA3'
```

As shown in FIG. 7, only one amplification product was obtained with each set of primers (one peak in SybrGreen). Analysis on agarose gel revealed only one band at expected size (for each isoform): VEGF165: 95 pb, VEGF145: 145 pb, VEGF206: 146 pb, VEGF189: 144 pb.

Standards were used for calibration curves for each transcript (VEGF isoforms and housekeeping genes). Standards were prepared as follows: RNA from normal tissues was amplified by RT-PCR using specific primers for each VEGF isoform (VEGF121, VEGF165, VEGF145, VEGF189, and VEGF206) and for housekeeping genes (TBP and β2 microglobin). PCR products were cloned in TOPO II TA cloning Kit (Invitrogen) following the manufacturer's recommendations. Cloned products were digested with EcoRI (Invitrogen), extracted from 2% agarose gel, purified with the PCR purification Kit (Qiagen). Finally the products were measured in a spectrophotometer, and molecule concentrations were calculated.

Calibration scales (FIG. 8) show that these sets of primers and probes enable the detection of 10 (VEGF189, VEGF145, VEGF206) or even one single (VEGF121 and VEGF165) transcript(s) in a biological sample, whereas no amplification occurs in the absence of VEGF isoform transcripts (VEGF189, VEGF145, VEGF206, VEGF121 and VEGF165).

These setting tests hence validate, for each isoform, a quantification methodology at transcript level, which is highly specific (100% specificity) and sensitive (between 98 and 100%).

Example 3

Multiplex Q-RT-PCR

Highly sensitive and selective multiplex tests based on the Q-RT-PCR technology were then developed. This novel method enables accurate quantification of 2 different isoforms in the same PCR reaction (same PCR mix).

The inventors first tested the efficacy and sensitivity of different combinations of primer sets from four different isoforms, using SybrGreen Technology in presence of home made standards at variable concentrations (see example 2 for standard preparation). After multiplex amplification, the PCR products were loaded on agarose gel to check the specificity of the amplification systems (FIG. 9A).

From this experiment, the following combinations were retained: VEGF165 isoform transcripts are quantified simultaneously with VEGF206 isoform transcripts and VEGF145 isoform transcripts are quantified simultaneously with VEGF189 isoform transcripts.

FIG. 9B shows the VEGF165 and VEGF206 multiplex validation, using SybrGreen technology. The multiplex V165/V206 system according to the invention (Primer sets and standard construction) provided highly specific results compared to those obtained by Wellmann et al, supra.

As shown in FIG. 9C, 2 distinct products with 2 Tm have been amplified in this V165/V206 system: 82.10 and 82.95. The specificity of these amplifications has been validated (see FIGS. 9A & 9B).

The same methodology has been used to validate V145/V189 multiplex Q-RT-PCR.

The combination efficacy and sensitivity of primer sets from VEGF145 and VEGF189 isoforms was first tested using SybrGreen Technology. The PCR products were loaded on agarose gel to check the specificity of the amplification systems. The system did not reveal non-specific amplification products (FIG. 9D). As expected, one band was obtained at 145 and 144 pb, corresponding to VEGF145 and VEGF189 size products, respectively.

After SybrGreen validation steps, the inventors quantified 2 different isoforms VEGF165 and VEGF206 in the same Q-RT-PCR reaction, using 2 different quantification systems simultaneously. Each system is specific of one transcript (see below)

VEGF165 system contains:
VEGF165 forward primer
VEGF165 reverse primer
VEGF165 TaqMan probe labeled with FAM/TAMRA, which has a fluorescence emission read at 530 nm.
VEGF206 system contains:
VEGF206 forward primer
VEGF206 reverse primer
VEGF206 TaqMan probe labeled with VIC/TAMRA, which has a fluorescence emission read at 560 nm.

Transcript quantification depends on the channel chosen for fluorescence reading:
by reading at 530 nm fluorescence, only VEGF165 transcripts are detected despite the presence of VEGF206 system and its transcripts; and
by reading at 560 nm fluorescence, only VEGF206 transcripts are detected despite the presence of VEGF165 system and its transcripts (see FIG. 9E)

The inventors performed the quantification of both VEGF isoforms transcripts (VEGF165 and VEGF206) in a multiplex fashion, by adding in the same reaction the 2 specific systems (VEGF165 and VEGF206 systems) in presence of both standards of each isoform at different concentrations. These experiments have been conducted in duplicate. An example of VEGF206 quantification experiment is depicted in Table 1.

Q-RT-PCR conditions used are as follows:
Denaturation step: 10 min-95° C.; Amplification step: 10 s-95° C.; 20 s-60° C.; 10 s-72° C.; Cooling step: 30 s-40° C.

TABLE 1

| Tube | Q-RT-PCR reactions | PCR Crossing points (CP) obtained at 560 nm |
|---|---|---|
| 1 | VEGF206 and VEGF165 systems + H2O | |
| 2 | VEGF206 and VEGF165 systems + $10^8$ copies V206 standard + $10^8$ copies V165 standard | 15.09 |
| 3 | VEGF206 and VEGF165 systems + $10^7$ copies V206 standard | 18.53 |
| 4 | VEGF206 and VEGF165 systems + $10^6$ copies V206 standard + $10^6$ copies V165 standard | 21.62 |
| 5 | VEGF206 and VEGF165 systems + $10^5$ copies V206 standard + $10^5$ copies V165 standard | 26.17 |
| 6 | VEGF206 and VEGF165 systems + $10^4$ copies V206 standard + $10^4$ copies V165 standard | 28.79 |
| 7 | VEGF206 and VEGF165 systems + $10^7$ copies V206 standard + $10^8$ copies V165 standard | 18.16 |
| 8 | VEGF206 and VEGF165 systems + $10^6$ copies V206 standard + $10^7$ copies V165 standard | 21.70 |
| 9 | VEGF206 and VEGF165 systems + $10^5$ copies V206 standard + $10^6$ copies V165 standard | 26.40 |
| 10 | VEGF206 and VEGF165 systems + $10^4$ copies V206 standard + $10^5$ copies V165 standard | 29.89 |
| 11 | VEGF165 and VEGF206 systems + $10^4$ copies V165 standard | |

VEGF206 calibration scale in multiplex assay (fluorescence reading at 560 nm channel) is shown in FIG. 9E, and the corresponding standard curve in FIG. 9F.

As shown in Table 1, the presence of VEGF165 systems and its transcript do not interfere with the accurate quantification of VEGF206 (crossing points are very close). For example, the results corresponding to tubes 4 and 8, and those of tubes 5 and 9 can be compared. In addition, the tube number 11 (see Table 1) containing both systems and only the VEGF165 standard ($10^4$ copies) shows no detection (no CP observed) of VEGF165.

An example of VEGF165 quantification experiment is depicted in Table 2.

TABLE 2

| | Q-RT-PCR reactions | PCR Crossing points (CP) obtained at 530 nm |
|---|---|---|
| 1 | VEGF165 and VEGF206 systems + H2O | |
| 2 | VEGF165 and VEGF206 systems + $10^8$ copies V165 standard + $10^8$ copies V206 standard | 14.79 |
| 3 | VEGF165 and VEGF206 systems + $10^6$ copies V165 standard + $10^6$ copies V206 standard | 22.58 |

TABLE 2-continued

| | Q-RT-PCR reactions | PCR Crossing points (CP) obtained at 530 nm |
|---|---|---|
| 4 | VEGF165 and VEGF206 systems + $10^5$ copies V165 standard + $10^5$ copies V206 standard | 26.78 |
| 5 | VEGF165 and VEGF206 systems + $10^4$ copies V165 standard + $10^4$ copies V206 standard | 29.41 |
| 6 | VEGF165 and VEGF206 systems + $10^8$ copies V165 standard + $10^7$ copies V206 standard | 15.88 |
| 7 | VEGF165 and VEGF206 systems + $10^7$ copies V165 standard + $10^6$ copies V206 standard | 19.76 |
| 8 | VEGF165 and VEGF206 systems + $10^6$ copies V165 standard + $10^5$ copies V206 standard | 22.35 |
| 9 | VEGF165 and VEGF206 systems + $10^5$ copies V165 standard + $10^4$ copies V206 standard | 27.05 |
| 10 | VEGF165 and VEGF206 systems + $10^4$ copies V165 standard + $10^3$ copies V206 standard | 29.63 |
| 11 | VEGF165 and VEGF206 systems + $10^7$ copies V206 standard | |

The standard curve shown in FIG. 9G corresponds to all reactions containing VEGF165 standards: 2-10 (reported in table 2).

As shown in Table 2 (when comparing, for example, lines 3 and 8 or lines 4 and 9), the presence of VEGF206 systems and its transcript do not interfere with the accurate quantification of VEGF165 (crossing points are very close). In addition, the tube number 11 containing both systems and only the VEGF206 standard ($10^7$ copies) shows no detection (no CP observed) of VEGF 206.

In conclusion, the assay herein described enables the quantification of at least 2 isoforms in the same reaction, based on multiplex Q-RT-PCR. As shown in these results, the detection using this assay is specific accurate and sensitive.

Similar results were obtained with the same efficacy by using this assay to quantify in multiplex fashion the isoforms VEGF145 and VEGF189.

After SybrGreen validation steps, the inventors quantified the 2 different isoforms VEGF145 and VEGF189 in the same Q-RT-PCR reaction, using 2 different quantification systems simultaneously. Each system is specific of one transcript (see below).

VEGF145 system contains:
VEGF145 forward primer
VEGF145 reverse primer
VEGF145 TaqMan probe FAM/TAMRA labelled, which has a fluorescence emission read at 530 nm.

VEGF189 system contains:
VEGF189 forward primer
VEGF189 reverse primer
VEGF189 TaqMan probe labelled with VIC/TAMRA, which has a fluorescence emission read at 560 nm.

Transcript quantification depends on the channel chosen for fluorescence reading:
by reading at 530 nm, only VEGF145 transcripts are detected despite the presence of VEGF 189 system and its transcripts; and
by reading at 560 nm, only VEGF189 transcripts are detected despite the presence of VEGF145 system and its transcripts (see FIG. 9H).

The quantification of both VEGF isoforms transcripts (VEGF145 and VEGF189) was performed in a multiplex fashion by adding in the same reaction the 2 specific systems (VEGF145 and VEGF189 systems) in presence of both standards of each isoform at different concentrations. These experiments have been conducted in duplicate. An example of VEGF145 quantification experiment is depicted in Table 3.

Q-RT-PCR conditions used are as follows:
Denaturation step: 10 min-95° C.; Amplification step: 10 s-95° C.; 20 s-60° C.; 10 s-72° C.; Cooling step: 30 s-40° C.

TABLE 3

| tube | Q-RT-PCR reactions | PCR Crossing points (CP) obtained at 530 nm |
|---|---|---|
| 1 | VEGF145 and VEGF189 systems + H2O | |
| 2 | VEGF145 and VEGF189 systems + $10^9$ copies V145 standard + $10^9$ copies V189 standard | 15.10 |
| 3 | VEGF145 and VEGF189 systems + $10^8$ copies V145 standard + $10^8$ copies V189 standard | 19.30 |
| 4 | VEGF145 and VEGF189 systems + $10^7$ copies V145 standard + $10^7$ copies V189 standard | 23.31 |
| 5 | VEGF145 and VEGF189 systems + $10^6$ copies V145 standard + $10^6$ copies V189 standard | 26.54 |
| 6 | VEGF145 and VEGF189 systems + $10^5$ copies V145 standard + $10^5$ copies V189 standard | 29.92 |
| 7 | VEGF145 and VEGF189 systems + $10^4$ copies V145 standard + $10^4$ copies V189 standard | 33.63 |
| 8 | VEGF145 and VEGF189 systems + $10^8$ copies V145 standard + $10^3$ copies V189 standard | 19.58 |
| 9 | VEGF145 and VEGF189 systems + $10^7$ copies V145 standard + $10^3$ copies V189 standard | 23.54 |
| 10 | VEGF145 and VEGF189 systems + $10^6$ copies V145 standard + $10^3$ copies V189 standard | 26.83 |
| 11 | VEGF145 and VEGF189 systems + $10^5$ copies V145 standard + $10^3$ copies V189 standard | 30.23 |
| 12 | VEGF145 and VEGF189 systems + $3 \times 10^4$ copies V145 standard + $10^3$ copies V189 standard | 32.16 |

Calibration scale for VEGF145 in multiplex assay is shown in FIG. 9H (fluorescence reading at 530 nm channel), and the corresponding standard curve in FIG. 9I.

As shown in Table 3 (compare for example tubes 3 & 8 or tubes 3 & 5), the presence of VEGF189 systems and its transcript do not interfere with the accurate quantification of VEGF145 (crossing points are very close).

An example of VEGF189 quantification experiment is depicted in Table 4.

TABLE 4

| tube | Q-RT-PCR reactions | PCR Crossing points (CP) obtained at 530 nm |
|---|---|---|
| 1 | VEGF189 and VEGF145 systems + H2O | |
| 2 | VEGF189 and VEGF145 systems + $10^6$ copies V189 standard + $10^6$ copies V145 standard | 23.85 |
| 3 | VEGF189 and VEGF145 systems + $10^5$ copies V189 standard + $10^5$ copies V145 standard | 27.32 |
| 4 | VEGF189 and VEGF145 systems + $10^4$ copies V189 standard + $10^4$ copies V145 standard | 30.27 |

TABLE 4-continued

| tube | Q-RT-PCR reactions | PCR Crossing points (CP) obtained at 530 nm |
|---|---|---|
| 5 | VEGF189 and VEGF145 systems + $10^5$ copies V189 standard + $10^6$ copies V145 standard | 26.60 |
| 6 | VEGF189 and VEGF145 systems + $10^4$ copies V189 standard + $10^5$ copies V145 standard | 29.75 |
| 7 | VEGF189 and VEGF145 systems + $10^6$ copies V189 standard + $10^4$ copies V145 standard | 24.05 |

VEGF189 calibration scale in multiplex assay (fluorescence reading at 560 nm channel) is shown in FIG. 9J.

The standard curve shown in FIG. 9K corresponds to all reactions containing VEGF189 standards: 2-4 (reported in Table 4).

As shown in Table 4 (compare for example tubes 2&7 and 4&6), the presence of VEGF145 systems and its transcript do not interfere with the accurate quantification of VEGF189 (crossing points are very close).

In conclusion, the assay described herein allows to quantify at least 2 isoforms in the same reaction, based on multiplex Q-RT-PCR. As shown in these results, the detection using this assay is specific, accurate and sensitive.

Example 4

Vascular Endothelial Growth Factor 121 mRNA Level is Predictive of Poor Prognosis in Acute Myeloid Leukaemia Patients and Methods Patients 67 AML patients referred at diagnosis (AML 0 to 7 excluding AML3 and secondary AML) to Saint Louis Hospital (Paris, France) between 1997 and 2001, and 20 healthy volunteers were included in this study. Eleven patients received high-dose aracytine based induction treatment and 45 patients received standard or intermediate-dose aracytine based induction treatment. Only two patients received bone marrow allograft. The patients' characteristics are shown in table 5. VEGF121 mRNA expression was quantified in PBMC previously to any chemotherapy Cell Preparation, RNA Extraction and Reverse Transcription Peripheral blood mononucleated cells were isolated by Ficoll/Hyplaque density gradient centrifugation, and stored at −80° C. RNAs were extracted using Trizol reagent (Life Technologies, Inc.) as specified by the manufacturer. RNA (1 µg) was processed for cDNA synthesis using superscript II reverse transcriptase (Life technologies, Inc) with random hexamers.

Standard Preparation

VEGF121 and µ2 microglobulin (µ2 m) RNA from normal lymphocytes were amplified by RT-PCR and cloned in TOPO II TA cloning Kit (Invitrogen) following the manufacturer's recommendations. Cloned products were digested with EcoR I (Invitrogen), extracted from 2% agarose gel, purified with the PCR purification Kit (Qiagen). Finally the products were measured in a spectrophotometer, and molecule concentrations were calculated. Standard curves for VEGF121 and β2 microglobulin were generated using serial dilutions of cloned products ranging from one to $10^9$ molecules/µl.

Real-Time Quantitative RT-PCR

To evaluate the relative expression of VEGF121, real time quantitative RT-PCR was performed using LightCycler (Roche). β2 microglobulin transcripts were quantified to relatively express our results. β2 microglobulin primers and fluorescent probe are described bellow: β2 m forward: 5'CGC TCC GTG GCC TTA GC 3' (SEQ ID No: 5), β2 m reverse: 5' GAG TAC GCT GGA TAG CCT CCA 3' (SEQ ID No:6), β2 m probe: 5' FAM TGC TCG CGC TAC TCT CTC TTT CTG GC 3' TAMRA (SEQ ID No:7). VEGF121 primers and probe are as follows: VEGF121 forward: 5'-AGGCCAGCACAT-AGGAGAGAT-3' (SEQ ID No: 1), VEGF121 reverse: 5'-CTCGGCTTGTCACATTTTTC-3' (SEQ ID No: 2), VEGF121 probe: 5' FAM TGCAGACCAAAGAAAGATA-GAGCAAGACA 3' TAMRA (SEQ ID No: 4), Quantitative PCR reaction was carried out with an aliquot of $1/20^{th}$ of the resulting cDNA in a 20 µl volume using 100 nM of the specific hydrolyze probe, 200 nM of the probe flanking appropriate primer pairs, and 18 µl of LC fast start DNA master mix (Roche®).

PCR amplification began with a 8 min denaturation step (Taq DNA polymerase activation) at 94° C., followed by 45 cycles of denaturation at 94° C. for 15 s and annealing/extension at 60° C. for 20 s. All experiments were performed in duplicate. All coefficients of variation of Cp values were <1%. The concentrations of unknown samples were then calculated by setting their crossing points to the standard curve. The expression levels of VEGF121 were normalized to the housekeeping β2 microglobulin gene transcripts.

Statistical Analysis

Descriptive statistics for continuous variates are provided as median, with range. For categorical variates, frequency distribution is provided. Comparisons of means were performed using the Student's t test. Relations between quantitative variates were tested with a Pearson's correlation coefficient test. Prognosis factors for overall survival and disease free survival were determined using univariate analysis (log rank test) and multivariate analysis fitting Cox's proportional hazard regression models. For multivariate survival analysis, odds ratio are presented with their 95% confidence interval.

Results & Discussion

Expression of VEGF121 transcripts was evaluated by QRT-PCR in PBMC of 67 AML patients before any treatment (day 0) and in 20 healthy participants. VEGF121 mRNA was detected in all groups.

Mean VEGF121 mRNA transcripts in AML samples (25.9 copies of VEGF121/$10^4$ copies of β2 m) was significantly higher than in normal control samples (1.9 copies of VEGF121/$10^4$ copies of β2 m) (p<0.001).

Characteristics of the patients and evaluation of VEGF121 are shown in table 5. No relation was found between VEGF121 levels and sex, age, WBC counts.

The median follow up was 49.5 months [32.7-51.9]. Of the 67 AML patients, 52 (78%) achieved complete remission, but 32 (48%) have relapsed and 44 (66%) subsequently deceased. Median survival time was 21.9 months [16.5-33.6] and median disease free survival was 30.4 months [12.4-not estimated].

Following parameters were tested in the univariate analysis: sex, age, WBC, caryotype, and VEGF 121 level. For overall survival, both univariate and multivariate analysis showed that high levels of VEGF121 transcripts (VEGF121 in AML patients >5 copies of VEGF121/$10^4$ copies of β2 m; 25th centile, this cut-point was designed after systematic searches) were significantly related with a worse prognosis (OR=11.6 [2.76-48.6, p=0.008) (FIG. 10). Neither sex nor age nor WBC were related with a bad prognosis in this group of patients. Analysing disease free survival, only high levels of VEGF121 transcripts were significantly related to a worse prognosis (p<0.0001, using univariate analysis) (FIG. 11). Results of univariate analysis for other factors were: sex: p=0.11, age: p=0.98, WBC: p=0.65 and caryotype: p=0.37. Of note, 94% of the patients who relapsed had an initial high level of VEGF121 transcripts.

The data presented herein with 67 unselected patients, show the important part that VEGF plays in AML and bring new insights for a specific role of the more soluble VEGF121 isoform. This transcript quantification is a sensitive, tumor specific (independent from platelets or other circulating blood cells), rapid and simple method. The present findings support the use of this test as a predictive and prognostic tool helping the physician to identify patients who should benefit from alternative therapeutic strategies.

Interestingly, clinical studies with VEGF inhibitors or agents blocking its transduction appear to be promising in leukemias. In a phase II study of SU5416 (VEGF tyrosine kinase inhibitor) conducted on AML patients resistant to standard chemotherapy, Fiedler et al. observed clinical response in 19% (8/43) of cases (Fiedler, Mesters et al. 2003). Monitoring of antiangiogenic treatment through QRT-PCR of VEGF121 could therefore help treating these patients.

TABLE 5

Relations between AML patients characteristics and VEGF level.

|  | Number of Median patients | Range (minimum-maximum) | VEGF ≤5 copies of VEGF121/$10^4$ copies of β2m (n = 17) | VEGF >5 copies of VEGF121/$10^4$ copies of β2m (n = 50) | p |
|---|---|---|---|---|---|
| Gender (males/females) | 34 (51%)/33 (49%) |  | 6 (9%)/11 (16%) | 28 (42%)/22 (33%) | 0.14 |
| Age (years) | 52.2 | 20-77 | 53.6 | 51.1 | 0.60 |
| WBC ($10^6$/l) | 26100 | 1400-342700 | 72742 | 65252 | 0.78 |
| FAB classification |  |  |  |  | 0.81 |
| AML 0, 1, 2, 6, 7, incl | 41 (61%) |  | 10 (15%) | 31 (46%) |  |
| AML 4, 4eo, 5 | 26 (39%) |  | 7 (11%) | 19 (28%) |  |
| Karyotype |  |  |  |  | 0.94 |
| Inv 16, t(8-21) £ | 5 (8%) |  | 1 (1%) | 4 (7%) |  |
| Normal, 12+ or t(8)$ | 33 (54%) |  | 9 (15%) | 24 (39%) |  |
| −5, −7 or +8 § | 23 (38%) |  | 6 (10%) | 17 (28%) |  |
| Complete remission |  |  |  |  | 0.09 |
| No | 15 (22%) |  | 1 (1%) | 14 (21%) |  |
| Yes | 52 (78%) |  | 16 (24%) | 36 (54%) |  |

All these results show that elevated VEGF121 transcripts level as measured in PBMC from AML patients is an independent predictor of poor prognosis in acute myeloid leukemia.

Previous works, using quantitative immunoassays (RIA or ELISA), reported that elevated cellular and circulating levels of total VEGF protein were associated with poor prognosis in leukemias (Dvorak 2002). Serum VEGF levels reflect not only the factor synthesized by tumor cells, but also that released from platelets. Besides, plasma alpha-2 macroglobulin binds VEGF, making it unavailable to several antibodies (Garrido, Saule et al. 1993; Kondo, Asano et al. 1994; Banks, Forbes et al. 1998; Gunsilius, Petzer et al. 1999; Salven, Orpana et al. 1999; George, Eccles et al. 2000). Plasma VEGF is also resulting from the balance of free VEGF and that sequestered by platelets. Finally, platelet activation is very common in acute myeloid leukemia potentially leading to increased plasma VEGF levels unrelated to the blast cell origin.

In a study of 99 AML with high WBC (at least 20×$10^9$/L), Aguayo et al (Aguayo, Estey et al. 1999) reported that increased levels of blood cellular VEGF protein correlated with shorter overall and disease free survival times. These patients with high blast counts allowed the VEGF measurements. Therefore, the sensitivity of the test restricts its use for all AML patients.

Example 5

Expression of VEGF Isoforms in Various Cancers

Patients and Methods

Using the highly sensitive, specific and accurate assays based on quantitative RT-PCR as described in Examples 1 and 2 above, VEGF isoform transcripts (VEGF121, VEGF165, VEGF145, VEGF189, and VEGF206) were measured in primary tumors and normal tissues from unselected patients suffering from breast (n=126), prostate (n=40), colon (n=19) cancers and AML (n=67). VEGF isoform transcripts were quantified in tumor extracts previously to any chemotherapy.

RNA Extraction and Reverse Transcription

Tumor RNAs were extracted using Trizol reagent (Life Technologies, Inc.) as specified by the manufacturer. RNA (1 µg) was processed for cDNA synthesis using superscript II reverse transcriptase (Life technologies, Inc) with random hexamers.

Standard Preparation

VEGF121, VEGF165, VEGF145, VEGF189, and VEGF206 and the two housekeeping genes: TBP and β2 microglobin (β2 m) RNA from normal tissues were amplified by RT-PCR and cloned in TOPO II TA cloning Kit (Invitrogen) following the manufacturer's recommendations. Cloned products were digested with EcoRI (Invitrogen), extracted from 2% agarose gel, purified with the PCR purification Kit (Qiagen). Finally the products were measured in a spectrophotometer, and molecule concentrations were calculated. Standard curves for VEGF121, VEGF165, VEGF145, VEGF189, and VEGF206 and the two housekeeping genes: TBP and β2 m were generated using serial dilutions of cloned products ranging from one to $10^9$ molecules/µl for VEGF121, VEGF165, TBP and β2 m and from 10 to $10^9$ molecules/µl for VEGF145, VEGF189, and VEGF206.

Real-Time Quantitative RT-PCR

To evaluate the relative expression of VEGF isoforms transcripts (VEGF121, VEGF165, VEGF145, VEGF189, and VEGF206), real time quantitative RT-PCR was performed using LightCycler (Roche).: TBP and β2 m (two different housekeeping genes) transcripts were quantified to relatively express our results. VEGF and β2 m primers and fluorescent probes are described in the above examples. TBP primers and probe are the following: TBP forward: 5'-CAC GAA CCA CGG CAC TGA TT-3' (SEQ ID No:16), TBP reverse: 5'-TTT TCT TGC TGC CAG TCT GGA C-3' (SEQ ID No:17), TBP probe: 5'-FAM TGT CGA CAG GAG CCA AGA TTT CTG GC-3' TAMRA (SEQ ID No:18).

Quantitative PCR reaction was carried out with an aliquot of $1/100^{th}$ of the cDNA resulting from reverse transcription, in a 20 µl volume, using 100 nM of the specific hydrolyze probe, 200 nM of the probe flanking appropriate primer pairs, and 18 µl of LC fast start DNA master mix (Roche®).

PCR Conditions for VEGF145 isoform are: Denaturation: 10 min-95° C.; Amplification 45 cycles: 10 s-95° C.; 20 s-60° C.; 10 s-72° C.; Cooling: 30 s-40° C.

PCR Conditions for VEGF 165, VEGF186 and VEGF206 isoforms are: Denaturation: 10 min-95° C.; Amplification 45 cycles 10 s-95° C.; 15 s-60° C.; Cooling: 30 s-40° C.

All experiments were performed in duplicate. All coefficients of variation of Cp values were <1%. The concentrations of unknown samples were then calculated by setting their crossing points to the standard curve.

Results

Characteristics of the patients and evaluation of VEGF isoform transcripts (VEGF121, VEGF165, VEGF145, VEGF189, and VEGF206) are shown in table 6 (AML), table 7 (colon), and table 8 (prostate).

Expression of VEGF121, VEGF165, VEGF189 and VEGF206 transcripts was evaluated by QRT-PCR in PBMC of 67 AML patients, 126 breast tumors, 40 prostate tumors, 19 colon tumors before any treatment (day 0) and in 20 PBMC of healthy participants, 3 normal breast tissues, 32 normal prostate tissues and 19 normal colon tissues. VEGF isoform transcripts (VEGF121, VEGF165, VEGF145, VEGF189, and VEGF206) mRNA were detected in all groups without any selection.

Most median isoform transcripts (VEGF121, VEGF165, VEGF145, VEGF189, and VEGF206) in tumor samples were significantly higher than in normal control samples, see tables 6a (AML), 7a (colon) and 8a (prostate) below.

Prognostic parameters distribution, according to VEGF isoform transcripts (VEGF121, VEGF165, VEGF145, VEGF189, and VEGF206) expression in specific subgroups of patients are depicted in tables 6b and 6c for AML, 7b for colon cancer and 8b for prostate cancer.

Besides, association between the different VEGF isoform transcripts that were analyzed using Spearman correlation coefficients (P) are shown in tables 6d (AML), 7c (colon) and 8c (prostate). For all tumors analyzed (without exception), the inventors found strong associations between different VEGF isoform transcripts levels (VEGF121, VEGF165, VEGF145, VEGF189, and VEGF206), as shown in tables 6d (AML), 7c (colon) and 8c (prostate).

The follow up period was 49.5 months (median) [32.7-51.9] for AML patients, 180 months for breast cancer patients and 169 months for colon cancer patients.

AML & VEGF Isoform Transcripts Expression:

For disease free survival and overall survival, both univariate and multivariate analysis showed that high levels of VEGF165 transcripts in AML patients were significantly related with a worse prognosis (p=0.012 and 0.017 respectively) (FIG. 12A). Indeed, patients could be separated in three groups according to the absolute levels of VEGF165 expression: VEGF165/$10^6$ b2 m group 1: 0 to 72.7, group 2: 72.7 to 229 and group 3: 229 to 9041, which confirmed the continuous relationship between VEGF165 values and prognostic.

The inventors have demonstrated herein that elevated levels of VEGF165 transcripts are indicative of a poor prognosis in acute myeloid leukemias. Indeed, VEGF165 transcripts levels in AML patients >229 copies/$10^6$ of β2 m; $67^{th}$ percentiles are significantly associated to a worse prognosis.

Associations between VEGF165 expression and prognostic parameters (Age, WBC, AML class and Karyotype) are depicted in table 6c. VEGF165 expression is more elevated in patients less than 60 years. No association was found between VEGF165 expression and WBC, nor AML class nor Karyotype.

Associations between VEGF189 expression and prognostic parameters (Age, WBC, AML class and Karyotype) are depicted in table 6c. VEGF189 expression is elevated in PBMC of patients less than 60 years, in patients having more than 6000 WBC and in AML 4, 4 Eo or 5. As shown in table 6g, when adjusted to other known prognostic parameters of AML, VEGF165 and VEGF189 remained good prognostic indicators of event free survival and overall survival (see adjusted hazard ratios of 2.45 and 2.18 for VEGF165, 2.37 and 2.69 for VEGF189, and 2.37 and 3.23 for AML type 4 or 5. Analysing disease free survival, high levels of VEGF189 transcripts were related to a worse prognosis (p=0.008) (FIG. 12B). Indeed, patients were separated in two groups according to the absolute levels of VEGF189 expression: VEGF189/$10^6$b2 m group 1: 0 to 91.3, group 2: 91.3 to 2260. VEGF189 expression was not significantly associated with overall survival (p=0.12).

For VEGF206 expression, patients were separated in two groups, group 1: 0 to 2.0, group 2: 2.0 to 56.7. VEGF206 levels was not predictive of prognosis (disease free and overall survival) (Table 6e).

Global tests to confirm assumption validity of proportional risks are shown in Table 6f, and Cox models adjusted to prognostic factors in Table 6g (non significant parameters are withdrawn).

TABLE 6

| AML Patient's characteristics | |
|---|---|
| | N = 67 |
| Age, median (IQR*) years | 52 (40 to 63) |
| Sex, N (%) female | Non available |
| WBC, median (IQR*) × $10^3$ | 26.1 (8.2 to 75.0) |
| AML, N (%) | |
| 4, 4 Eo or 5 | 26 (39) |
| others | 41 (61) |
| Karyotype, N (%) | |
| 1 | 5 (8) |
| 2 | 33 (54) |
| 3 | 23 (38) |
| Induction treatment, N (%) | |
| 1 | 31 (55) |
| 2 | 14 (25) |
| 3 | 11 (20) |
| Follow-up | |
| Median follow-up, months | 34 |
| No of relapse | 32 |
| No of deaths | 42 |

*IQR: interquartile range

TABLE 6a

Empirical distribution of VEGF isoforms transcripts in
PBMC from AML patients and healthy donors (controls).

| | AML | | | | Control | | | |
|---|---|---|---|---|---|---|---|---|
| | Median | IQR* | Range | MD | Median | IQR* | Range | P† |
| VEGF 121 | | | | | | | | |
| /B2** × $10^6$ | 1090 | 570 to 2055 | 0.1 to 46400 | 8 | 164.9 | 113.5 to 212.8 | 57.6 to 280 | <0.0001 |
| VEGF 165 | | | | | | | | |
| /B2 × $10^6$ | 126.9 | 63.3 to 329.1 | 0 to 9041 | 16 | 128.9 | 99.1 to 141.2 | 62.4 to 206.8 | 0.80 |
| /TBP | 0.46 | 0.26 to 0.62 | 0 to 1.23 | 18 | 0.95 | 0.77 to 1.04 | 0.32 to 1.46 | <0.0001 |
| /mean | 253.8 | 126.7 to 657.7 | 0 to 17920 | 16 | 257.8 | 198.2 to 282.4 | 124.8 to 413.6 | 0.80 |
| VEGF 206 | | | | | | | | |
| /B2 × $10^6$ | 0 | 0 to 3.37 | 0 to 56.7 | 16 | 4.64 | 3.77 to 6.90 | 0 to 32.57 | 0.0019 |
| /TBP | 0 | 0 to 1.16 | 0 to 52.5 | 18 | 3.67 | 2.59 to 5.79 | 0 to 16.64 | 0.0003 |
| /mean | 0 | 0 to 6.73 | 0 to 113.3 | 16 | 9.28 | 7.54 to 13.80 | 0 to 65.13 | 0.0019 |
| VEGF 189 | | | | | | | | |
| /B2 × $10^6$ | 51.6 | 0 to 153.8 | 0 to 2260 | 16 | 32.7 | 28.5 to 45.6 | 18.3 to 295.7 | 0.82 |
| /TBP | 22.8 | 0 to 48.5 | 0 to 862.5 | 18 | 0.25 | 0.21 to 0.36 | 0.13 to 1.51 | 0.58 |
| /mean | 103.1 | 0 to 307.5 | 0 to 4510 | 16 | 65.3 | 57.0 to 91.2 | 36.6 to 591.3 | 0.82 |

*IQR: interquartile range; MD: missing data;
†Comparison of leukemia and control values using Wilcoxon rank-sum tests;
**B2: beta 2 microglobulin
VEGF isoform transcripts values obtained from PBMC of 12 healthy donors were used as controls.

VEGF isoform transcripts values obtained from PBMC of 12 healthy donors were used as controls.

TABLE 6b

Prognostic parameters distribution, according to VEGF isoform
transcripts expression in specific subgroups of patients

| | VEGF 165/B2 | | |
|---|---|---|---|
| | 0 to 72.7 | 72.7 to 229 | 229 to 9041 |
| Age, median (IQR*) ys | 54 (41 to 66) | 48 (21 to 57) | 45 (22 to 62) |
| WBC, median (IQR*) × $10^3$ | 27.4 (1.4 to 108.7) | 22.4 (1.6 to 66.4) | 38.1 (3.6 to 251.8) |
| AML, N (%) | | | |
| 4, 4 Eo or 5 | 6 (35) | 5 (29) | 7 (41) |
| Others | 11 (65) | 12 (71) | 10 (59) |
| Karyotype, N (%) | | | |
| 1 | 0 (0) | 3 (20) | 0 (0) |
| 2 | 9 (56) | 7 (47) | 8 (57) |
| 3 | 7 (44) | 5 (33) | 6 (43) |

| | VEGF 206/B2 | |
|---|---|---|
| | 0 to 2.0 | 2.0 to 56.7 |
| Age, median (IQR*) ys | 46 (39 to 62) | 51 (44 to 67) |
| WBC, median (IQR*) × $10^3$ | 38.0 (14.9 to 96.6) | 15.6 (7.6 to 49.5) |
| AML, N (%) | | |
| 4, 4 Eo or 5 | 13 (38) | 5 (29) |
| Others | 21 (62) | 12 (71) |
| Karyotype, N (%) | | |
| 1 | 2 (7) | 1 (6) |
| 2 | 17 (59) | 7 (44) |
| 3 | 10 (34) | 8 (50) |

TABLE 6b-continued

Prognostic parameters distribution, according to VEGF isoform transcripts expression in specific subgroups of patients

|  | VEGF 189/B2 | |
|---|---|---|
|  | 0 to 91.3 | 91.3 to 2260 |
| Age, median (IQR*) ys | 54 (39 to 63) | 44 (41 to 52) |
| WBC, median (IQR*) × 10³ | 26.1 (6.6 to 75.0) | 44.3 (14.5 to 92.6) |
| AML, N (%) | | |
| 4, 4 Eo or 5 | 12 (35) | 6 (35) |
| Others | 22 (65) | 11 (65) |
| Karyotype, N (%) | | |
| 1 | 2 (7) | 1 (7) |
| 2 | 16 (52) | 8 (57) |
| 3 | 13 (42) | 5 (36) |

TABLE 6c

VEGF isoform transcripts distribution according to prognostic parameters. Data are presented in median (IQR)

|  | N (%) | VEGF 165/B2 | VEGF 206/B2 | VEGF 189/B2 |
|---|---|---|---|---|
| Age | | | | |
| <60 ys | 46 (69) | 132.1 (68.4 to 329.1) | 0 (0 to 3.8) | 65.9 (0 to 175.6) |
| ≧60 ys | 21 (31) | 86.4 (37.9 to 303.1) | 0 (0 to 3.0) | 20.5 (0 to 83.5) |
| WBC | | | | |
| <6000 | 11 (17) | 106.7 (59.9 to 431.8) | 0 (0 to 5.3) | 0 (0 to 57.5) |
| >6000 | 54 (83) | 132.1 (64.2 to 360.4) | 0 (0 to 3.5) | 58.6 (0 to 170.2) |
| AML | | | | |
| 4, 4 Eo or 5 | 26 (39) | 139.5 (66.2 to 540.5) | 0 (0 to 2.5) | 59.8 (0 to 167.1) |
| others | 41 (61) | 113.9 (38.9 to 269.9) | 0 (0 to 4.4) | 0 (0 to 151.2) |
| Karyotype | | | | |
| 1 | 5 (8) | 113.9 (98.7 to 120.4) | 1.5 (0.7 to 29.1) | 71.3 (68.6 to 251.3) |
| 2 | 33 (54) | 139.5 (26.2 to 303.1) | 0 (0 to 2.6) | 0 (0 to 158.6) |
| 3 | 23 (38) | 108.1 (63.6 to 532.3) | 1.2 (0 to 4.7) | 47.6 (0 to 91.8) |

TABLE 6d

Association between the different VEGF isoform transcripts that were analyzed. Spearman correlation coefficients (P)

|  | VEGF165 | VEGF169 |
|---|---|---|
| VEGF165 | — | — |
| VEGF189 | 0.57 (<0.0001) | — |
| VEGF206 | 0.57 (<0.0001) | 0.36 (0.0092) |

TABLE 6e

Association of VEGF isoform transcripts expression to survival (event free and overall survival).

|  |  | Event-free survival | | Survival | |
|---|---|---|---|---|---|
|  | Values | HR (95% CI)* | P | HR (95% CI)* | P |
| VEGF 165 | | | | | |
| /B2 × 10⁶ | 0 to 72.7 | 1 | † | 1 | † |
|  | 72.7 to 229 | 1.28 (0.54 to 3.04) | 0.57 | 1.63 (0.66 to 4.1) | 0.29 |
|  | 229 to 9041 | 2.80 (1.26 to 6.24) | 0.012 | 2.89 (1.20 to 6.70) | 0.017 |

TABLE 6e-continued

Association of VEGF isoform transcripts expression to survival (event free and overall survival).

| | | Event-free survival | | Survival | |
|---|---|---|---|---|---|
| | Values | HR (95% CI)* | P | HR (95% CI)* | P |
| /TBP | 0 to 0.32 | 1 | † | 1 | † |
| | 0.32 to 0.55 | 0.61 (0.26 to 1.41) | 0.24 | 0.61 (0.26 to 1.45) | 0.26 |
| | 0.55 to 1.23 | 0.85 (0.38 to 1.88) | 0.69 | 0.73 (0.31 to 1.71) | 0.47 |
| | | VEGF 206 | | | |
| /B2 × $10^6$ | 0 to 2.0 | 1 | † | 1 | † |
| | 2.0 to 56.7 | 1.00 (0.50 to 1.99) | 1.00 | 1.44 (0.73 to 2.93) | 0.31 |
| /TBP | 0 to 0.83 | 1 | † | 1 | † |
| | 0.83 to 52.5 | 0.87 (0.43 to 1.77) | 0.70 | 1.09 (0.52 to 2.30) | 0.82 |
| | | VEGF 189 | | | |
| /B2 × $10^6$ | 0 to 91.3 | 1 | † | 1 | † |
| | 91.3 to 2260 | 1.82 (0.92 to 3.61) | 0.085 | 1.77 (0.87 to 3.60) | 0.12 |
| /TBP | 0 to 42.6 | 1 | † | 1 | † |
| | 42.6 to 862 | 1.41 (0.70 to 2.85) | 0.34 | 1.49 (0.72 to 3.1) | 0.28 |

*HR: hazard ratio; 95% CI: 95% confidence interval.
†Reference category. Variables were categorized into three equal-sizes categories according to sample $33^{rd}$ and $67^{th}$ percentiles, except when the $33^{rd}$ percentile was equal to the minimum value; in this case data were cut at the $67^{th}$.

TABLE 6f

Global tests to confirm assumption validity of proportional risks

| | Event-free survival | | Survival | |
|---|---|---|---|---|
| | P (global test) | P (PH test) | P (global test) | P (PH test) |
| | VEGF 165 | | | |
| /B2 × $10^6$ | 0.024 | 0.26 | 0.048 | 0.053 |
| /TBP | 0.49 | 0.71 | 0.52 | 0.56 |
| | VEGF 206 | | | |
| /B2 × $10^6$ | 1.00 | 0.94 | 0.31 | 0.38 |
| /TBP | 0.70 | 0.61 | 0.82 | 0.64 |
| | VEGF 189 | | | |
| /B2 × $10^6$ | 0.081 | 0.23 | 0.12 | 0.22 |
| /TBP | 0.33 | 0.99 | 0.28 | 0.65 |

TABLE 6g

Multiple prognosis analysis

| | Event-free survival | | Survival | |
|---|---|---|---|---|
| Variables | aHR (95% CI)* | P | aHR (95% CI)* | P |
| VEGF165/B2 > 229 | 2.45 (1.35 to 5.19) | 0.0046 | 2.18 (1.10 to 4.33) | 0.026 |
| VEGF189/B2 > 91.3 | 2.37 (0.42 to 4.86) | 0.019 | 2.69 (1.23 to 5.89) | 0.013 |
| AML type other than 4 or 5 | 2.37 (0.42 to 5.08) | 0.026 | 3.23 (1.41 to 7.37) | 0.0054 |

*aHR: adjusted hazard ratio; 95% CI: 95% confidence interval.

Colon Cancer & VEGF Isoform Transcripts Levels

VEGF isoform transcripts levels related to b2 m or TBP were quantified in paired tumor tissue and normal counterparts of the same individual. All four isoforms levels were greater in tumors compared to normal tissues (6-fold higher for VEGF121, 9-fold higher for VEGF165, 8-fold higher for VEGF189 and 4-fold higher for VEGF206 (table 7a). VEGF isoforms transcripts distribution according to prognostic parameters is depicted in Table 7b.

Association of VEGF isoform transcript expression to survival (event free and overall survival) is shown in Tables 7d and 7e.

TABLE 7

| Patient's characteristics | |
|---|---|
| | N = 19 |
| Age, median (IQR*) years | 74 (58 to 79) |
| Sex, N (%) female | 8 (42) |
| Stage, N (%) | |
| 1 | 2 (11) |
| 2 | 8 (42) |
| 3 | 3 (5) |
| 4 | 8 (42) |
| Localization, N (%) | |
| CD | 3 (16) |
| CG | 13 (68) |
| Rectum | 3 (16) |
| Surgery, N (%) | 11 (58) |
| Follow-up | |
| Median follow-up | 169 |
| No disease-related deaths | 12 (63) |
| No deaths other causes | 3 (16) |

*IQR: interquartile range

TABLE 7a

Empirical distribution of VEGF isoforms transcripts in paired tumor and normal tissues.

| | Tumor cells | | | Control cells | | | |
|---|---|---|---|---|---|---|---|
| | Median | IQR* | Range | Median | IQR* | Range | P† |
| VEGF 121 | | | | | | | |
| /B2 × $10^6$ | 2151 | 1140 to 2477 | 290 to 12720 | 351 | 280 to 468 | 148 to 4111 | 0.0006 |
| /TBP | 3.70 | 2.65 to 6.15 | 0.50 to 15.50 | 1.90 | 1.30 to 2.60 | 0.80 to 5.80 | 0.031 |
| VEGF 165 | | | | | | | |
| /B2 × $10^6$ | 545 | 410 to 959 | 247 to 4665 | 60 | 29.2 to 96 | 21 to 336 | <0.0001 |
| /TBP | 1.20 | 0.90 to 2.00 | 0.40 to 5.70 | 0.30 | 0.20 to 0.45 | 0.10 to 2.10 | 0.0013 |
| VEGF 206 | | | | | | | |
| /B2 × $10^6$ | 19.96 | 9.80 to 30.62 | 8.22 to 86.77 | 4.63 | 4.04 to 10.18 | 1.54 to 36.58 | 0.0020 |
| /TBP | 3.60 | 2.62 to 5.17 | 0.59 to 10.59 | 3.14 | 2.13 to 4.75 | 1.36 to 11.21 | 0.63 |
| VEGF 189 | | | | | | | |
| /B2 × $10^6$ | 1282 | 1029 to 2739 | 552 to 18190 | 162 | 117 to 250 | 40 to 1186 | <0.0001 |
| /TBP | 3.92 | 2.19 to 6.43 | 0.61 to 22.20 | 0.92 | 0.66 to 1.30 | 0.38 to 2.11 | <0.0001 |

*IQR: interquartile range; MD: missing data;
†Comparison of tumor and control cells using paired Wilcoxon rank-sum tests TABLE 7b VEGF isoform transcripts distribution according to prognostic parameters. Data are presented in median (IQR)

| | N (%) | VEGF 121/B2 | VEGF 165/B2 | VEGF 206/B2 | VEGF 189/B2 |
|---|---|---|---|---|---|
| Age | | | | | |
| <75 ys | 10 (53) | 1844 (1165 to 4978) | 817.2 (517.9 to 1487) | 26.4 (10.2 to 31.8) | 1518 (1013 to 3355) |
| ≧75 ys | 9 (47) | 2339 (1154 to 2465) | 431.4 (336.6 to 643.0) | 20.0 (10.0 to 24.7) | 1282 (1070 to 2687) |
| Sex | | | | | |
| Female | 8 (42) | 1939 (1301 to 2394) | 471.6 (375.0 to 720.0) | 16.4 (9.6 to 24.4) | 1713 (1045 to 2713) |
| Male | 11 (58) | 2151 (1115 to 2519) | 697.3 (450.5 to 959.2) | 21.3 (10.9 to 31.6) | 1282 (921 to 2850) |
| Stage | | | | | |
| 1-2 | 10 (53) | 1939 (1133 to 2439) | 539.9 (360.1 to 960.7) | 22.3 (13.4 to 32.5) | 1584 (1080 to 2665) |
| 3-4 | 9 (47) | 2151 (1350 to 2490) | 509.0 (434.1 to 937.1) | 11.9 (9.6 to 21.9) | 1228 (998 to 2687) |
| Surgery | | | | | |
| No | 8 (42) | 2153 (1380 to 3461) | 603.2 (449.1 to 1119) | 16.6 (9.9 to 23.7) | 1518 (1052 to 2976) |
| Yes | 11 (58) | 1538 (1115 to 2414) | 544.7 (383.9 to 959.2) | 20.0 (11.2 to 32.3) | 1282 (916 to 2539) |

TABLE 7c

Association between the different VEGF isoform transcripts that were analyzed. Spearman correlation coefficients (P)

| | VEGF121 | VEGF165 | VEGF189 |
|---|---|---|---|
| VEGF165 | 0.66 (0.0021) | — | — |
| VEGF189 | 0.85 (<0.0001) | 0.69 (0.0014) | — |
| VEGF206 | 0.76 (0.0003) | 0.64 (0.0037) | 0.87 (<0.0001) |

TABLE 7d

Association of VEGF isoform transcripts expression to survival

| | | Values | Survival HR (95% CI)* | P |
|---|---|---|---|---|
| VEGF 121 | | | | |
| /B2 × $10^6$ | | 0 to 2151 | 1 | † |
| | | 2151 to 12720 | 1.30 (0.41 to 4.14) | 0.65 |
| /TBP | | 0 to 3.7 | 1 | † |
| | | 3.7 to 15.5 | 1.15 (0.37 to 3.59) | 0.80 |
| VEGF 165 | | | | |
| /B2 × $10^6$ | | 0 to 545 | 1 | † |
| | | 545 to 4665 | 1.18 (0.37 to 3.70) | 0.78 |
| /TBP | | 0 to 1.20 | 1 | † |
| | | 1.20 to 5.70 | 1.05 (0.34 to 3.28) | 0.93 |
| VEGF 206 | | | | |
| /B2 × $10^6$ | | 0 to 19.96 | 1 | † |
| | | 19.96 to 86.77 | 1.05 (0.33 to 3.33) | 0.93 |
| /TBP | | 0 to 3.60 | 1 | † |
| | | 3.60 to 10.59 | 0.63 (0.20 to 2.04) | 0.44 |
| VEGF 189 | | | | |
| /B2 × $10^6$ | | 0 to 1282 | 1 | † |
| | | 1282 to 18190 | 1.45 (0.43 to 3.44) | 0.55 |

TABLE 7d-continued

Association of VEGF isoform transcripts expression to survival

| | Values | Survival HR (95% CI)* | P |
|---|---|---|---|
| /TBP | 0 to 3.92 | 1 | † |
| | 3.92 to 22.20 | 1.32 (0.39 to 4.45) | 0.65 |

*HR: hazard ratio; 95% CI: 95% confidence interval.
† Reference category. Due to sample size, variables were categorized into two equal-sizes categories according to sample median.

TABLE 7e

Global tests to confirm assumption validity of proportional risks

| | Survival P (global test) | P (PH test) |
|---|---|---|
| | VEGF 121 | |
| /B2 × $10^6$ | 0.65 | 0.68 |
| /TBP | 0.80 | 0.72 |
| | VEGF 165 | |
| /B2 × $10^6$ | 0.78 | 0.76 |
| /TBP | 0.93 | 0.96 |
| | VEGF 206 | |
| /B2 × $10^6$ | 0.93 | 0.47 |
| /TBP | 0.44 | 0.084 |
| | VEGF 189 | |
| /B2 × $10^6$ | 0.55 | 0.14 |
| /TBP | 0.35 | 0.038 |

Prostate Cancer & VEGF Isoform Transcripts Levels 40 patients included in this study had VEGF isoform transcripts measurements on tumor tissues. 32/40 of these patients had measurements on paired tumor and normal tissue. The differences between normal and tumor VEGF isoform transcripts values were tested on 32 patients' population. Conversely, VEGF isoform transcripts values association to prognostic parameters was studied on the whole population (n=40).

VEGF isoform transcripts distribution according to prognostic parameters is depicted in Table 8b.

TABLE 8

Patient's characteristics

| | N = 40 |
|---|---|
| Age, median (IQR*) ys | 62 (58 to 67) |
| PSA, median (IQR*) | 7.5 (6.4 to 10) |
| Stage, N (%) | |
| T2 | 20 (50) |
| T3 | 20 (50) |
| Gleason T, median (IQR*) | 7 (6.75 to 7) |
| Gleason max, median (IQR*) | 3 (3 to 4) |
| GG, N (%) | |
| N0 | 10 (25) |
| NX | 30 (75) |
| Prostate weight, median (IQR*) g | 40 (36 to 46) |

*IQR: interquartile range

TABLE 8a

Empirical distribution of VEGF isoforms transcripts in paired tumor and normal tissues.

| | Tumor cells | | | Control cells | | | |
|---|---|---|---|---|---|---|---|
| | Median | IQR* | Range | Median | IQR* | Range | P† |
| | VEGF 121 | | | | | | |
| /B2 × $10^6$ | 4433 | 1528 to 7747 | 65 to 22560 | 2053 | 818 to 3215 | 436 to 10250 | 0.0028 |
| /TBP | | 2.52 1.53 to 3.49 | 0.01 to 14.48 | | 1.31 0.68 to 2.38 | 0.29 to 9.95 | 0.031 |
| | VEGF 165 | | | | | | |
| /B2 × $10^6$ | 5106 | 2685 to 7468 | 526 to 17210 | 2627 | 865 to 4769 | 308 to 15790 | 0.0044 |
| /TBP | | 2.28 1.82 to 4.80 | 0.24 to 11.04 | | 1.10 0.65 to 3.45 | 0.30 to 8.87 | 0.027 |
| | VEGF 206 | | | | | | |
| /B2 × $10^6$ | 57.9 | 24.2 to 134.3 | 0 to 2336 | 27.6 | 9.6 to 53.9 | 0 to 517.5 | 0.049 |
| /TBP | | 3.92 1.81 to 7.94 | 0 to 254.6 | | 2.23 1.01 to 5.57 | 0 to 26.8 | 0.12 |
| | VEGF 189 | | | | | | |
| /B2 × $10^6$ | 775 | 291 to 1601 | 0 to 4881 | 445 | 255 to 775 | 0 to 8951 | 0.043 |
| /TBP | | 48.5 28.1 to 72.7 | 0 to 532 | | 32.7 19.5 to 45.1 | 0 to 300 | 0.24 |

*IQR: interquartile range; MD: missing data;
†Comparison of tumor and control cells using paired Wilcoxon rank-sum tests TABLE 8b VEGF isoform transcripts distribution according to prognostic parameters. Data are presented in median (IQR)

| | N (%) | VEGF 121/B2 | VEGF 165/B2 | VEGF 206/B2 | VEGF 189/B2 |
|---|---|---|---|---|---|
| Age | | | | | |
| ≦60 ys | 14 (35) | 5877 (2030 to 10230) | 5713 (3180 to 7976) | 64.3 (15.4 to 116.1) | 837 (314 to 1577) |
| >60 ys | 26 (65) | 5134 (2187 to 8153) | 4869 (2799 to 8493) | 79.1 (32.4 to 147.0) | 880 (434 to 1446) |
| PSA | | | | | |
| 0 to 9 | 26 (65) | 5833 (2578 to 8361) | 5496 (3250 to 7531) | 73.7 (26.7 to 142.4) | 1009 (457 to 1593) |
| 10+ | 14 (35) | 4422 (1268 to 9389) | 2781 (1836 to 11500) | 79.7 (44.4 to 140.1) | 430 (257 to 1225) |
| Stage | | | | | |
| T2 | 20 (50) | 5693 (2395 to 7754) | 5713 (2961 to 7468) | 33.1 (24.2 to 83.5) | 775 (431 to 1492) |
| T3 | 20 (50) | 5703 (1974 to 11440) | 4670 (2660 to 13250) | 106 (57.9 to 200) | 987 (379 to 1651) |
| Gleason T | | | | | |
| 2 to 6 | 10 (25) | 4368 (1338 to 6525) | 6208 (2547 to 7355) | 41.9 (16.9 to 99.4) | 733 (399 to 1161) |
| 7 to 10 | 30 (75) | 5828 (2521 to 10110) | 4869 (2905 to 9465) | 79.1 (32.4 to 158.7) | 880 (414 to 1577) |
| Weight | | | | | |
| ≦40 g | 21 (54) | 5134 (748 to 8354) | 4479 (2366 to 11840) | 39.1 (11.2 to 117.5) | 775 (333 to 1617) |
| >40 g | 18 (46) | 6180 (2578 to 9111) | 6495 (3560 to 8195) | 79.7 (32.3 to 148.6) | 965 (430 to 1486) |
| GG, N (%) | | | | | |
| N0 | 10 (25) | 5153 (1861 to 13520) | 5660 (1860 to 12300) | 106 (79.4 to 147) | 1090 (320 to 1446) |
| NX | 30 (75) | 5698 (2799 to 8493) | 5106 (3011 to 7510) | 49.6 (25.9 to 128.1) | 775 (434 to 1577) |

TABLE 8c

Association between the different VEGF isoform transcripts that were analyzed. Spearman correlation coefficients (P)

| | VEGF121 | VEGF165 | VEGF189 |
|---|---|---|---|
| VEGF165 | 0.95 (<0.0001) | — | — |
| VEGF189 | 0.75 (<0.0001) | 0.77 (<0.0001) | — |
| VEGF206 | 0.49 (0.0015) | 0.40 (0.012) | 0.45 (0.0040) |

Breast Cancer & VEGF Isoform Transcripts Levels 126 patients whose breast tumors were excised were included in this study. The follow up period was =180 months. 44 (35%) patients have relapsed within this period after surgery. The relapse events consisted of local and/or regional recurrences, metastasis and/or both events.

To visualize the capacity of target gene transcript levels to discriminate between patients who relapsed and those who did not relapse (in absence of an arbitrary cutoff value), the receiver-operating characteristic (ROC)—area under the curve (AUC) method was used (Hanley and McNeil 1982). The best cutoff point has been determined from the ROC curve; it corresponds to the tangent of the curve.

VEGF isoform transcripts cutoff were:
VEGF121 cutoff=5.1
VEGF165 cutoff=7.3
VEGF165/121 cutoff=3.

Patients were separated in two groups according to the AUC method: VEGF121/TBP group 1: 0 to 5.1, group 2: > 5.1. VEGF165/TBP group 1: 0 to 7.3, group 2: >7.3. No association was found between VEGF189 and VEGF206 transcripts levels (related to TBP) and prognosis prediction.

Figure 13A:
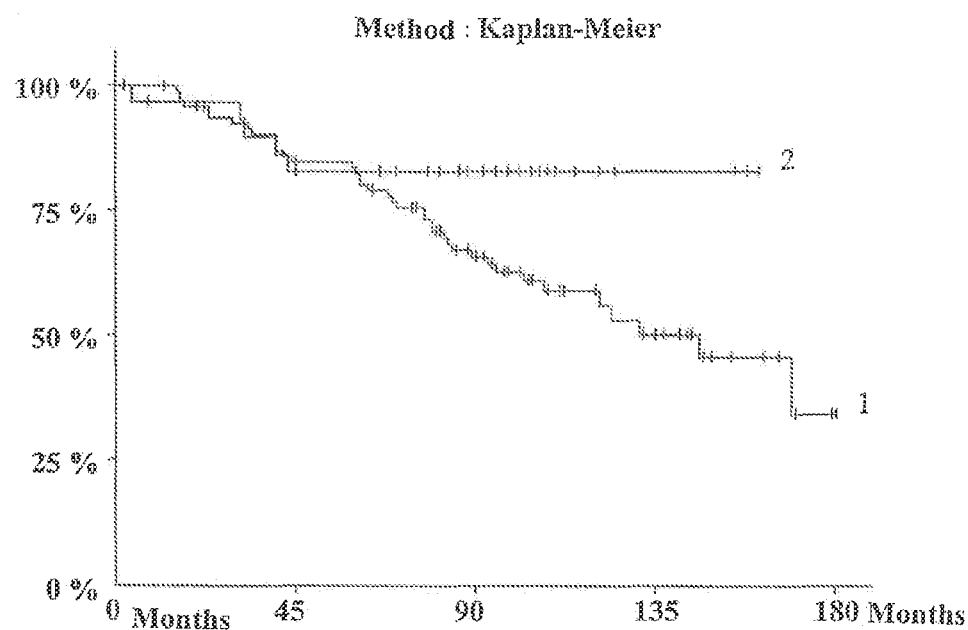
Figure 13B:
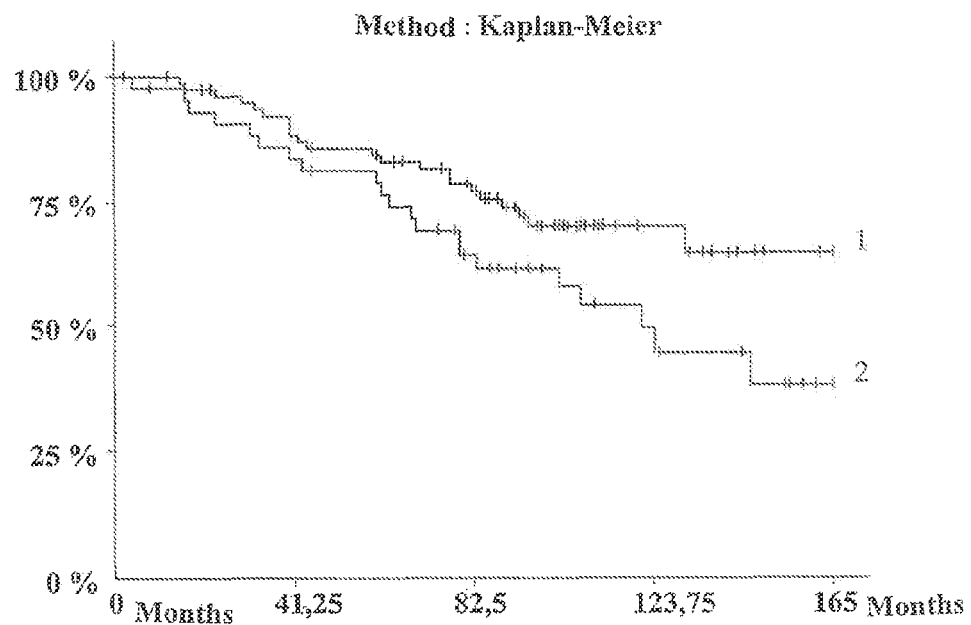
Figure 13C:
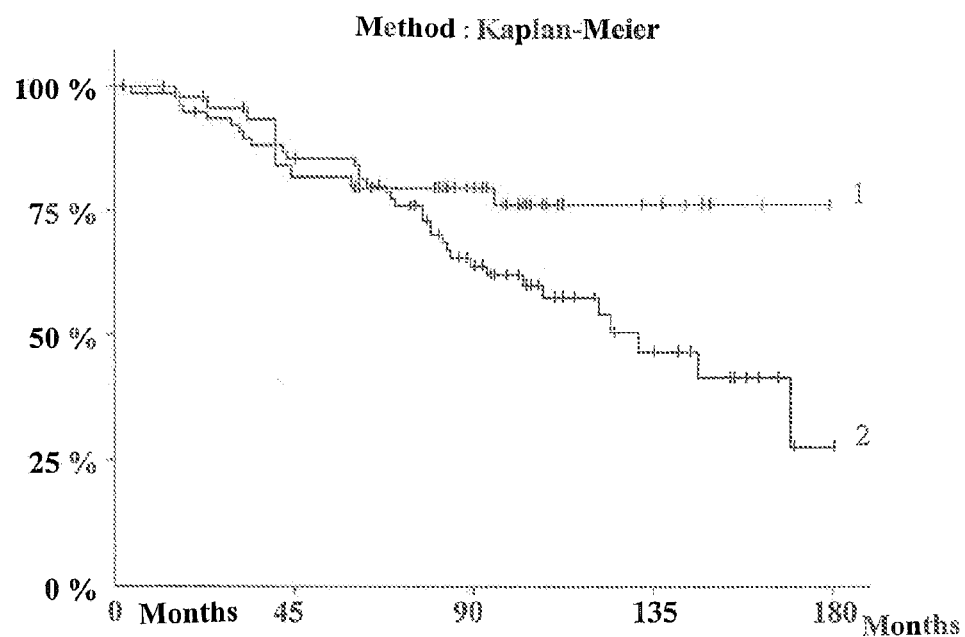
Figure 13D:
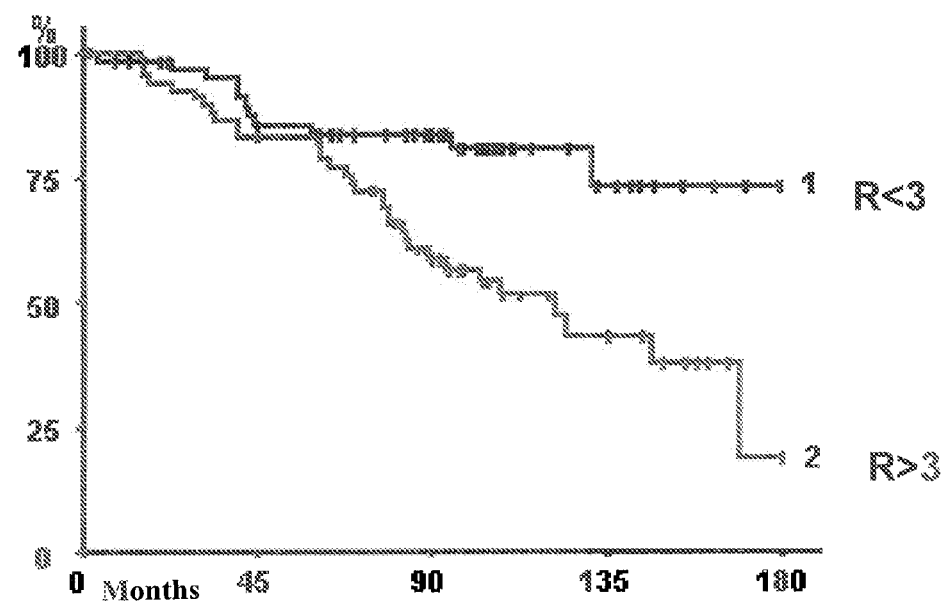

Disease free survival analyses revealed that high levels of VEGF121 transcripts were related to a good prognosis (p=0.064) (FIG. 13A) while high VEGF165 transcripts levels were associated to a bad prognosis (p=0.049) (FIGS. 13B & 13C). As a consequence and most importantly, VEGF165/VEGF121 elevated ratio is strongly associated with worse prognosis (p=0.0028) (FIG. 13D).

Patients could be separated in three groups according to the absolute levels of VEGF165/VEGF121 expression: VEGF165/VEGF121 group 1: <2.03, group 2: 2.03<x<5.3 and group 3: >5.30, which confirmed the continuous relationship between VEGF165/VEGF121 ratio values and prognostic (p=0.031). Most importantly, this transcript ratio is completely independent from endogenous controls. Indeed, the same results were obtained using 3 different housekeeping genes (TBP, b2 m and PPIA). This result provides a very important advantage for Q-RT-PCR assays.

Conclusion

A large body of experiments has demonstrated that VEGF is the main regulator of tumor angiogenesis. This was confirmed in 2003 by the demonstration of the efficacy of a humanized anti-VEGF antibody (Avastin) in phase III clinical trials on colorectal cancer. The rationale behind the anti-angiogenic therapeutic agents currently undergoing pre-clinical or clinical trials is that if an angiogenic factor and/or its receptors are over-expressed in pathological angiogenesis, then decreasing their bioavailability should be enough to eradicate tumor vessels and invasion. They emphasize the important part that VEGF plays in cancers. The present work brings new insights for a specific role of the VEGF soluble isoforms transcripts.

All the data presented herein performed with highly sensitive and specific assays were obtained from unselected patients. The present findings support the use of these assays as predictive and prognostic tools helping the physician to select and follow up patients more susceptible to benefit from new anti-angiogenic alternative therapeutic strategies.

REFERENCES

Adams, J., P. J. Carder, et al. (2000). "Vascular endothelial growth factor (VEGF) in breast cancer: comparison of plasma, serum, and tissue VEGF and microvessel density and effects of tamoxifen." *Cancer Res* 60(11): 2898-905.

Aguayo, A., E. Estey, et al. (1999). "Cellular vascular endothelial growth factor is a predictor of outcome in patients with acute myeloid leukemia." *Blood* 94(11): 3717-21.

Aguayo, A., H. Kantarjian, et al. (2000). "Angiogenesis in acute and chronic leukemias and myelodysplastic syndromes." *Blood* 96(6): 2240-5.

Banks, R. E., M. A. Forbes, et al. (1998). "Release of the angiogenic cytokine vascular endothelial growth factor (VEGF) from platelets: significance for VEGF measurements and cancer biology." *Br J Cancer* 77(6): 956-64.

de Bont, E. S., V. Fidler, et al. (2002). "Vascular endothelial growth factor secretion is an independent prognostic factor for relapse-free survival in pediatric acute myeloid leukemia patients." *Clin Cancer Res* 8(9): 2856-61.

Di Raimondo, F., M. P. Azzaro, et al. (2000). "Angiogenic factors in multiple myeloma: higher levels in bone marrow than in peripheral blood." *Haematologica* 85(8): 800-5.

Dias, S., S. V. Shmelkov, et al. (2002). "VEGF(165) promotes survival of leukemic cells by Hsp90-mediated induction of Bcl-2 expression and apoptosis inhibition." *Blood* 99(7): 2532-40.

Dvorak, H. F. (2002). "Vascular permeability factor/vascular endothelial growth factor: a critical cytokine in tumor angiogenesis and a potential target for diagnosis and therapy." *J Clin Oncol* 20(21): 4368-80.

Ferrara, N. and T. Davis-Smyth (1997). "The biology of vascular endothelial growth factor." *Endocr Rev* 18(1): 4-25.

Ferrara, N., H. P. Gerber, et al. (2003). "The biology of VEGF and its receptors." *Nat Med* 9(6): 669-76.

Fiedler, W., U. Graeven, et al. (1997). "Vascular endothelial growth factor, a possible paracrine growth factor in human acute myeloid leukemia." *Blood* 89(6): 1870-5.

Fiedler, W., R. Mesters, et al. (2003). "A phase 2 clinical study of SU5416 in patients with refractory acute myeloid leukemia." *Blood* 102(8): 2763-7.

Foekens, J. A., H. A. Peters, et al. (2001). "High tumor levels of vascular endothelial growth factor predict poor response to systemic therapy in advanced breast cancer." *Cancer Res* 61(14): 5407-14.

Folkman, J. (1997). "Angiogenesis and angiogenesis inhibition: an overview." *Exs* 79: 1-8.

Garrido, C., S. Saule, et al. (1993). "Transcriptional regulation of vascular endothelial growth factor gene expression in ovarian bovine granulosa cells." *Growth Factors* 8(2): 109-17.

George, M. L., S. A. Eccles, et al. (2000). "Correlation of plasma and serum vascular endothelial growth factor levels with platelet count in colorectal cancer: clinical evidence of platelet scavenging?" *Clin Cancer Res* 6(8): 3147-52.

Gunsilius, E., A. L. Petzer, et al. (1999). "Correspondence re: P. Salven et al., leukocytes and platelets of patients with cancer contain high levels of vascular endothelial growth factor. Clin. Cancer Res., 5: 487-91, 1999." *Clin Cancer Res* 5(10): 2978-9.

Hanley, J. A. and B. J. McNeil (1982). "The meaning and use of the area under a receiver operating characteristic (ROC) curve." *Radiology* 143(1): 29-36.

Jeng, K. S., 1. S. Sheen, et al. (2004). "Prognostic significance of preoperative circulating vascular endothelial growth factor messenger RNA expression in resectable hepatocellular carcinoma: a prospective study." *World J Gastroenterol* 10(5): 643-8.

Kondo, S., M. Asano, et al. (1994). "Vascular endothelial growth factor/vascular permeability factor is detectable in the sera of tumor-bearing mice and cancer patients." *Biochim Biophys Acta* 1221(2): 211-4.

Konecny, G. E., Y. G. Meng, et al. (2004). "Association between HER-2/neu and vascular endothelial growth factor expression predicts clinical outcome in primary breast cancer patients." *Clin Cancer Res* 10(5): 1706-16.

Litwin, C., K. G. Leong, et al. (2002). "Role of the microenvironment in promoting angiogenesis in acute myeloid leukemia." *Am J Hematol* 70(1): 22-30.

Moehler, T. M., A. D. Ho, et al. (2003). "Angiogenesis in hematologic malignancies." *Crit Rev Oncol Hematol* 45(3): 227-44.

Padro, T., R. Bieker, et al. (2002). "Overexpression of vascular endothelial growth factor (VEGF) and its cellular receptor KDR (VEGFR-2) in the bone marrow of patients with acute myeloid leukemia." *Leukemia* 16(7): 1302-10.

Padro, T., S. Ruiz, et al. (2000). "Increased angiogenesis in the bone marrow of patients with acute myeloid leukemia." *Blood* 95(8): 2637-44.

Perez-Atayde, A. R., S. E. Sallan, et al. (1997). "Spectrum of tumor angiogenesis in the bone marrow of children with acute lymphoblastic leukemia." *Am J Pathol* 150(3): 815-21.

Poltorak, Z., T. Cohen, et al. (1997). "VEGF145, a secreted vascular endothelial growth factor isoform that binds to extracellular matrix." *J Biol Chem* 272(11): 7151-8.

Salven, P., A. Orpana, et al. (1999). "Leukocytes and platelets of patients with cancer contain high levels of vascular endothelial growth factor." *Clin Cancer Res* 5(3): 487-91.

Salven, P., A. Orpana, et al. (2000). "Simultaneous elevation in the serum concentrations of the angiogenic growth factors VEGF and bFGF is an independent predictor of poor prognosis in non-Hodgkin lymphoma: a single-institution study of 200 patients." *Blood* 96(12): 3712-8.

Shen, G. H., M. Ghazizadeh, et al. (2000). "Prognostic significance of vascular endothelial growth factor expression in human ovarian carcinoma." *Br J Cancer* 83(2): 196-203.

Tabone, M. D., J. Landman-Parker, et al. (2001). "Are basic fibroblast growth factor and vascular endothelial growth factor prognostic indicators in pediatric patients with malignant solid tumors?" *Clin Cancer Res* 7(3): 538-43.

Toi, M., S. Hoshina, et al. (1994). "Association of vascular endothelial growth factor expression with tumor angiogenesis and with early relapse in primary breast cancer." *Jpn J Cancer Res* 85(10): 1045-9.

Van Trappen, P. O., A. Ryan, et al. (2002). "A model for co-expression pattern analysis of genes implicated in angiogenesis and tumour cell invasion in cervical cancer." *Br J Cancer* 87(5): 537-44.

Vincenti, V., C. Cassano, et al. (1996). "Assignment of the vascular endothelial growth factor gene to human chromosome 6p21.3." *Circulation* 93(8): 1493-5.

Wei, M. H., N. C. Popescu, et al. (1996). "Localization of the human vascular endothelial growth factor gene, VEGF, at chromosome 6p12." *Hum Genet* 97(6): 794-7.

Wellmann, S., T. Taube, et al. (2001). "Specific reverse transcription-PCR quantification of vascular endothelial growth factor (VEGF) splice variants by LightCycler technology." *Clin Chem* 47(4): 654-60.

Zhao, W. L., S. Mourah, et al. (2004). "Vascular endothelial growth factor-A is expressed both on lymphoma cells and endothelial cells in angioimmunoblastic T-cell lymphoma and related to lymphoma progression." *Lab Invest* 84(11): 1512-9.

The invention claimed is:

1. An in vitro method for establishing a prognosis concerning a patient suffering from acute myeloid leukaemia, comprising:
   isolating peripheral blood mononucleated cells from a blood sample from said patient;
   extracting RNA from said peripheral blood mononucleated cells;
   measuring the level of VEGF121 transcript in said peripheral blood mononucleated cells a real-time quantitative reverse transcription-polymerase chain reaction (QRT-PCR), wherein the first primer used for amplification comprises at least 15 consecutive nucleotides from exon 4, and wherein the second primer spans the junction between exons 5 and 8 and comprises at least a sequence complementary to the sequence 5'- GAAAAATGT-GAC-3' (SEQ ID No: 8); and determining a prognosis based on the level of VEGF121.

2. The method according to claim 1, further comprising measuring the level of VEGF 165 and/or VEGF189 transcripts in the isolated peripheral blood mononucleated cells by a real-time quantitative reverse transcription-polymerase chain reaction (QRT-PCR), wherein the first primer used for amplification comprises at least 15 consecutive nucleotides from exon 4, and wherein the second primer and/or the probe are as follows:
   for quantifying VEGF165 transcripts, the second primer comprises at least 15 consecutive nucleotides from exon 7, and the probe spans the junction between exons 5 and 7 and comprises at least the sequence 5'-gAAAATC-CCTg-3' (SEQ IDNo: 19);
   for quantifying VEGF189 transcripts, the second primer spans the junction between exons 6a and 7 and comprises at least the sequence 5'-CAgggAACgC-3' (SEQ ID No: 20).

3. A method for monitoring the antiangiogenic treatment of a patient suffering from a disease selected from the group consisting of acute myeloid leukemia, breast cancer and prostate cancer, and undergoing an antiangiogenic treatment, said method comprising the steps of:
   (i) selectively quantifying transcripts encoding VEGF isoforms selected amongst VEGF165, VEGF121, VEGF189, VEGF145 and VEGF206 in a biological sample from said patient, comprising performing a real-time quantitative reverse transcription-polymerase chain reaction (QRT-PCR), wherein the first primer used for amplification comprises at least 15 consecutive nucleotides from exon 4, and wherein the second primer and/or the probe are as follows:

for quantifying VEGF165 transcripts, the second primer comprises at least 15 consecutive nucleotides from exon 7, and the probe spans the junction between exons 5 and 7 and comprises at least the sequence 5'-gAAAATC-CCTg-3' (SEQ ID No: 19);

for quantifying VEGF121 transcripts, the second primer spans the junction between exons 5 and 8 and comprises at least a sequence complementary to the sequence 5'-GAAAAATGTGAC-3' (SEQ ID No: 8);

for quantifying VEGF189 transcripts, the second primer spans the junction between exons 6a and 7 and comprises at least the sequence 5'-CAgggAACgC-3' (SEQ ID No: 20);

for quantifying VEGF145 transcripts, the second primer spans the junction between exons 6a and 8 and comprises at least the sequence 5'-CACATACgC-3' (SEQ ID No: 21);

for quantifying VEGF206 transcripts, the second primer spans the junction between exons 6a and 6b and comprises at least the sequence 5'-CgTACACgC-3' (SEQ ID No:22); and (ii) monitoring the antiangiogenic treatment of a patient based on the level of the VEGF isoform(s).

4. A method for determining a treatment regimen of a patient suffering from a cancer selected from the group consisting of acute myeloid leukemia, breast cancer and prostate cancer, said method comprising the steps of:

(i) selectively quantifying transcripts encoding VEGF isoforms selected amongst VEGF165, VEGF121, VEGF189, VEGF145 and VEGF206 in a biological sample from said patient, comprising performing a real-time quantitative reverse transcription-polymerase chain reaction (QRT-PCR), wherein the first primer used for amplification comprises at least 15 consecutive nucleotides from exon 4, and wherein the second primer and/or the probe are as follows:

for quantifying VEGF165 transcripts, the second primer comprises at least 15 consecutive nucleotides from exon 7, and the probe spans the junction between exons 5 and 7 and comprises at least the sequence 5'-gAAAATC-CCTg-3' (SEQ ID No: 19);

for quantifying VEGF121 transcripts, the second primer spans the junction between exons 5 and 8 and comprises at least a sequence complementary to the sequence 5'-GAAAAATGTGAC-3' (SEQ ID No: 8);

for quantifying VEGF189 transcripts, the second primer spans the junction between exons 6a and 7 and comprises at least the sequence 5'-CAgggAACgC-3' (SEQ ID No: 20);

for quantifying VEGF145 transcripts, the second primer spans the junction between exons 6a and 8 and comprises at least the sequence 5'-CACATACgC-3' (SEQ ID No: (21); for quantifying VEGF206 transcripts, the second primer spans the junction between exons 6a and 6b and comprises at least the sequence 5'-CgTACACgC-3' (SEQ ID No:22); and (ii) determining a treatment regimen based on the levels of the VEGF isoform(s).

5. An in vitro method for establishing a prognosis concerning a patient having a solid breast tumor, comprising:

measuring the level of VEGF 121 and VEGF 165 transcripts in a biopsy from said tumor by a real-time quantitative reverse transcription-polymerase chain reaction (QRT-PCR), wherein the first primer used for amplification comprises at least 15 consecutive nucleotides from exon 4, and wherein the second primer and/or the probe are as follows:

for quantifying VEGF165 transcripts, the second primer comprises at least 15 consecutive nucleotides from exon 7, and the probe spans the junction between exons 5 and 7 and comprises at least the sequence 5'-gAAAATC-CCTg-3' (SEQ ID No: 19);

for quantifying VEGF121 transcripts, the second primer spans the junction between exons 5 and 8 and comprises at least a sequence complementary to the sequence 5'-GAAAAATGTGAC-3' (SEQ ID No: 8);

calculating the VEGF165/VEGF121 ratio; and determining a prognosis based on the VEGF165/VEGF121 ratio.

6. The method according to claim 5, further comprising determining that the patient has a poor prognosis when a VEGF165/VEGF121 ratio is greater than 3.

7. A method for determining if a patient having a solid breast tumor needs an antiangiogenic treatment, comprising:

measuring in vitro the level of VEGF121 and VEGF165 transcripts in a biopsy from said tumor, wherein measuring the level of VEGF121 and VEGF165 transcripts is performed by a real-time quantitative reverse transcription-polymerase chain reaction (QRT-PCR), wherein the first primer used for amplification comprises at least 15 consecutive nucleotides from exon 4, and wherein the second primer and/or the probe are as follows:

for quantifying VEGF165 transcripts, the second primer comprises at least 15 consecutive nucleotides from exon 7, and the probe spans the junction between exons 5 and 7 and comprises at least the sequence 5'-gAAAATC-CCTg-3' (SEQ ID No: 19);

for quantifying VEGF121 transcripts, the second primer spans the junction between exons 5 and 8 and comprises at least a sequence complementary to the sequence 5'-GAAAAATGTGAC-3' (SEQ ID No: 8):

calculating the VEGF165/VEGF121 ratio; and determining that the patient needs antiangiogenic treatment when the VEGF165/VEGF121 ratio is greater than 2.

8. An in vitro method for establishing a prognosis concerning a patient having a solid breast tumor comprising:

measuring the level of VEGF121 and Tatabox-binding protein (TBP) transcripts in a biopsy from said tumor; wherein measuring the level of VEGF121 is carried out by a real-time quantitative reverse transcription-polymerase chain reaction (QRT-PCR), wherein the first primer used from amplification comprises at least 15 consecutive nucleotides from exon 4, the second primer spans the junction between exons 5 and 8 and comprises at least a sequence complementary to the sequence 5'-GAAAAATGTGAC-3' (SEQ ID No: 8);

calculating the VEGF121/TBP ratio; and determining that the patient has a good prognosis when a VEGF121/TBP ratio is greater than 5.1.

* * * * *

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aggccagcac ataggagaga t                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcggcttgt cacattttc                                                 20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagcttccta cagcacaaca aa                                             22

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tgcagaccaa agaaagatag agcaagaca                                      29

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgctccgtgg ccttagc                                                   17

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 6
gagtacgctg gatagcctcc a                                           21

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tgctcgcgct actctctctt tctggc                                      26

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gaaaaatgtg ac                                                     12

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctttctccg ctctgagca                                              19

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
agcaagacaa gaaaatccct gtgggcc                                     27

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttgtcacat acgctccagg ac                                          22

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
```

```
aaacgaaagc gcaagaaatc ccggta                                           26

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccacagggaa cgctccagga c                                                21

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
agcaagacaa gaaaaaaaat cagttcgagg aaa                                   33

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caccaacgta cacgctccag g                                                21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cacgaaccac ggcactgatt                                                  20

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttttcttgct gccagtctgg ac                                               22

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tgtcgacagg agccaagatt tctggc                                           26
```

```
<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gaaaatccct g                                                          11

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagggaacgc                                                            10

<210> SEQ ID NO 21
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 cacatacgc                                                              9

<210> SEQ ID NO 22
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 cgtacacgc                                                              9

<210> SEQ ID NO 23
<211> LENGTH: 1651
<212> TYPE: DNA
<213> ORGANISM: Homo sapiens

<400> SEQUENCE: 23
tcgcggaggc ttggggcagc cgggtagctc ggaggtcgtg gcgctggggg ctagcaccag       60
cgctctgtcg ggaggcgcag cggttaggtg gaccggtcag cggactcacc ggccagggcg      120
ctcggtgctg gaatttgata ttcattgatc cgggttttat ccctcttctt ttttcttaaa      180
catttttttt taaaactgta ttgtttctcg ttttaattta ttttttgcttg ccattcccca     240 cttgaatcgg gccgacggct tggggagatt gctctacttc cccaaatcac tgtggatttt      300
ggaaaccagc agaaagagga aagaggtagc aagagctcca gagagaagtc gaggaagaga      360
gagacggggt cagagagagc gcgcgggcgt gcgagcagcg aaagcgacag gggcaaagtg      420
agtgacctgc ttttgggggt gaccgccgga gcgcggcgtg agccctcccc cttgggatcc      480
cgcagctgac cagtcgcgct gacgacagac agacagaca ccgcccccag ccccagctac       540
cacctcctcc ccggccggcg gcggacagtg gacgcggcgg cgagccgcgg gcaggggccg      600
```

```
gagcccgcgc ccggaggcgg ggtggagggg gtcgggctc gcggcgtcgc actgaaactt      660
ttcgtccaac ttctgggctg ttctcgcttc ggaggagccg tggtccgcgc ggggggaagcc    720 gagccgagcg gagccgcgag aagtgctagc tcgggccggg aggagccgca gccggaggag    780
ggggaggagg aagaagagaa ggaagaggag agggggccgc agtggcgact cggcgctcgg    840
aagccgggct catggacggg tgaggcgcg gtgtgcgcag acagtgctcc agccgcgcgc     900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa tccctgtggg ccttgctcag agcggagaaa gcatttgttt    1500
gtacaagatc cgcagacgtg taaatgttcc tgcaaaaaca cagactcgcg ttgcaaggcg    1560
aggcagcttg agttaaacga acgtacttgc agatgtgaca agccgaggcg gtgagccggg    1620
caggaggaag gagcctccct cagggtttcg g                                   1651

<210> SEQ ID NO 24
<211> LENGTH: 1519
<212> TYPE: DNA
<213> ORGANISM: Homo sapiens

<400> SEQUENCE: 24
tcgcggaggc ttggggcagc cgggtagctc ggaggtcgtg gcgctggggg ctagcaccag     60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa    180
catttttttt taaaactgta ttgtttctcg ttttaattta ttttttgcttg ccattccccca  240 cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagcg aaagcgacag gggcaaagtg    420
agtgacctgc ttttggggt gaccgccgga gcgcggcgtg agccctcccc cttgggatcc     480
cgcagctgac cagtcgcgct gacggacaga cagacagaca ccgcccccag ccccagctac    540
cacctcctcc ccggccggcg gcggacagtg gacgcggcgg cgagccgcgg gcaggggccg    600
gagcccgcgc ccggaggcgg ggtggagggg gtcgggctc gcggcgtcgc actgaaactt     660
ttcgtccaac ttctgggctg ttctcgcttc ggaggagccg tggtccgcgc ggggggaagcc   720 gagccgagcg gagccgcgag aagtgctagc tcgggccggg aggagccgca gccggaggag    780
ggggaggagg aagaagagaa ggaagaggag agggggccgc agtggcgact cggcgctcgg    840
aagccgggct catggacggg tgaggcgcg gtgtgcgcag acagtgctcc agccgcgcgc     900
gctccccagg ccctggcccg ggcctcgggc cggggaggaa gagtagctcg ccgaggcgcc    960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
```

```
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa atgtgacaag ccgaggcggt gagccgggca ggaggaagga    1500
gcctccctca gggtttcgg                                                 1519

<210> SEQ ID NO 25
<211> LENGTH: 1723
<212> TYPE: DNA
<213> ORGANISM: Homo sapiens

<400> SEQUENCE: 25
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt taaaactgta ttgtttctcg ttttaattta ttttttgcttg ccattcccca     240 cttgaatcgg gccgacggct tggggagatt gctctacttc cccaaatcac tgtggatttt     300
ggaaaccagc agaagagga aagaggtagc aagagctcca gagagaagtc gaggaagaga      360
gagacggggt cagagagagc gcgcgggcgt gcgagcagcg aaagcgacag ggcaaagtg      420 agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcaggggccg     600
gagcccgcgc ccggaggcgg ggtggagggg gtcgggcgct cgcggcgtcgc actgaaactt     660 ttcgtccaac ttctgggctg ttctcgcttc ggaggagccg tggtccgcgc ggggaagcc      720 gagccgagcg gagccgcgag aagtgctagc tcgggccggg aggagccgca gccggaggag     780
ggggaggagg aagaagagaa ggaagaggag agggggccgc agtggcgact cggcgctcgg     840
aagccgggct catggacggg tgaggcggcg gtgtgcgcag acagtgctcc agccgcgcgc     900 gctcccagg ccctggcccg ggcctcgggc cggggaggaa gagtagctcg ccgaggcgcc     960
gaggagagcg ggccgcccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gttccctgtg ggccttgctc agagcggaga    1560
aagcatttgt ttgtacaaga tccgcagacg tgtaaatgtt cctgcaaaaa cacagactcg    1620
cgttgcaagg cgaggcagct tgagttaaac gaacgtactt gcagatgtga caagccgagg    1680
```

```
cggtgagccg ggcaggagga aggagcctcc ctcagggttt cgg          1723
```

<210> SEQ ID NO 26
<211> LENGTH: 1591
<212> TYPE: DNA
<213> ORGANISM: Homo sapiens

<400> SEQUENCE: 26

```
tcgcggaggc ttggggcagc cgggtagctc ggaggtcgtg gcgctggggg ctagcaccag    60
cgctctgtcg ggaggcgcag cggttaggtg gaccggtcag cggactcacc ggccagggcg   120
ctcggtgctg gaatttgata ttcattgatc cgggttttat ccctcttctt ttttcttaaa   180
catttttttt taaaactgta ttgtttctcg ttttaattta tttttgcttg ccattcccca   240
cttgaatcgg gccgacggct tggggagatt gctctacttc cccaaatcac tgtggatttt   300
ggaaaccagc agaaagagga aagaggtagc aagagctcca gagagaagtc gaggaagaga   360
gagacggggt cagagagagc gcgcgggcgt gcgagcagcg aaagcgacag gggcaaagtg   420
agtgacctgc ttttgggggt gaccgccgga gcgcggcgtg agccctcccc cttgggatcc   480
cgcagctgac cagtcgcgct gacggacaga cagacagaca ccgcccccag ccccagctac   540
cacctcctcc ccggccggcg gcggacagtg gacgcggcgg cgagccgcgg gcaggggccg   600
gagcccgcgc ccggaggcgg ggtggagggg gtcgggcttc gcggcgtcgc actgaaactt   660
ttcgtccaac ttctgggctg ttctcgcttc ggaggagccg tggtccgcgc gggggaagcc   720
gagccgagcg gagccgcgag aagtgctagc tcgggccggg aggagccgca gccgaggag    780
ggggaggagg aagaagagaa ggaagaggag aggggggccgc agtggcgact cggcgctcgg   840
aagccgggct catggacggg tgaggcgcg gtgtgcgcag acagtgctcc agccgcgcgc    900
gctccccagg ccctggcccg ggcctcgggc cggggaggaa gagtagctcg ccgaggcgcc   960
gaggagagcg ggccgcccca cagcccgagc cggagaggga gcgcgagccg cgccggcccc  1020
ggtcgggcct ccgaaaccat gaactttctg ctgtcttggg tgcattggag ccttgccttg  1080
ctgctctacc tccaccatgc caagtggtcc caggctgcac ccatggcaga aggaggaggg  1140
cagaatcatc acgaagtggt gaagttcatg gatgtctatc agcgcagcta ctgccatcca  1200
atcgagaccc tggtggacat cttccaggag taccctgatg agatcgagta catcttcaag  1260
ccatcctgtg tgcccctgat gcgatgcggg ggctgctgca atgacgaggg cctggagtgt  1320
gtgcccactg aggagtccaa catcaccatg cagattatgc ggatcaaacc tcaccaaggc  1380
cagcacatag gagagatgag cttcctacag cacaacaaat gtgaatgcag accaaagaaa  1440
gatagagcaa gacaagaaaa aaaatcagtt cgaggaaagg gaaaggggca aaaacgaaag  1500
cgcaagaaat cccggtataa gtcctggagc gtatgtgaca agccgaggcg gtgagccggg  1560
caggaggaag gagcctccct cagggtttcg g                                 1591
```

<210> SEQ ID NO 27
<211> LENGTH: 1774
<212> TYPE: DNA
<213> ORGANISM: Homo sapiens

<400> SEQUENCE: 27

```
tcgcggaggc ttggggcagc cgggtagctc ggaggtcgtg gcgctggggg ctagcaccag    60
cgctctgtcg ggaggcgcag cggttaggtg gaccggtcag cggactcacc ggccagggcg   120
ctcggtgctg gaatttgata ttcattgatc cgggttttat ccctcttctt ttttcttaaa   180
catttttttt taaaactgta ttgtttctcg ttttaattta tttttgcttg ccattcccca   240
```

```
cttgaatcgg gccgacggct tggggagatt gctctacttc cccaaatcac tgtggatttt      300
ggaaaccagc agaaagagga aagaggtagc aagagctcca gagagaagtc gaggaagaga      360
gagacggggt cagagagagc gcgcgggcgt gcgagcagcg aaagcgacag gggcaaagtg      420
agtgacctgc ttttgggggt gaccgccgga gcgcggcgtg agccctcccc cttgggatcc      480
cgcagctgac cagtcgcgct gacggacaga cagacagaca ccgcccccag ccccagctac      540
cacctcctcc ccggccggcg gcggacagtg gacgcggcgg cgagccgcgg gcaggggccg      600
gagcccgcgc ccggaggcgg ggtggagggg gtcggggctc gcggcgtcgc actgaaactt      660
ttcgtccaac ttctgggctg ttctcgcttc ggaggagccg tggtccgcgc gggggaagcc      720
gagccgagcg gagccgcgag aagtgctagc tcgggccggg aggagccgca gccggaggag      780
ggggaggagg aagaagagaa ggaagaggag aggggccgc agtggcgact cggcgctcgg       840
aagccgggct catggacggg tgaggcggcg gtgtgcgcag acagtgctcc agccgcgcgc      900
gctccccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaaccat gaactttctg ctgtcttggg tgcattggag ccttgccttg     1080
ctgctctacc tccaccatgc caagtggtcc caggctgcac ccatggcaga aggaggaggg     1140
cagaatcatc acgaagtggt gaagttcatg gatgtctatc agcgcagcta ctgccatcca     1200
atcgagaccc tggtggacat cttccaggag taccctgatg agatcgagta catcttcaag     1260
ccatcctgtg tgcccctgat gcgatgcggg ggctgctgca atgacgaggg cctggagtgt     1320
gtgcccactg aggagtccaa catcaccatg cagattatgc ggatcaaacc tcaccaaggc     1380
cagcacatag gagagatgag cttcctacag cacaacaaat gtgaatgcag accaaagaaa     1440
gatagagcaa gacaagaaaa aaaatcagtt cgaggaaagg gaaaggggca aaaacgaaag     1500
cgcaagaaat cccggtataa gtcctggagc gtgtacgttg gtgcccgctg ctgtctaatg     1560
ccctggagcc tccctggccc ccatccctgt gggccttgct cagagcggag aaagcatttg     1620
tttgtacaag atccgcagac gtgtaaatgt tcctgcaaaa acacagactc gcgttgcaag     1680
gcgaggcagc ttgagttaaa cgaacgtact tgcagatgtg acaagccgag gcggtgagcc     1740
gggcaggagg aaggagcctc cctcagggtt tcgg                                 1774
```